(12) United States Patent
Maguire et al.

(10) Patent No.: US 10,167,302 B2
(45) Date of Patent: *Jan. 1, 2019

(54) PHOSPHONATE NUCLEOSIDES USEFUL IN THE TREATMENT OF VIRAL DISEASES

(71) Applicants: University College Cork, Cork (IE); Katholieke Universiteit Leuven, Leuven (BE)

(72) Inventors: Anita Maguire, Cork (IE); Alan Ford, Cork (IE); Jan Balzarini, Heverlee (BE); Wim Dehaen, Heverlee (BE)

(73) Assignees: UNIVERSITY COLLEGE CORK, Cork (IE); KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/313,049

(22) PCT Filed: May 20, 2015

(86) PCT No.: PCT/EP2015/061430
§ 371 (c)(1),
(2) Date: Nov. 21, 2016

(87) PCT Pub. No.: WO2015/177351
PCT Pub. Date: Nov. 26, 2015

(65) Prior Publication Data
US 2017/0218001 A1  Aug. 3, 2017

(30) Foreign Application Priority Data

May 23, 2014  (EP) .................................... 14169644

(51) Int. Cl.
C07F 9/6561 (2006.01)
C07F 9/6512 (2006.01)
C07F 9/6558 (2006.01)

(52) U.S. Cl.
CPC ........ *C07F 9/65616* (2013.01); *C07F 9/6512* (2013.01); *C07F 9/65121* (2013.01); *C07F 9/65583* (2013.01)

(58) Field of Classification Search
CPC .. C07D 239/48; C07F 9/587; C07F 9/650941; C07F 9/65122; C07F 9/65127;
(Continued)

(56) References Cited

U.S. PATENT DOCUMENTS

2015/0291640 A1* 10/2015 Dehaen .............. C07F 9/65122
514/81

FOREIGN PATENT DOCUMENTS

WO  2012/034719 A1  3/2012
WO  2014/079903 A1  5/2014
WO  WO 2015/164573  * 10/2015  .......... C07D 473/40

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
(Continued)

*Primary Examiner* — Erich A Leeser
(74) *Attorney, Agent, or Firm* — Kenealy Vaidya LLP

(57) ABSTRACT

The present invention relates to a compound of formula (I), or a pharmaceutically acceptable salt or prodrug thereof, and their use in medicine particular as anti-viral agents;

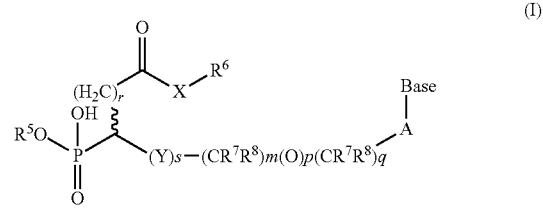

wherein:
X is selected from O and $NR^{11}$;
Y is selected from O, S and $NR^{12}$;
A is selected from $-(CR^1R^2)n-$, $-(CR^9R^{10})-$, $-(CR^9R^{10})-(CR^1R^2)n-$, $-(CR^1R^3)-(CR^2R^4)-(CR^1R^2)n-$, $-CR^3=CR^4-(CR^1R^2)n-$ and $-C\equiv C-(CR^1R^2)n-$;
$R^1$ and $R^2$ are independently selected from H, alkyl, hydroxyl, hydroxymethyl and halogen;
$R^3$ and $R^4$ are independently selected from H and alkyl, or $R_3$ and $R_4$ together with the carbon atoms to which they are attached form a mono or bicyclic ring system selected from cycloalkyl, cycloalkenyl, heterocycloalkyl, heterocycloalkenyl, aryl and heteroaryl;
$R^5$ is selected from H, $P(=O)(OH)_2$ and $P(=O)(OH)-O-P(=O)(OH)_2$;
$R^6$ is selected from H and alkyl;
$R^7$ and $R^8$ are independently selected from H, alkyl, halogen and hydroxymethyl
$R^9$ and $R^{19}$ together with the carbon atoms to which they are attached form a mono or bicyclic ring system selected from cycloalkyl, cycloalkenyl, heterocycloalkyl and heterocycloalkenyl;
$R^{11}$ is selected from H and alkyl;
$R^{12}$ is selected from H and alkyl;
m is 0, 1, 2 or 3;
n is 1, 2 or 3;
p is 0 or 1;
q is 0, 1, 2 or 3;

(Continued)

r is 0, 1, 2, 3, 4 or 5;
s is 0 or 1;
Base is a natural or non-natural nucleobase, and
wherein each alkyl, cycloalkyl, cycloalkenyl, heterocycloalkyl, heterocycloalkenyl, aryl and heteroaryl may be optionally substituted as described herein.

12 Claims, No Drawings

(58) Field of Classification Search
CPC .............. C07F 9/65216; C07F 9/65217; C07F 9/65218; C07F 9/6533; C07F 9/65583; C07F 9/65586; C07F 9/6561; C07F 9/65616; C07F 9/65685; C07F 9/657172; C07F 9/65846
See application file for complete search history.

(56) References Cited

OTHER PUBLICATIONS

International Search Report and Written Opinion issued in PCT/EP2015/0611430 dated Jul. 28, 2015.
Sebastien Debarge et al: "Design and Synthesis of [alpha]-Carboxy Phosphononucleosides", The Journal of Organic Chemistry, vol. 76, No. 1, Jan. 7, 2011 (Jan. 7, 2011), pp. 105-126.
Isabelle Hladezuk et al: "Development of OH insertion for the attachment of phosphonates to nucleosides; synthesis of -carboxy phosphononucleosides", Tetrahedron, Elsevier Science Publishers, Amsterdam, NL, vol. 68, No. 7, Dec. 29, 2011 (Dec. 29, 2011), pp. 1894-1909.
Boojamra CG et al: "Design, synthesis, and anti-HIV activity of 4'-modified carbocyclic nucleoside phosphonate reverse transcriptase inhibitors", Bioorganic & Medicinal Chemistry, Pergamon, GB, vol. 17, No. 4, Feb. 15, 2009 (Feb. 15, 2009), pp. 1739-1746.

* cited by examiner

PHOSPHONATE NUCLEOSIDES USEFUL IN THE TREATMENT OF VIRAL DISEASES

The present invention relates to modified phosphonucleosides. More specifically, but not exclusively, the invention relates to modified phosphonucleosides that are capable of treating one or more viral disorders, including DNA and RNA viruses.

BACKGROUND TO THE INVENTION

The human immunodeficiency virus (HIV) was first identified as the causative agent of acquired immunodeficiency syndrome (AIDS) in 1983.[1] At the close of 2010 there were an estimated 34 million people living with the retrovirus worldwide, with approximately 2.7 million people newly infected in 2009 alone.[2] The introduction of the drug regimen HAART (highly active antiretroviral therapy) in 1996 has transformed HIV from a lethal infection to a manageable chronic condition with considerable declines in HIV-associated morbidity and mortality.[3-6] However, as a result of the high genetic variability of the retrovirus, resistance to current drug therapies is a major problem and in addition to HIV there are numerous other chronic viral infections such as hepatitis B and C and human T-lymphotrophic virus 1 (HTLV-1).[7] Approximately 1 in 12 persons worldwide, or some 500 million people, are living with chronic viral hepatitis.2 In light of this, a vast amount of time and effort has been invested in the design and synthesis of antiviral agents, most notably nucleoside analogues and the discovery of new, more efficient antiviral agents is imperative.

Nucleoside reverse transcriptase inhibitors (NRTIs) were the first class of anti-HIV drugs approved and, despite the discovery of numerous other classes of anti-HIV agents (i.e. nucleotide reverse transcriptase inhibitors, non-nucleoside reverse transcriptase inhibitors, protease inhibitors, integrase inhibitors, cell entry inhibitors and co-receptor inhibitors), they have continued to play a pivotal role in HIV treatment.[8] NRTIs disrupt viral replication through two distinct modes; competitive inhibition of HIV RT with respect to the dNTP substrate, and DNA chain termination.[9,10] However, in order to do this, these compounds must be first converted via a series of host cell kinases to their active triphosphate form.[10-12] The triphosphorylated drug molecules then compete with bona fide nucleotides to be accepted into the growing DNA chain and, if incorporated, chain elongation is terminated since the NRTI lacks the 3'—OH group of endogenous nucleosides.[10] Poor cell membrane permeability coupled with the labile nature of the phosphate bond precludes the direct delivery of the active triphosphorylated form of the drug into the virus-infected cell.[13] This predicament was partially overcome by the use of phosphoramidate, CycloSal or alkoxyalkyl prodrug technology[14-17] and also the discovery of the phosphonate as a stable isostere for the phosphate bond.[18,19]

The discovery of (S)-HPMPA as a broad spectrum antiviral agent swiftly led to the development of a new class of antiviral agents; the nucleotide reverse transcriptase inhibitors (NtRTIs).[19,20] Tenofovir (PMPA) is the only nucleotide reverse transcriptase inhibitor currently approved by the FDA for the treatment of HIV and HBV. It is marketed as the prodrug tenofovir disoproxil fumarate (TDF) which is hydrolysed in vivo to tenofovir.[8,10] The presence of the phosphonate group enables the compound to bypass the initial phosphorylation, which is often the rate-limiting step, and just two phosphorylations are required to furnish the active tenofivir-diphosphate.8

Acyclic nucleoside analogues are an important subclass of NRTIs.[21] In addition to this, the antiviral properties of phosphonoformic acid (PFA) 8 and phosphonoacetic acid (PAA) 9 were established almost 3 decades ago.[22] McKenna et al. later synthesised a range of halogen- and methyl-substituted derivatives of PAA, a number of which were found to possess potent antiviral activity. Interestingly, the carbonyl derivative 10 was significantly more active than 9.[23]

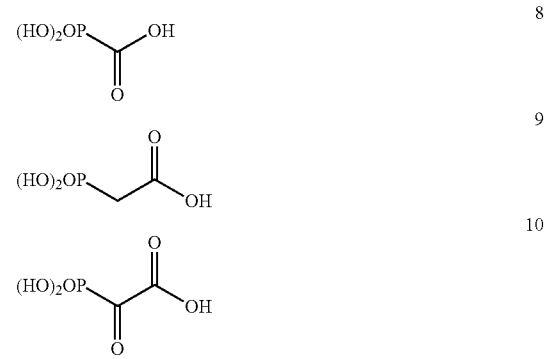

In general, phosphononucleoside research involves compounds bearing a simple $CH_2PO(OH)_2$ substituent; however, there have been some reports of derivatives bearing substituents geminal to the phosphonic acid moiety.[24-29] Gilbert and co-workers described the synthesis of citrate derivatives of nucleosides as potential mimics of nucleoside triphosphates.[30,31] The compounds were found to be inactive, indicating that the citrate moiety is not a good replacement for the phosphate group. Vedras et al. reported the synthesis of nucleoside dicarboxylates as potential nucleoside diphosphate isosteres.[32] Recently Janeba has described acyclic nucleoside phosphonates incorporating an additional remote carboxylic acid function, but these compounds did not exhibit any antiviral activity.[33] The attachment of PAA and PFA by ester and amide linkages to the 5'-O and N-positions of 3TC has been reported previously, but the resulting derivatives were less active against HIV-1 than the parent compound.[34]

The present invention seeks to provide further phosphononucleoside derivatives, particularly those that have therapeutic applications in the treatment of viral disorders, including DNA and RNA viruses such as HIV.

STATEMENT OF INVENTION

A first aspect of the invention relates to a compound of formula (I), or a pharmaceutically acceptable salt or prodrug thereof,

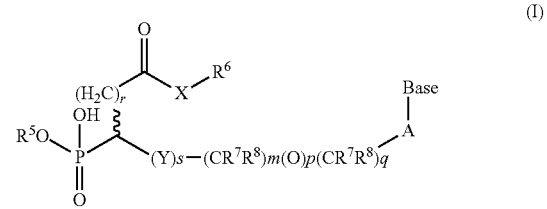

wherein:

X is selected from O and $NR^{11}$;

Y is selected from O, S and $NR^{12}$;

A is selected from —$(CR^1R^2)n$-, —$(CR^9R^{10})$—, —$(CR^9R^{10})$—$(CR^1R^2)n$-, —$(CR^1R^3)$—$(CR^2R^4)$—$(CR^1R^2)n$-, —$CR^3$=$CR^4$—$(CR^1R^2)n$- and —C≡C—$(CR^1R^2)n$-;

$R^1$ and $R^2$ are independently selected from H, alkyl, hydroxyl, hydroxymethyl and halogen;

$R^3$ and $R^4$ are independently selected from H and alkyl, or $R_3$ and $R_4$ together with the carbon atoms to which they are attached form a mono or bicyclic ring system selected from cycloalkyl, cycloalkenyl, heterocycloalkyl, heterocycloalkenyl, aryl and heteroaryl;

$R^5$ is selected from H, P(=O)(OH)$_2$ and P(=O)(OH)—O—P(=O)(OH)$_2$;

$R^6$ is selected from H and alkyl;

$R^7$ and $R^8$ are independently selected from H, alkyl, halogen and Hydroxymethyl;

$R^9$ and $R^{10}$ together with the carbon atom to which they are attached form a mono or bicyclic ring system selected from cycloalkyl, cycloalkenyl, heterocycloalkyl and heterocycloalkenyl;

$R^{11}$ is selected from H and alkyl;

$R^{12}$ is selected from H and alkyl;

m is 0, 1, 2 or 3;

n is 1, 2 or 3;

p is 0 or 1;

q is 0, 1, 2 or 3;

r is 0, 1, 2, 3, 4 or 5;

s is 0 or 1;

Base is a natural or non-natural nucleobase; and wherein each alkyl, cycloalkyl, cycloalkenyl, heterocycloalkyl, heterocycloalkenyl, aryl and heteroaryl may be optionally substituted as described herein.

A second aspect of the invention relates to a pharmaceutical composition comprising a compound of formula (I) as defined above and a pharmaceutically acceptable diluent, excipient or carrier.

Another aspect of the invention relates to a compound of formula (I) as defined above, or a pharmaceutically acceptable salt or prodrug thereof, for use in medicine.

Another aspect of the invention relates to a compound of formula (I) as defined above, or a pharmaceutically acceptable salt or prodrug thereof, for use in treating a viral disorder.

A further aspect of the invention relates to the use of a compound of formula (I) as defined above, or a pharmaceutically acceptable salt or prodrug thereof, in the preparation of a medicament for treating a viral disorder.

A further aspect of the invention relates to a method of treating a viral disorder, said method comprising administering to a mammal a therapeutically effective amount of compound of formula (I) as defined above, or a pharmaceutically acceptable salt or prodrug thereof.

Another aspect of the invention relates to the use of a compound of formula (I) as defined above, or a pharmaceutically acceptable salt or prodrug thereof, in an assay for identifying further candidate compounds capable of inhibiting HIV-RT.

A further aspect of the invention relates to a process for preparing compound of formula (I) as defined above, or a pharmaceutically acceptable salt or prodrug thereof.

DETAILED DESCRIPTION

The present invention relates to phosphononucleoside derivatives of formula (I) as defined above, along with therapeutic uses thereof.

As will be evident from the general formula (I) and the definitions associated therewith, there may be one or several asymmetric carbon atoms present in the presently claimed phosphonucleosides depending on the nature of the substituents. The phosphonucleosides are intended to include all stereoisomers arising from the presence of any and all asymmetric carbon atoms (including substituents on the ring, as well as on side chains thereof), as well as mixtures thereof, including racemic mixtures.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group. Particularly preferred alkyl groups include, for example, methyl, ethyl, propyl, isopropyl, butyl, isobutyl, tert-butyl, pentyl and hexyl. Suitable substituents include one or more groups selected from —OH, —SH, —NH$_2$, —CF$_3$, —NH-alkyl, —N(alkyl)$_2$, alkoxy, halogen, —CN, N$_3$, —CO$_2$-alkyl, —CO$_2$H. Preferably, the alkyl group is a $C_{1-6}$ alkyl group. Preferably the $C_{1-6}$ alkyl group is unsubstituted.

As used herein, the term "cycloalkyl" refers to a monocyclic or bicyclic $C_{3-10}$ alkyl ring, preferably, $C_{3-7}$-cycloalkyl, more preferably $C_{5-7}$-cycloalkyl. Preferred examples include cyclopropyl, cyclobutyl, cyclopentyl, cyclohexyl or cycloheptyl, or a fused bicyclic ring system such as norbornane. Suitable substituents include one or more groups selected from —OH, —SH, —NH$_2$, —CF$_3$, —NH-alkyl, —N(alkyl)$_2$, alkoxy, halogen, —CN, N$_3$, —CO$_2$-alkyl, —CO$_2$H. Preferably, the cycloalkyl group is a $C_{5-6}$ cycloalkyl group. Preferably the $C_{5-6}$ cycloalkyl group is unsubstituted.

As used herein, the term "cycloalkenyl" refers to a monocyclic or bicyclic $C_{3-10}$ alkenyl ring possessing 1, 2 or 3 (preferably 1 or 2, more preferably 1) alkene groups. Preferably, the ring is $C_{3-7}$-cycloalkenyl, more preferably a $C_{5-7}$-cycloalkenyl. Preferred examples include cyclopentenyl, cyclohexenyl or cycloheptenyl, or a fused bicyclic ring system such as norbornene. Suitable substituents include one or more groups selected from —OH, —SH, —NH$_2$, —CF$_3$, —NH-alkyl, —N(alkyl)$_2$, alkoxy, halogen, —CN, N$_3$, —CO$_2$-alkyl, —CO$_2$H. Preferably, the cycloalkenyl group is a $C_{5-6}$ cycloalkenyl group. Preferably the $C_{5-6}$ cycloalkyl group is unsubstituted.

As used herein, the term "heterocycloalkyl" refers to a monocyclic or bicyclic $C_{3-10}$ aliphatic group containing one or more heteroatoms selected from nitrogen, oxygen and sulphur, which is optionally interrupted by one or more —(CO)— groups in the ring. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Suitable heterocycloalkyl groups include, but are not limited to, aziridinyl, oxiranyl, thiiranyl, azetidinyl, oxetanyl, thietanyl, pyrrolidinyl, tetrahydrofuranyl, tetrahydrothiophenyl, pyrazolidinyl, imidazolidinyl, 3-dioxolanyl, thiazolidinyl, isoxazolidinyl, piperidinyl, piperazinyl, morpholinyl, 1,4-dioxanyl, thiomorpholinyl, 1,4-oxathianyl, 1,4-dithianyl, 1,3,5-trioxanyl, 1,3,5-thrithianyl. Suitable substituents include one or more groups selected from —OH, —SH, —NH$_2$, —CF$_3$, —NH-alkyl, —N(alkyl)$_2$, alkoxy, halogen, —CN, —N$_3$, —CO$_2$-alkyl, —CO$_2$H. Preferably, the heterocycloalkyl group is a $C_{5-6}$ heterocycloalkyl group. Preferably the $C_{5-6}$ heterocycloalkyl group is unsubstituted.

As used herein, the term "heterocycloalkenyl" refers to a $C_{3-10}$ monocyclic or bicyclic ring system containing one or more double bonds (preferably 1) and one or more heteroatoms selected from nitrogen, oxygen and sulphur in the ring, and which is optionally interrupted by one or more —(CO)— groups in the ring. Preferably, the heterocycloalkenyl group is a $C_{3-7}$-heterocycloalkenyl, more preferably a $C_{3-6}$-heterocycloalkenyl. Alternatively, the heterocycloalkenyl group is a $C_{4-7}$-heterocycloalkenyl, more preferably a $C_{4-6}$-heterocycloalkenyl. Preferred heterocycloalkyl groups include, but are not limited to, pyrrolyl, furanyl, pyrrolinyl, thiophenyl, pyrazolyl, imidazole, oxazole, isoxazole, pyrazolinyl, thiazolyl, isothiazolyl, triazolyl, tetrazolyl, pyridinyl, pyridazinyl, pyrimidinyl and pyrazinyl. Suitable substituents include one or more groups selected from —OH, —SH, —$NH_2$, —$CF_3$, —NH-alkyl, —N(alkyl)$_2$, alkoxy, halogen, —CN, $N_3$, —$CO_2$-alkyl, —$CO_2H$. Preferably, the heterocycloalkyl group is a $C_{5-6}$ heterocycloalkenyl group. Preferably the $C_{5-6}$ heterocycloalkenyl group is unsubstituted.

As used herein, the term "aryl" refers to a $C_{6-12}$ aromatic group which may be substituted (mono- or poly-) or unsubstituted. More preferably, the aryl group is a $C_{6-10}$ aromatic group. Typical examples include phenyl and naphthyl etc. Suitable substituents include one or more groups selected from alkyl, —OH, —SH, —$NH_2$, —$CF_3$, —NH-alkyl, —N(alkyl)$_2$, alkoxy, halogen, —CN, $N_3$, —$CO_2$-alkyl, —$CO_2H$. Preferably the aryl group is unsubstituted phenyl.

As used herein, the term "heteroaryl" refers to a monocyclic or bicyclic $C_{5-12}$ aromatic ring comprising one or more (preferably 1 or 2) heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc.

As used herein, the term "halogen" includes chloro, bromo, iodo and fluoro.

As used herein, the term "base" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C_3$-$C_6$)-alkynylcytosine, 5-fluorouracil, 5-bromouracil, pseudoisocytosine, 2-hydroxy-S-methyl-4-triazolopyridine, isocytosine, isoguanine, inosine and the "non-naturally occurring" nucleobases described in Benner et al., U.S. Pat. No. 5,432,272. The term "nucleobase" is intended to cover all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

In one preferred embodiment, the base is a purine or pyrimidine nucleobase. In one preferred embodiment, the base is a nucleobase selected from adenine (A), cytosine (C), 5-methylcytosine (MeC), isocytosine, pseudoisocytosine, guanine (G), thymine (T), uracil (U), 5-bromouracil, 5-propynyluracil, 5-fluorouracil, 5-(2-halovinyl)uracil, N-4 substituted cytosine (i.e. hydroxylamine), 5-propynyl-6-fluorouracil, 5-methylthiazole-uracil, 6-aminopurine, 2-aminopurine, inosine, 2,6-diaminopurine, 7-propyne-7-deazaadenine, 7-propyne-7-deazaguanine, 5-thiazolyluracil, 2-thiothymine, 4-thiothymine, 5-propynyl-cytosine, 5-thiazolylcytosine, phenoxazine, G-clamp, $N^2$-aminopropylguanine and 2-chloro-6-aminopurine.

In one particularly preferred embodiment, the base is a nucleobase selected from A, C, MeC, G, T, 5-fluorouracil and U.

In one embodiment, X is O and $R^6$ is H or $C_{1-3}$ alkyl, preferably H or Me, more preferably H.

In one embodiment, Y is O and s is 1.

In one embodiment $R^1$ and $R^2$ are independently selected from H, $C_{1-3}$ alkyl, and hydroxymethyl. In a further embodiment, $R^1$ and $R^2$ are independently selected from H and $C_{1-3}$ alkyl.

In one embodiment, $R^7$ and $R^8$ are independently selected from H and $C_{1-3}$ alkyl.

In one embodiment, A is a heteroaryl group, more preferably, a triazolyl group.

In one embodiment, A is selected from —$(CR^1R^2)n$-, —$(CR^1R^3)$—$(CR^2R^4)$—$(CR^1R^2)n$-, —$CR^3$=$CR^4$—$(CR^1R^2)n$- and —C≡C—$(CR^1R^2)n$-. In another embodiment, A is selected from —$(CR^1R^2)n$-, —$CR^3$=$CR^4$—$(CR^1R^2)n$- and —C≡C—$(CR^1R^2)n$-. In another embodiment, A is —$(CR^1R^2)n$. In another embodiment, A is —$(CR^1R^3)$—$(CR^2R^4)$—$(CR^1R^2)n$. In another embodiment, A is selected from —$CR^3$=$CR^4$—$(CR^1R^2)n$- and —C≡C—$(CR^1R^2)n$-.

Where $R^3$ and $R^4$ together with the carbon atoms to which they are attached form a heteroaryl, heterocycloalkyl, or heterocycloalkenyl group, the link between the group "A" and the Base and/or "A" and the rest of the molecule, i.e. the link to the —$(CR^7R^8)_m(O)_p(CR^7R^8)_q$, may be via a carbon or via a heteroatom, preferably via a carbon.

In one embodiment, $R^3$ and $R^4$ are independently selected from H and alkyl, or $R_3$ and $R_4$ together with the carbon atoms to which they are attached form a mono or bicyclic ring system selected from cycloalkyl, cycloalkenyl, and aryl.

In one embodiment, m is 1 or 2, preferably m is 1.
In one embodiment, n is 1 or 2, preferably n is 1.
In one embodiment, p is 0. In one embodiment, s is 0. In a preferred embodiment, s is 1 and p is 0. In another preferred embodiment, both s and p are 0.
In one embodiment, q is 0 or 1, preferably q is 0.
In one embodiment, r is 0 or 1, preferably r 0.
In a preferred embodiment, m is 1, n is 1, p is 0, q is 0 and r is 0.
In one embodiment, $R^5$ is H.
In one embodiment, $R^9$ and $R^{10}$ together with the carbon atoms to which they are attached form a mono or bicyclic ring system selected from cycloalkyl and cycloalkenyl.

In a preferred embodiment, A is selected from —$CR^3$=$CR^4$—$(CR^1R^2)n$- and —C≡C—$(CR^1R^2)n$-, n is 1, and $R^1$, $R^2$, $R^3$ and $R^4$ are independently selected from H and $C_{1-3}$ alkyl, in a more specific embodiment thereof Y is O.

In a further preferred embodiment, A is selected from —$CR^3$=$CR^4$—$(CR^1R^2)n$- and —C≡C—$(CR^1R^2)n$-, $R^1$, $R^2$, $R^3$ and $R^4$ are independently selected from H and $C_{1-3}$ alkyl, m is 1, n is 1, p is 0, q is 0, r is 0, s is 1 and $R^5$ is H, in a more specific embodiment thereof Y is O.

In another preferred embodiment, A is —(CR$^1$R$^3$)—(CR$^2$R$^4$)—(CR$^1$R$^2$)n-, n is 1, R$^1$ and R$^2$ are independently selected from H and C$_{1-3}$ alkyl and R$^3$ and R$^4$ together with the carbon atoms to which they are attached form a mono or bicyclic ring system selected from cycloalkyl, cycloalkenyl, and aryl, in a more specific embodiment thereof Y is O.

In a further preferred embodiment, A is —(CR$^1$R$^3$)—(CR$^2$R$^4$)—(CR$^1$R$^2$)n-, R$^1$ and R$^2$ are independently selected from H and C$_{1-3}$ alkyl and R$^3$ and R$^4$ together with the carbon atoms to which they are attached form a mono or bicyclic ring system selected from cycloalkyl, cycloalkenyl, and aryl, m is 1, n is 1, p is 0, q is 0, r is 0, s is 1 and R$^5$ is H, in a more specific embodiment thereof Y is O. Especially preferred ring systems in these embodiments include phenyl, cyclopentyl, cyclohexyl, cyclopentenyl, cyclohexenyl, cyclopropyl and norbornenyl.

In another preferred embodiment, A is —(CR$^1$R$^2$)n-, n is 1 or 2, and R$^1$ and R$^2$ are independently selected from H and C$_{1-3}$ alkyl.

In another preferred embodiment, m is 1, n is 1, s is 1, p is 0, q is 0, r is 0, and base is a purine or pyrimidine nucleobase, in a more specific embodiment thereof Y is O.

In one preferred embodiment,
s is 1;
Y is O;
X is O;
R$^5$ and R$^6$ are both H;
m is 0 or 1;
p, q and r are all 0;
A is —(CR$^1$CR$^2$)$_n$—;
n is 1, 2 or 3;
R$^1$ and R$^1$ are each independently selected from H and alkyl and hydroxyalkyl;
R$^7$ and R$^8$ are each independently selected from H and alkyl;
p, q and r are all 0.

In one preferred embodiment,
s is 1;
Y is O;
X is O;
R$^5$ and R$^6$ are both H;
m, p, q and r are all 0;
A is —(CR$^1$CR$^2$)$_n$—;
n is 2 or 3; and
R$^1$ and R$^1$ are each independently selected from H and alkyl.

In another preferred embodiment,
s is 1;
Y is O;
X is O;
R$^5$ and R$^6$ are both H;
m is 1;
R$^7$ and R$^8$ are each independently selected from H and alkyl;
p, q and r are all 0;
A is —(CR$^1$CR$^2$)$_n$—;
n is 1; and
R$^1$ and R$^1$ are each independently selected from H, alkyl and hydroxyalkyl.

In another preferred embodiment,
s is 1;
Y is O;
X is O;
R$^5$ is H;
R$^6$ is H or alkyl;
p, q and r are all 0;
m is 1;
R$^7$ and R$^8$ are each independently selected from H and alkyl;
A is selected from —(CR$^1$CR$^2$)$_n$—, —(CR$^3$=CR$^4$)—(CR$^1$CR$^2$)$_n$—, —C≡C—(CR$^1$CR$^2$)$_n$—, —(CR$^9$R$^{10}$)—(CR$^1$R$^2$)$_n$—;
n is 1 or 2;
R$^1$ and R$^2$ are each independently selected from H and alkyl,
R$^3$ and R$^4$ are each independently selected from H and alkyl, or together with the carbon atoms to which they are attached form a phenyl ring; and
R$^9$ and R$^9$ together with the carbon atom to which they are attached form a cyclohexyl, cyclopropyl, cyclopentyl, cyclohexenyl or norbornenyl ring.

In another preferred embodiment,
Y is O;
s is 1;
X is O;
R$^5$ and R$^6$ are both H;
A is —(CR$^1$R$^3$)—(CR$^2$R$^4$)—(CR$^1$R$^2$)$_n$—;
n is 1;
m, p, q and r are all 0;
R$^1$ and R$^2$ are each independently selected from H, hydroxyl, hydroxymethyl and alkyl;
R$^3$ and R$^4$ are each independently selected from H and alkyl.

In another preferred embodiment,
Y is O;
s is 1;
X is O;
R$^5$ and R$^6$ are both H;
A is —(CR$^1$R$^2$)$_n$—;
n is 1;
m is 1;
p, q and r are all 0;
R$^1$ and R$^2$ are each independently selected from H and alkyl;
R$^7$ and R$^8$ are each independently selected from H, alkyl and hydroxymethyl.

In one preferred embodiment, the compound of formula (I), or a pharmaceutically acceptable salt or prodrug thereof, is a compound of formula (Ia), or a pharmaceutically acceptable salt or prodrug thereof.

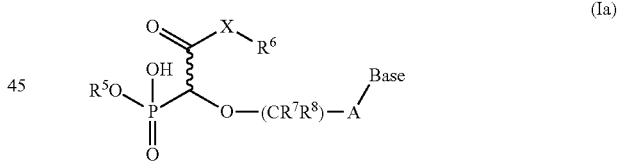

(Ia)

wherein:
X is selected from O and NR$^{11}$;
A is selected from —(CR$^1$R$^2$)n-, —(CR$^1$R$^3$)—(CR$^2$R$^4$)—(CR$^1$R$^2$)n-, —CR$^3$=CR$^4$—(CR$^1$R$^2$)n- and —C≡C—(CR$^1$R$^2$)n-;
R$_1$ and R$_2$ are independently selected from H and C$_{1-6}$-alkyl;
R$_3$ and R$_4$ are independently selected from H and C$_{1-6}$-alkyl, or R$_3$ and R$_4$ together with the carbon atoms to which they are attached form a mono or bicyclic ring system selected from C$_3$-C$_{10}$ cycloalkyl, C$_3$-C$_{10}$ heterocycloalkyl, C$_3$-C$_{10}$ cycloalkenyl, aryl and heteroaryl;
R$_5$ is selected from H, P(=O)(OH)$_2$ and P(=O)(OH)—O—P(=O)(OH)$_2$;
R$_6$ is selected from H and C$_{1-6}$-alkyl;
R$_7$ and R$_8$ are independently selected from H and C$_{1-6}$-alkyl;
R$^{11}$ is selected from H and C$_{1-6}$-alkyl;
n is 1 or 2; and
Base is a natural or non-natural nucleobase.

In one highly preferred embodiment, the compound is selected from the following, and pharmaceutically acceptable salts and prodrugs thereof:
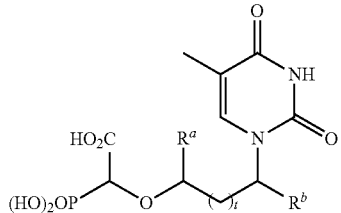
8a $R^a = R^b = H, t = 0$
8b $R^a = Me, R^b = H, t = 0$
8c $R^a = H, R^b = Me, t = 0$
8d $R^a = R^b = H, t = 1$
8e $R^a = H, R^b = CH_2OH, t = 0$
24
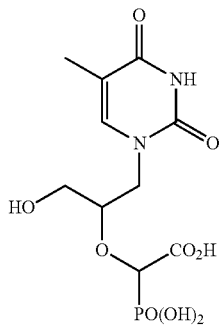
26
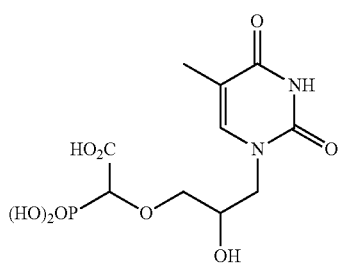
13a
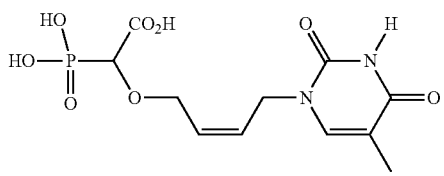
13b
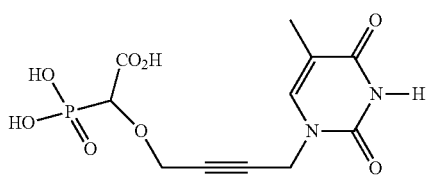
13c
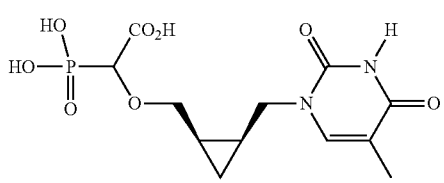
13d
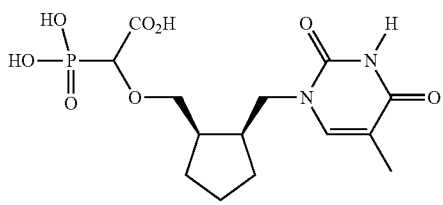
13e
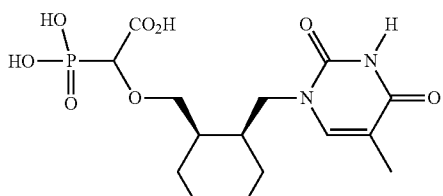
13f
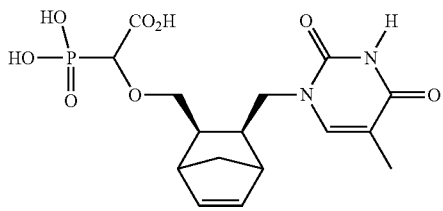
13g
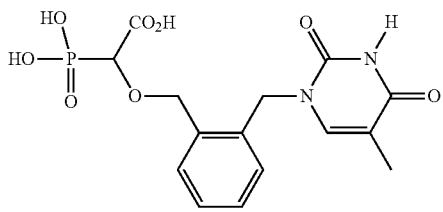
13h
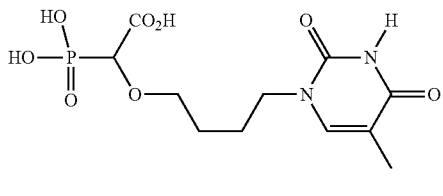
13i
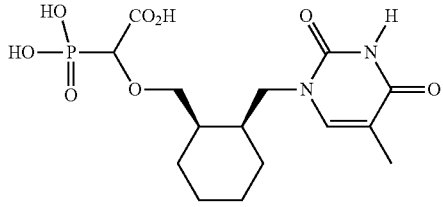
13j
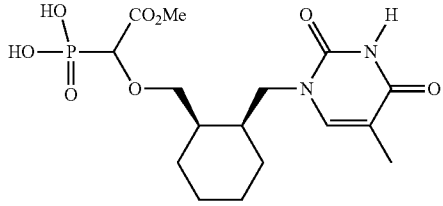
13k
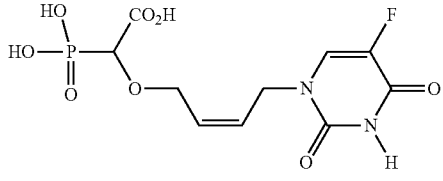

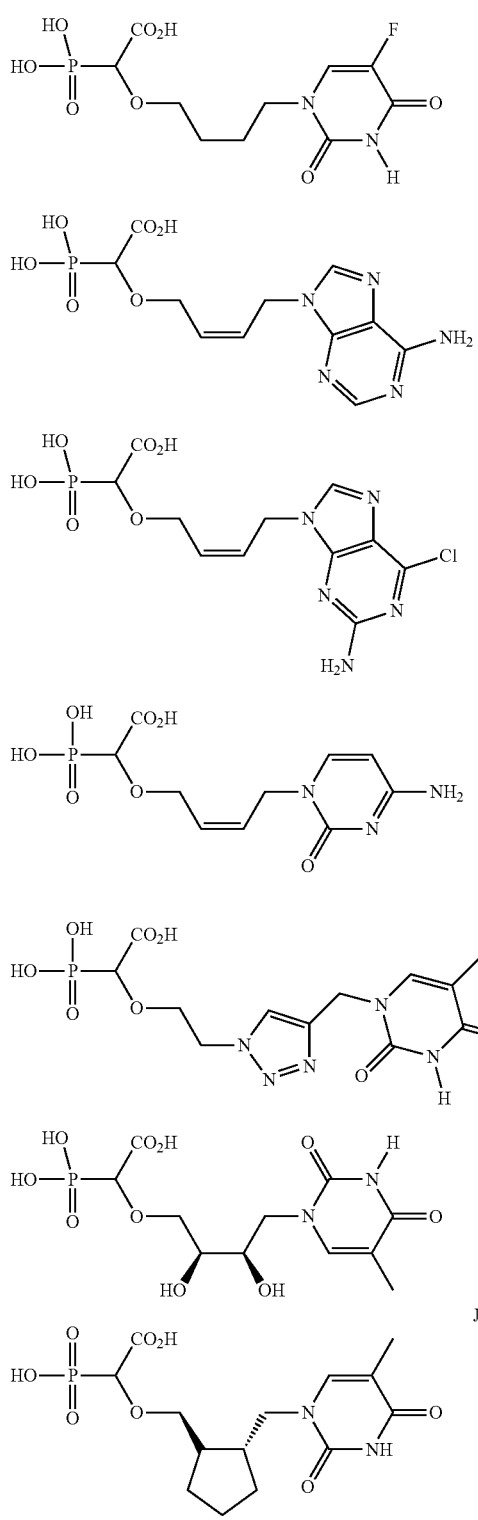

capable of inhibiting the HIV-RT catalysed incorporation of [$^3$H]dNTP into a homopolymeric or heteropolymeric template/primer. Further details of this assay are set forth in the accompanying Examples section. In one particularly preferred embodiment, the compound of the invention exhibits an $IC_{50}$ value in this assay of less than about 100 μg/ml, more preferably, less than about 50 μg/ml, even more preferably, less than about 20 μg/ml, more preferably still, less than about 10 μg/ml, even more preferably, less than about 5 μg/ml or 2 μg/ml. In one highly preferred embodiment, the compound of the invention exhibits an $IC_{50}$ value in this assay of less than about 1 μg/ml, even more preferably, less than about 0.5 μg/ml, more preferably still, less than about 0.1 μg/ml.

Therapeutic Use

The compounds of the invention have been found to inhibit viral enzymes required for virus replication, in particular, reverse transcriptase, and thus have potential therapeutic applications in the treatment of viral disorders.

Thus, one aspect of the invention relates to a compound of formula (I) (or a compound of formula (Ia) or any subgroup of a compound of formula (I) or (Ia)), or a pharmaceutically acceptable salt or prodrug thereof, for use in treating or preventing a viral disorder.

Another aspect of the invention relates to the use of a compound of the invention, or a pharmaceutically acceptable salt thereof, in the preparation of a medicament for treating or preventing a viral disorder.

A further aspect of the invention relates to a method of treating a viral disorder, said method comprising administering to a subject in need thereof, a compound of the invention or a pharmaceutically acceptable salt or prodrug thereof. Preferably, the viral disorder is an RNA- or DNA-dependent viral disorder.

As used herein the phrase "preparation of a medicament" includes the use of one or more of the above described compounds directly as the medicament in addition to its use in a screening programme for further anti-viral agents or in any stage of the manufacture of such a medicament.

One preferred embodiment therefore relates to the use of one or more compounds of the invention in the treatment of a viral disorder. Preferably, the viral disorder is an RNA virus or a DNA virus.

In one preferred embodiment, the viral disorder is an RNA virus.

In one preferred embodiment, the viral disorder is a DNA virus.

In another preferred embodiment, the viral disorder is a viral infection with Herpesvirales, more specifically a virus of the family of herpeseviriday.

In another preferred embodiment, the viral disorder is a viral infection with retroviriday, more specifically a lentivirus.

In one preferred embodiment, the virus is selected from human cytomegalovirus (HCMV), herpes simplex virus type 1 (HSV-1) and type 2 (HSV-2), human immunodeficiency virus type 1 (HIV-1) and type 2 (HIV-2), HTLV-I or II, varicella-zoster virus (VZV), respiratory viruses such as influenza virus (INF) and respiratory syncytial virus (RSV), flaviviruses (i.e. Dengue virus, hepatitis C virus), hepatitis B virus, coronavirus.

In one especially preferred embodiment, the virus is HIV, particularly HIV-1.

As defined herein, an antiviral effect within the scope of the present invention may be demonstrated by the ability to inhibit HIV-RT in a cell-free HIV-RT assay. This assay, including methods for its performance, is described in more The above described embodiments, preferred embodiments and particularly preferred embodiments may be combined with one another and apply equally to the compound of formula (I) and (Ia).

In one preferred embodiment, the compound of the invention is capable of inhibiting HIV-RT in a cell free HIV-RT assay. More specifically, the compound of the invention is detail in the accompanying Examples. Using such assays it may be determined whether a compound is antiviral in the context of the present invention.

In one preferred embodiment, the compound is capable of inhibiting HIV-1-RT-catalysed incorporation of [$^3$H]dTTP in a poly rA/oligodT template/primer.

In one preferred embodiment, the compound is capable of inhibiting HIV-1-RT-catalysed incorporation of [$^3$H]dCTP in a poly rI/oligidC template/primer.

In one preferred embodiment, the compound is capable of inhibiting HIV-1-RT-catalysed incorporation of [$^3$H]dATP in a poly rU/oligodA template/primer.

In one embodiment, the compound of the invention is administered in an amount sufficient to inhibit HIV-1-RT in a cell free HIV-RT assay.

Pharmaceutical Compositions

A further aspect of the invention relates to a pharmaceutical composition comprising a compound of the invention admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate and hydrate forms of the compounds of the present invention. The terms used in the claims encompass these forms.

Polymorphs

The invention furthermore relates to the compounds of the present invention in their various crystalline forms, polymorphic forms and (an)hydrous forms as well as amorphous form. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of the invention wherein one or more appropriate groups have been modified such that the modification may be reversed upon administration to a human or mammalian subject. Such reversion is usually (but not necessarily) performed by an enzyme naturally present in such subject, though it is possible for a second agent to be administered together with such a prodrug in order to perform the reversion in vivo. Examples of such modifications include ester (for example, any of those described above), wherein the reversion may be carried out by an esterase etc. Other such systems will be well known to those skilled in the art.

In one preferred embodiment of the invention, the prodrug is selected from a phosphoramidate derivative, a SATE (S-acyl-2-thioethyl) ester derivative, a pivaloyloxymethyl (POM) derivative, an isopropyloxymethylcarbonyl (POC) derivative and a cycloSal derivative, an alkyloxyalkyl derivative.

Suitable phosphoramidate derivatives will be familiar to a person skilled in the art and include, by way of example, compounds of formula (II),

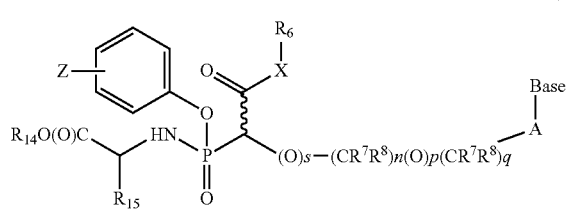

(II)

wherein $R_{15}$ is any side chain of an amino acid (more preferably, alkyl), $R_{14}$ is alkyl or aryl, Z is an optional substituent (for example one or more groups selected from alkyl, —OH, —SH, —NH$_2$, —CF$_3$, —NH-alkyl, —N(alkyl)$_2$, alkoxy, —N$_3$, —NO$_2$, halogen, —CN, —CO$_2$— alkyl and —CO$_2$H) and all the other substituents are as herein before defined.[35]

In an alternative preferred embodiment, the prodrug is of formula (III),

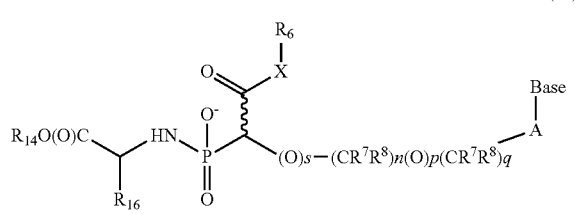

(III)

where $R_{14}$ is alkyl or aryl, and $R_{16}$ is any side chain of an amino acid (more preferably alkyl) and all the other substituents are as herein before defined.[36]

Suitable POM derivatives' will be familiar to a person skilled in the art and include, by way of example, compounds of formula (IV):

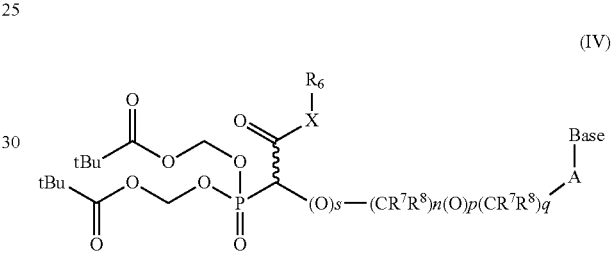

(IV)

Suitable SATE derivatives[38] will be familiar to a person skilled in the art and include, by way of example, compounds of formula (V):

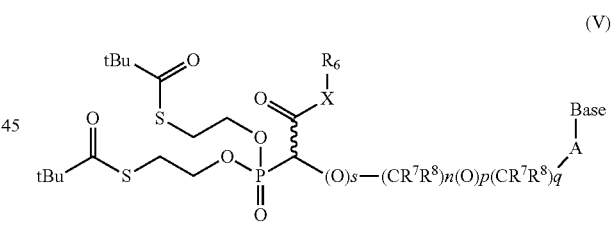

(V)

Suitable POC derivatives[39] will be familiar to a person skilled in the art and include, by way of example, compounds of formula (VI):

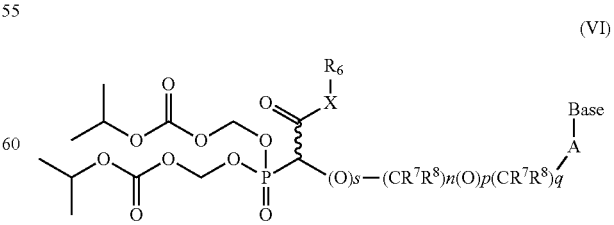

(VI)

Suitable cycloSaltype derivatives[40] will be familiar to a person skilled in the art and include, by way of example, compounds of formula (VII),

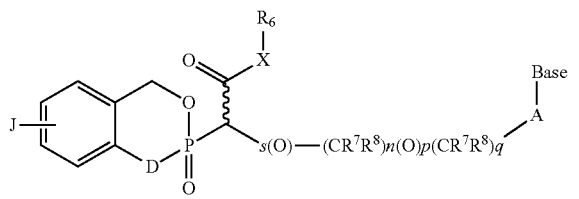

(VII)

wherein D is O ("cycloSal" derivatives) or NH ("cycloAMb" derivatives), and J is a substituent selected from $C_{1-6}$-alkyl and halogen, wherein the alkyl group is optionally further substituted with one or more additional groups, including alkyloxy, $CO_2$-alkyl, OCO-alkyl, $CO_2CH_2OCO$-alkyl and $CO_2CH_2OCOO$-alkyl and all the other substituents are as herein before defined. Preferably, D is O.

Preferably, the substituent J is selected from Me, methoxy, $^tBu$, $CH_2CH_2CO_2C_{1-6}$-alkyl, $CH_2CH_2OCO$ $C_{1-6}$-alkyl, $CH_2CH_2CO_2CH_2OCOC_{1-6}$-alkyl and $CH_2CH_2CO_2CH_2OCOOC_{1-6}$-alkyl.

In one highly preferred embodiment, the cycloSal moiety is selected from the following, wherein the wavy line represents the point of attachment to the rest of the molecule:

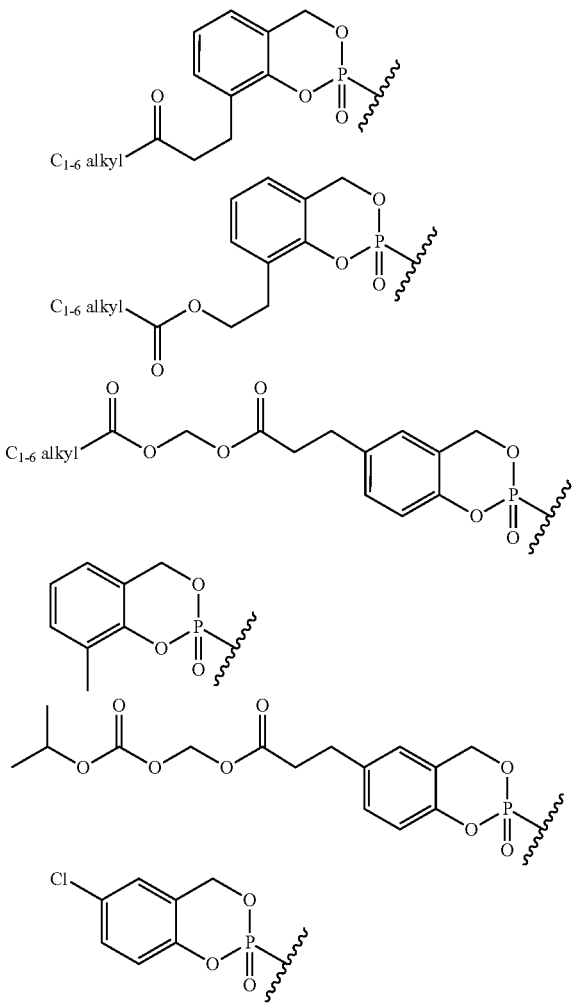

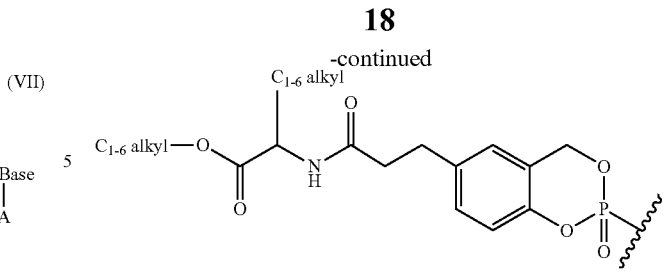

where $C_{1-6}$-alkyl is, for example, Me or $^tBu^{41}$ or any side chain of an amino acid.

Other nucleoside prodrugs such as the alkoxyalkyl derivatives will be familiar to the person skilled in the art[42].

Administration

The pharmaceutical compositions of the present invention may be adapted for oral, rectal, parenteral, intramuscular, intraperitoneal, intraarterial, intrathecal, intrabronchial, subcutaneous, intradermal, intravenous, nasal, vaginal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, vaginal rings, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 300 mg/day or more preferably, 10 to 150 mg/day, will be administered to the patient for the treatment of a viral disorder.

Combinations

In a particularly preferred embodiment, the one or more compounds of the invention are administered in combination with one or more other active agents, for example, existing antiviral drugs or pharmacological enhancers available on the market. In such cases, the compounds of the invention may be administered consecutively, simultaneously or sequentially with the one or more other active agents.

Antiviral drugs in general are more effective when used in combination. In particular, combination therapy is desirable in order to avoid an overlap of major toxicities, mechanism of action and afford complementary resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of resistance.

Assays

Another aspect of the invention relates to the use of a compound of the invention as defined hereinabove in an assay for identifying further candidate compounds that are capable of inhibiting HIV-1-RT.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, fixed on a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Synthesis

A further aspect of the invention relates to a process for preparing compound of formula (I) as defined above, or a pharmaceutically acceptable salt or prodrug thereof. In one embodiment the process for preparing a compound of formula (I), as hereinbefore defined, comprises reacting a compound of formula (X), wherein P is a protecting group, such as alkyl, and all the other substituents are as hereinbefore defined, with a compound of formula (XI), wherein all the substituents are as hereinbefore defined.

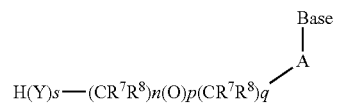

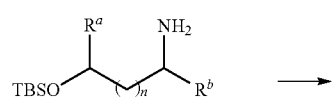

The reaction is preferably performed in the presence of a catalyst, such as a rhodium or copper catalyst, especially rhodium (II) acetate or copper (II) triflate. Preferably Y is O and s is 1. The compounds of formula (X) and (XI) may be additionally protected during the reaction by methods well known to those skilled in the art. The process further comprises removing the protecting groups to afford the compound of formula (I) and optionally converting the compound to a pharmaceutically acceptable salt or prodrug thereof.

In one embodiment the process for preparing a compound of formula (I) as hereinbefore defined comprises reacting a compound of formula (XX), wherein P is a protecting group, such as alkyl, and all the other substituents are as hereinbefore defined, with a base as hereinbefore defined.

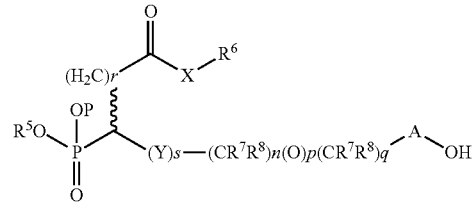

The reaction is preferably performed under mitsonobu conditions for example in the presence of triphenyl phosphine and a dialkylazodicarboxylate, such as DEAD or DIAD. The base and the compound of formula (XX) may be additionally protected during the reaction by methods well known to those skilled in the art. The process further comprises removing the protecting groups to afford the compound of formula (I) and optionally converting the compound to a pharmaceutically acceptable salt or prodrug thereof.

Compounds of formula (I) may be prepared according to the following general scheme 1:

Scheme 1

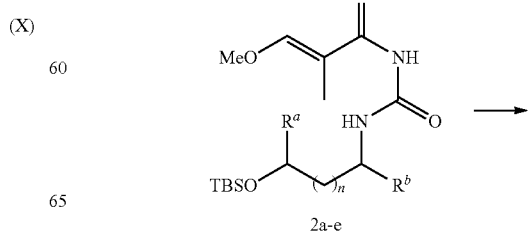

1a $R^a = R^b = H, t = 0$
1b $R^a = Me, R^b = H, t = 0$
1c $R^a = H, R^b = Me, t = 0$
1d $R^a = R^b = H, t = 1$
1e $R^a = H, R^b = CH_2OTBS, t = 0$ 2a-e

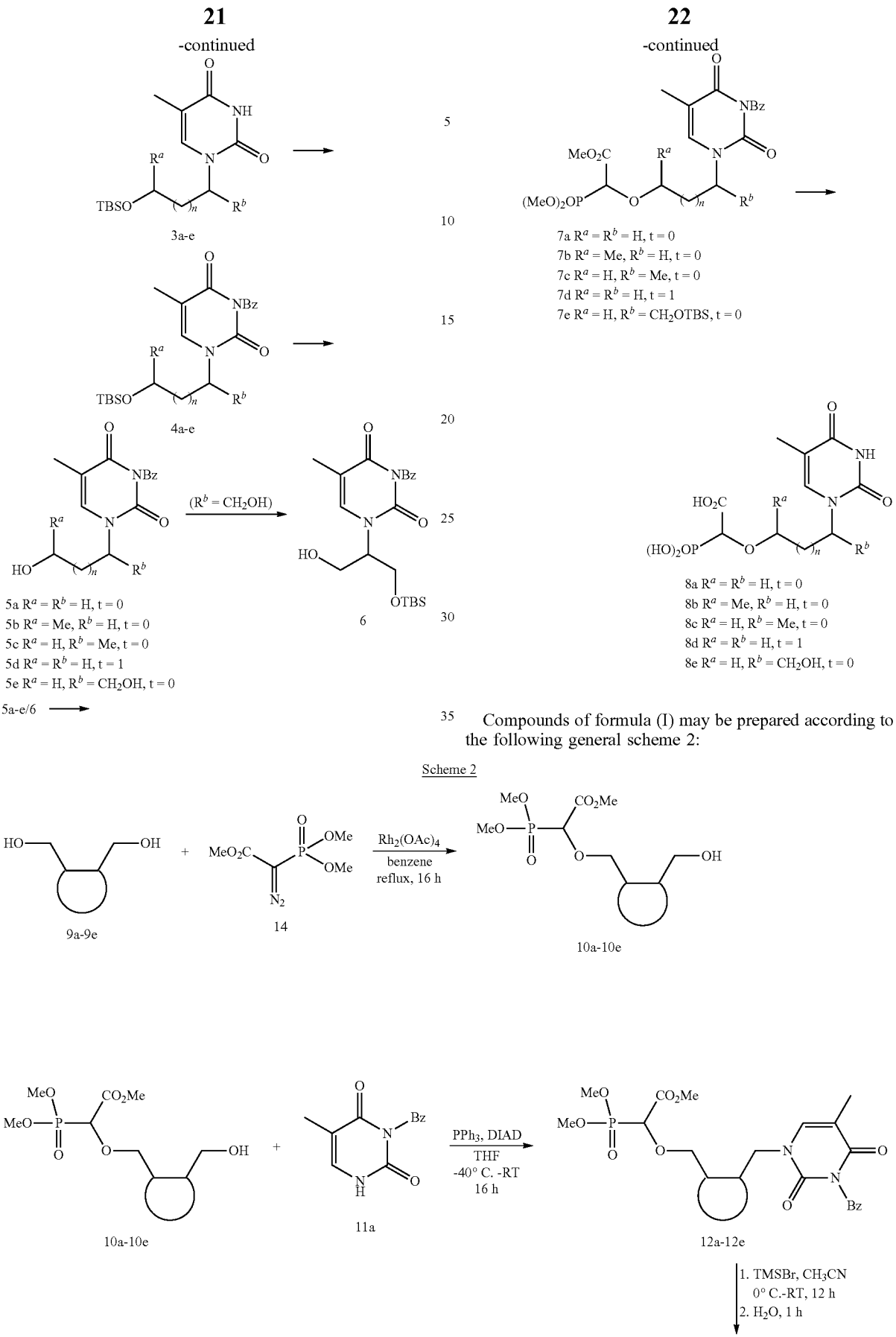
Compounds of formula (I) may be prepared according to the following general scheme 2:

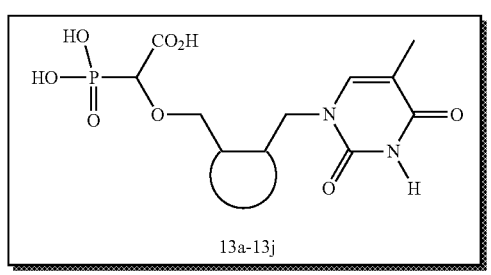
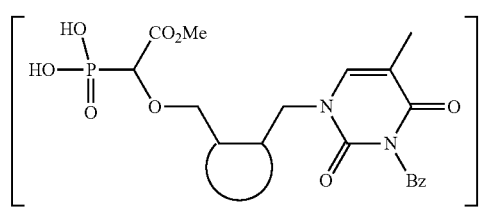
Compounds of formula (I) may be prepared according to the following general scheme 3.
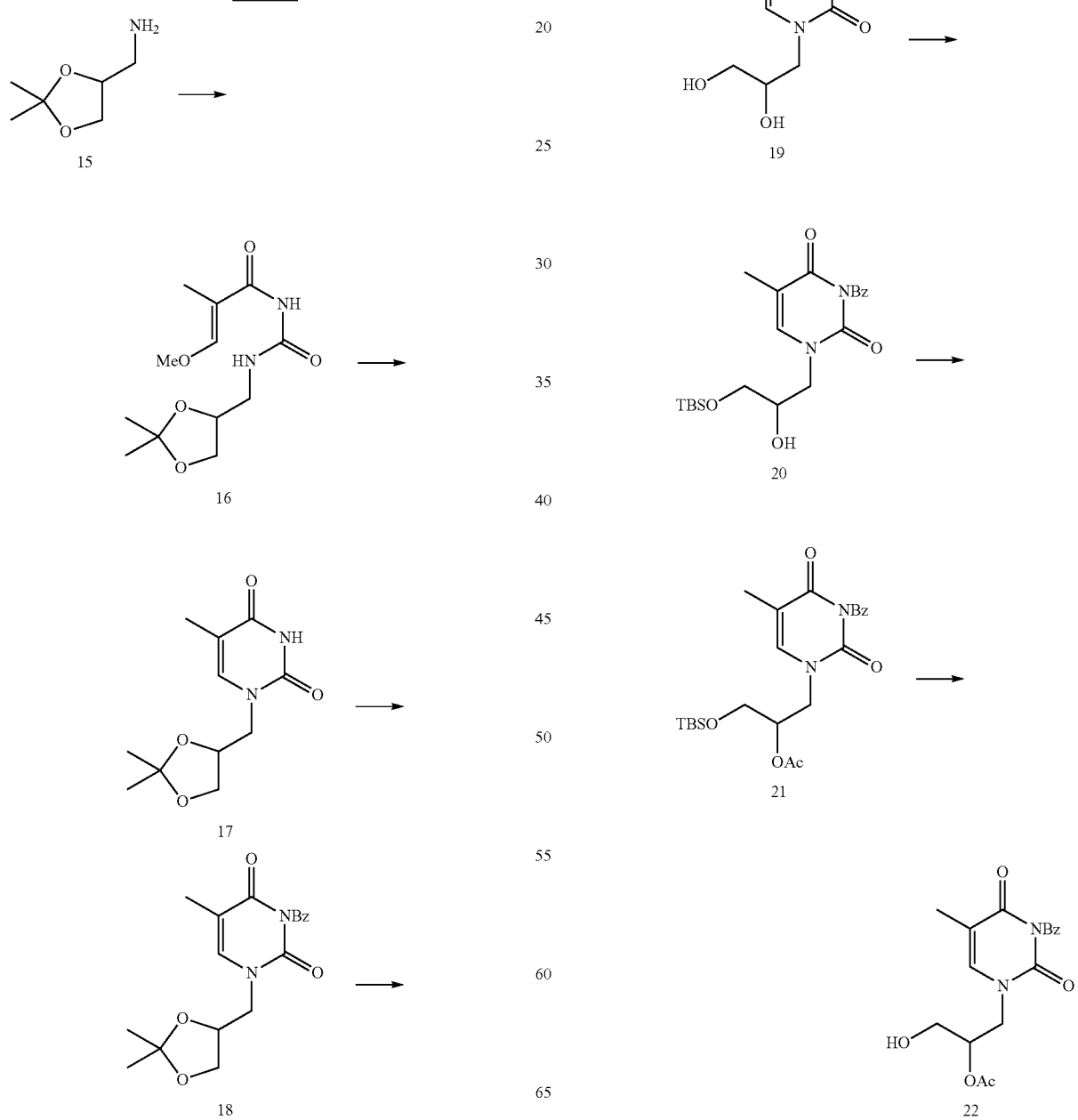

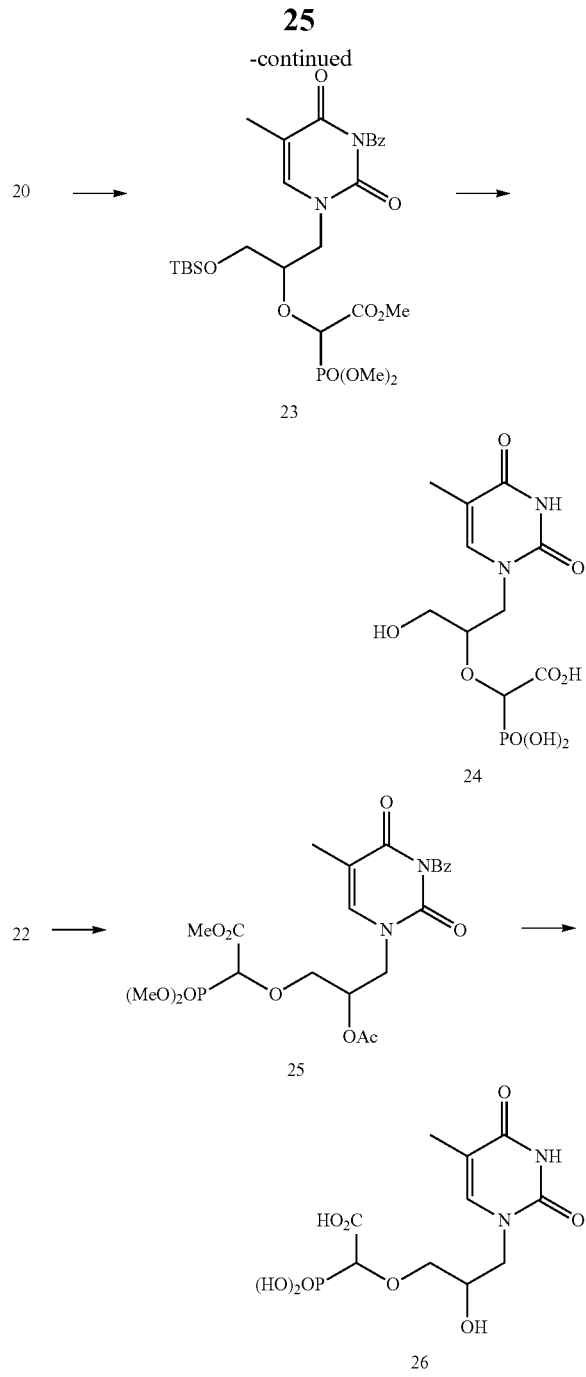

reduced pressure and the residue was dissolved in benzene (15 mL) and the resulting solution was added dropwise to a suspension of silver cyanate (2.57 g, 17.2 mmol) in benzene (10 mL). The mixture was heated to reflux temperature for 90 min and allowed to cool and settle. The supernatant solution was withdrawn by syringe and added dropwise to an ice-cooled solution of 2-((tert-butyldimethylsilyl)oxy) ethylamine 1a (0.75 g, 4.3 mmol) in THF (10 mL). After stirring overnight the solvents were removed under reduced pressure and the residue was purified by flash chromatography (40% EtOAc/hexanes) to afford a colourless solid (0.95 g, 70%). $\delta_H$ (400 MHz, CDCl$_3$) 0.07 (6H, s), 0.90 (9H, s), 1.77 (3H, br. s), 3.43 (2H, q, J=5.6), 3.72 (2H, t, J=5.6), 3.86 (3H, S), 7.32 (1H, br. s), 7.70 (1H, br. s), 8.80 (1H, br. unresolved t); $\delta_C$ (75 MHz, CDCl$_3$) −5.5, 8.8, 18.2, 25.8, 42.0, 61.2, 61.7, 107.6, 154.9, 158.1, 169.4; m/z (ES+) 317.3 (M+H); HRMS (ES+): calc. for C$_{14}$H$_{29}$N$_2$O$_4$Si (M+H): 317.1897 found: 317.1888.

N-((2-((tert-Butyldimethylsilyl)oxy)propyl)carbamoyl)-3-methoxy-2-methylacrylamide 2b This was prepared according to the procedure described for 2a, starting from 3-methoxy-2-methylacrylic acid (1.0 g, 8.59 mmol), oxalyl chloride (0.8 mL, 1.12 g, 9.45 mmol), AgOCN (2.57 g, 17.2 mmol), and amine 1b (0.81 g 4.3 mmol). Yield 1.05 g (74%) colourless solid. $\delta_H$ (400 MHz, CDCl$_3$) 0.06 (6H, s), 0.90 (9H, s), 1.15 (3H d, J=6.2), 1.77 (3H, d, J=1.1), 3.19 (1H, ddd, J=13.3, 6.7, 5.8), 3.36 (1H, ddd, J=13.3, 6.1, 4.3), 3.86 (3H, s), 3.91-4.00 (1H, m), 7.34 (1H, unresolved q, J~1.1), 8.1 (1H, br. s), 8.83 (1H, unresolved t, J~5.2); $\delta_C$ (100 MHz, CDCl$_3$) −4.9, −4.7, 8.8, 18.0, 21.3, 25.7, 25.8, 47.2, 61.3, 67.2, 107.4, 154.7, 158.1, 169.1; m/z (ES+) 331.3 (M+H); HRMS (ES+): calc. for C$_{15}$H$_{31}$N$_2$O$_4$Si (M+H): 331.2053, found: 331.2052.

N-((1-((tert-Butyldimethylsilyl)oxy)-2-propyl)carbamoyl)-3-methoxy-2-methylacrylamide 2c This was prepared according to the procedure described for 2a, starting from 3-methoxy-2-methylacrylic acid (1.0 g, 8.59 mmol), oxalyl chloride (0.8 mL, 1.12 g, 9.45 mmol), AgOCN (2.57 g, 17.2 mmol), and amine 1c (0.81 g, 4.3 mmol). Yield 0.9 g (63%) white solid. $\delta_H$ (400 MHz, CDCl$_3$) 0.05 (s, 3H), 0.06 (s, 3H), 0.90 (s, 9H), 1.21 (d, J=6.7, 3H), 1.77 (s with unresolved splitting, 3H), 3.60 (apparent qd, J=9.9, 4.7, 2H), 3.85 (s, 3H), 3.94-4.05 (m, 1H), 7.34 (unresolved q, J~1, 1 H), 8.04 (br s, 1H), 8.71 (d, J=7.9, 1H); $\delta_C$ (100 MHz, CDCl$_3$) −5.7, −5.5, 8.8, 17.4, 18.2, 25.8, 47.3, 61.2, 66.0, 107.8, 154.2, 157.9, 169.5; MS (ES+): m/z 331.3 (M+H); HRMS (ES+): calc. for C$_{15}$H$_{31}$N$_2$O$_4$Si (M+H) 331.2053, found 331.2048.

N-((3-((tert-Butyldimethylsilyl)oxy)propyl)carbamoyl)-3-methoxy-2-methylacrylamide 2d This was prepared according to the procedure described for 2a, starting from 3-methoxy-2-methylacrylic acid (0.81 g, 7.0 mmol), oxalyl chloride (0.66 mL, 0.98 g, 7.7 mmol), AgOCN (1.2 g, 8.01 mmol), and amine 1d (0.81 g, 4.3 mmol). Yield 0.99 g (70%) white solid. $\delta_H$ (400 MHz, CDCl$_3$) 0.05 (6H, s), 0.89 (9H, s), 1.73-1.82 (5H, m), 3.34-3.43 (2H, m), 3.68 (2H, t, J=6) 3.86 (3H, s), 7.34 (1H, unresolved q, J~1.1), 8.06 (1H, br. s), 8.69 (1H, unresolved t, J~4.9); $\delta_C$ (100 MHz, CDCl$_3$) −5.4, 8.7, 18.3, 25.9, 32.4, The present invention is further described by way of the following non-limiting examples.

EXAMPLES

The following compounds where prepared according to general scheme 1 described above:

N-((2-((tert-Butyldimethylsilyl)oxy)ethyl)carbamoyl)-3-methoxy-2-methylacrylamide 2a A solution of 3-methoxy-2-methylacrylic acid (1.0 g, 8.59 mmol) in CH$_2$Cl$_2$ (15 mL) was treated dropwise with oxalyl chloride (0.8 mL, 1.12 g, 9.45 mmol) and stirred at ambient temperature for 1 h. The volatiles were removed under 36.7, 60.5, 61.3, 107.7, 154.8, 158.1, 169.5; m/z (ES+) 331.3 (M+H) HRMS (ES+): calc. for $C_{15}H_{31}N_2O_4Si$ (M+H): 331.2053, found: 331.2041.

N-((1,3-bis-((tert-Butyldimethylsilyl)oxy)-2-propyl) carbamoyl)-3-methoxy-2-methylacrylamide 2e This was prepared according to the procedure described for 2a, starting from 3-methoxy-2-methylacrylic acid (1.0 g, 8.59 mmol), oxalyl chloride (0.8 mL, 1.12 g, 9.45 mmol), AgOCN (2.57 g, 17.2 mmol), and amine 1e (1.60 g, 5.0 mmol). Yield 1.1 g (48%) white solid. $\delta_H$ (400 MHz, CDCl$_3$) 0.06 (2×s, 12H), 0.90 (3, 18H), 1.76 (unresolved d, J~1, 3H), 3.64 (dd, J=9.6, 6.3, 2H), 3.76 (dd, J=9.6, 3.8, 2H), 3.85 (s, 3H), 3.90-3.99 (m, 1H), 7.33 (unresolved q, J~1, 1 H), 7.88 (br s, 1H), 8.85 (br d, J=8.6, 1H); $\delta_C$ (100 MHz, CDCl$_3$) −5.5, 8.8, 18.2, 25.9, 52.6, 60.7, 61.3, 107.7, 154.4, 158.0, 169.1; MS (ES+): m/z 461.3 (M+H); HRMS (ES+): calc. for $C_{21}H_{45}N_2O_5Si_2$ (M+H) 461.2867, found 461.2858.

1-(2-((tert-Butyldimethylsilyl)oxy)ethyl)-5-methyl-pyrimidine-2,4(1H,3H)-dione 3a Concentrated ammonia (2.5 mL) was added to a solution of the acylurea 2a (0.50 g, 1.58 mmol) in EtOH (2.5 mL). The mixture was sealed and placed in a pre-equilibrated oil bath at 100° C. and stirred for 24 h, after which it was concentrated under reduced pressure to afford the thymine derivative 3a as a bone-white solid (0.45 g, ~quantitative) which was carried forward without purification. $\delta_H$ (400 MHz, CDCl$_3$) 0.01 (6H, s), 0.87 (9H, s), 1.90 (3H, d, J=1.1), 3.82 (4H, s), 7.1 (1H, unresolved q, J~1.1) 8.3 (1H, br. s); $\delta_C$ (100 MHz, CDCl$_3$) −5.6, 12.1, 18.0, 25.7, 50.6, 61.0, 109.2, 142.6, 150.9, 164.5; m/z (ES+) 285.3 (M+H); HRMS (ES+) calc. for $C_{13}H_{25}N_2O_3Si$ (M+H): 285.1634, found: 285.1626.

1-(2-((tert-Butyldimethylsilyl)oxy)propyl)-5-methyl-pyrimidine-2,4(1H,3H)-dione 3b Concentrated ammonia (2.5 mL) was added to a solution of the acylurea 2b (0.50 g, 1.51 mmol) in EtOH (2.5 mL). The mixture was sealed and irradiated for 3 h (100° C., 200 W), after which it was concentrated under reduced pressure to afford the thymine derivative 3b as a bone-white solid (0.45 g, ~quantitative) which was carried forward without purification. $\delta_H$ (400 MHz, CDCl$_3$) −0.10 (3H, s), 0.02 (3H, s), 0.85 (9H, s), 1.17 (3H, d, J=6.2), 1.89 (3H, d, J=1.2), 3.20 (1H, dd, J=13.7, 8.8), 4.01 (1H, dd, J=13.7, 2.7), 4.10 (1H, dtd, J=8.8, 6.2, 2.7), 7.06 (1H, unresolved q, J~1.2); $\delta_C$ (100 MHz, CDCl$_3$) −5.3, −4.7, 12.1, 17.8, 21.1, 25.6, 55.8, 66.5, 109.1, 142.9, 151.0, 164.4; m/z (ES+) 299.3 (M+H); HRMS (ES+) calc. for $C_{14}H_{27}N_2O_3Si$ (M+H): 299.1791, found: 299.1790.

1-(1-((tert-Butyldimethylsilyl)oxy)-2-propyl)-5-methylpyrimidine-2,4(1H,3H)-dione 3c This was prepared according to the procedure described for 3b, starting from 2c (0.387 g, 1.17 mmol). Yield 0.338 g (98%). $\delta_H$ (400 MHz, CDCl$_3$+CD$_3$OD) 0.03 (3H, s), 0.05 (3H, s), 0.89 (9H, s), 1.38 (2H, d, J=7.1), 1.91 (3H, d, J=1.1), 3.72-3.81 (2H, m), 4.66-4.77 (1H, m), 7.35 (1H, unresolved q, J 1.1); $\delta_C$ (100 MHz, CDCl$_3$+CD$_3$OD) −5.5, −5.4, 12.5, 15.6, 18.5, 26.0, 53.0, 65.2, 110.0, 139.6, 152.1, 165.5; m/z (ES+) 299.2 (M+H).

1-(3-((tert-Butyldimethylsilyl)oxy)propyl)-5-methyl-pyrimidine-2,4(1H,3H)-dione 3d This was prepared according to the procedure described for 3b, starting from 2d (0.50 g, 1.51 mmol). Yield 0.45 g (~quantitative). $\delta_H$ (300 MHz, CDCl$_3$) 0.06 (6H, s), 0.91 (9H, s), 1.83-1.94 (2H, m), 1.91 (3H, d, J=1.2), 3.65 (2H, t, J=5.7), 3.79-3.86 (2H, m), 7.06 (1H, unresolved q, J~1.2); $\delta_C$ (100 MHz, CDCl$_3$) −5.5, 12.2, 18.2, 25.8, 31.4, 45.8, 59.1, 110.0, 141.4, 151.0, 164.5; m/z (ES+) 299.3 (M+H); HRMS (ES+) calc. for $C_{14}H_{27}N_2O_3Si$ (M+H): 299.1791, found: 299.1788.

1-(1,3-bis-((tert-Butyldimethylsilyl)oxy)-2-propyl)-5-methylpyrimidine-2,4(1H,3H)-dione 3e This was prepared according to the procedure described for 3b, starting from 2e (0.50 g, 1.09 mmol). Yield 0.45 g (97%). $\delta_H$ (400 MHz, CDCl$_3$) 0.04 (6H, s), 0.05 (6H, s), 0.87 (18H, s), 1.90 (3H, s), 3.88 (4H, apparent qd, J=10.7, 5.4) 4.60 (1H, quint, J=5.4); $\delta_C$ (100 MHz, CDCl$_3$) −5.7, −5.6, 12.3, 18.1, 25.7, 57.6, 60.7, 109.0, 139.8, 151.3, 163.8; MS (ES+): m/z 429.3 (M+H); HRMS (ES+): calc. for $C_{20}H_{41}N_2O_5Si_2$ (M+H) 429.2605, found 429.2589.

3-Benzoyl-1-(2-((tert-butyldimethylsilyl)oxy)ethyl)-5-methylpyrimidine-2,4(1H,3H)-dione 4a A solution of the thymine derivative 3a (0.30 g, 1.06 mmol), DMAP (26 mg, 0.21 mmol), diisopropylethylamine (0.4 mL) and benzoyl chloride (0.2 mL) in CH$_2$Cl$_2$ (4 mL) was irradiated for 30 min (75° C., 200 W). An equal volume of sat. NaHCO$_3$ was added and the mixture was stirred vigorously for 1 h and then partitioned with CH$_2$Cl$_2$ (20 mL) and sat. NaHCO$_3$ (20 mL). The Organic layer was washed with sat. NaHCO$_3$ (20 mL) then 2M HCl (20 mL), dried with MgSO$_4$ and concentrated under reduced pressure. The residue was purified by flash chromatography (30% EtOAc/Hexanes) to afford the desired product as a viscous, slightly yellow oil (0.30 g, 73%). $\delta_H$ (400 MHz, CDCl$_3$) 0.06 (6H, s), 0.90 (9H, s), 1.93 (3H, unresolved d, J~1), 3.78-3.88 (4H, m), 7.22 (1H, unresolved q, J~1), 7.43-7.51 (2H, m), 7.58-7.66 (1H m), 7.87-7.94 (2H, m); $\delta_C$ (75 MHz, CDCl$_3$) −5.6, 12.0, 18.0, 25.6, 50.8, 60.8, 109.0, 129.0, 130.3, 131.6, 134.8, 142.3, 149.7, 163.2, 169.0; m/z (ES+) 389.3 (M+H); HRMS (ES+) calc. for $C_{20}H_{29}N_2O_4Si$: 389.1897 found: 389.1888.

3-Benzoyl-1-(2-((tert-butyldimethylsilyl)oxy)propyl)-5-methylpyrimidine-2,4(1H,3H)-dione 4b This was prepared according to the procedure described for 4a, starting from compound 3b (0.40 g, 1.34 mmol), DMAP (35 mg, 0.29 mmol), diisopropylethylamine (0.50 mL, 0.37 g, 2.87 mmol), and benzoyl chloride (0.25 mL, 0.30 g, 2.15 mmol). Yield 0.34 g (62%). $\delta_H$ (400 MHz, CDCl$_3$); 0.02 (3H, s), 0.07 (3H, s), 0.90 (9H, s), 1.17 (3H, d, J=6.2), 1.94 (3H, d, J=1.1), 3.26 (1H, dd, J=13.7, 8.7), 4.05 (1H, dd, J=13.7, 2.6), 4.12 (1H, dtd, J=8.7, 6.2, 2.6), 7.18 (1H, unresolved q, J~1.1), 7.44-7.52 (2H, m), 7.60-7.67 (1H, m), 7.90-7.95 (2H, m); $\delta_C$ (100 MHz, CDCl$_3$) −5.1, −4.6, 12.1, 17.8, 21.1, 25.6, 56.0, 66.5, 109.1, 129.0, 130.3, 131.8, 134.8, 142.6, 149.9, 163.3, 169.0 m/z (ES+) 403.3 (M+H); HRMS (ES+) calc. for $C_{21}H_{31}N_2O_4Si$: 403.3053, found: 403.2046.

3-Benzoyl-1-(1-((tert-butyldimethylsilyl)oxy)-2-propyl)-5-methylpyrimidine-2,4(1H,3H)-dione 4c This was prepared according to the procedure described for 4a, starting from compound 3c (0.32 g, 1.07 mmol), DMAP (26 mg, 0.21 mmol), diisopropylethylamine (0.4 mL, 0.3 g, 2.3 mmol), and benzoyl chloride (0.2 mL, 0.24 g, 1.72 mmol). The crude product was recrystallised from methanol, yield 0.19 g (44%). $\delta_H$ (400 MHz, CDCl$_3$) 0.05 (3H, s), 0.07 (3H, s), 0.91 (9H, s), 1.39 (3H, d, J=7.1), 1.94 (3H, s), 3.72 (1H, dd, J=10.9, 4.6), 3.80 (1H, dd, J=10.9, 3.3), 4.67-4.80 (1H, m), 7.34 (1H, s), 7.43-7.51 (2H, m), 7.58-7.66 (1H, m), 7.86-7.96 (2H, m); $\delta_C$ (100 MHz, CDCl$_3$) −5.7, −5.6, 12.4, 15.3, 18.1, 25.7, 52.5, 64.7, 109.4, 129.0, 130.3, 131.8, 134.8, 138.3, 150.0, 162.8, 169.2; m/z (ES+) 403.2 (M+H).

3-Benzoyl-1-(3-((tert-butyldimethylsilyl)oxy)propyl)-5-methylpyrimidine-2,4(1H,3H)-dione 4d This was prepared according to the procedure described for 4a, starting from compound 3d (0.40 g, 1.34 mmol), DMAP (35 mg, 0.29 mmol), diisopropylethylamine (0.50 mL, 0.37 g, 2.87 mmol), and benzoyl chloride (0.25 mL, 0.30 g, 2.15 mmol). Yield 0.43 g (80%). $\delta_H$ (400 MHz, CDCl$_3$) 0.07 (6H, s), 0.91 (9H, s), 1.85-1.96 (2H, m), 1.93 (3H, s), 3.66 (2H, t, J=5.7), 3.85 (2H, t, J=6.7), 7.17 (1H, s), 7.44-7.50 (2H, m), 7.59-7.65 (1H, m), 7.87-7.93 (2H, m); $\delta_C$ (100 MHz, CDCl$_3$) −5.5, 12.3, 18.2, 25.8, 31.1, 46.2, 59.1, 110.0, 129.0, 130.3, 131.7, 134.8, 141.1, 149.7, 163.2, 169.1; m/z (ES+) 403.3 (M+H); HRMS (ES+) calc. for C$_{21}$H$_{31}$N$_2$O$_4$Si: 403.3053, found: 403.2051.

3-Benzoyl-1-(1,3-bis-((tert-butyldimethylsilyl)oxy)-2-propyl)-5-methylpyrimidine-2,4(1H,3H)-dione 4e This was prepared according to the procedure described for 4a, starting from compound 3e (0.35 g, 0.816 mmol), DMAP (20 mg, 0.16 mmol), diisopropylethylamine (0.30 mL, 0.22 g, 1.72 mmol), and benzoyl chloride (0.14 mL, 0.17 g, 1.20 mmol). Yield 0.26 g (77%). $\delta_C$ (400 MHz, CDCl$_3$) 0.07 (6H, s), 0.08 (6H, s), 0.90 (18H, s), 1.94 (3H, s), 3.91 (4H, apparent qd, J=10.8, 5.4), 4.54 (1H, quint, J=5.4), 7.34 (1H, s), 7.36-7.42 (2H, m), 7.51-7.56 (1H, m), 7.81-7.86 (2H, m); $\delta_C$ (100 MHz, CDCl$_3$) −5.7, −5.6, 12.3, 18.0, 25.7, 58.0, 60.7, 109.0, 129.0, 130.3, 131.7, 134.7, 139.5, 150.2, 162.7, 169.0; MS (ES+): m/z 533.2 (M+H); HRMS (ES+): calc. for C$_{27}$H$_{44}$N$_2$O$_5$Si$_2$ (M+H) 533.2867, found 533.2867.

3-Benzoyl-1-(2-hydroxyethyl)-5-methylpyrimidine-2,4(1H,3H)-dione 5a

A solution of TBAF (1 M in THF, 1.0 mL, 1 mmol) was added to an ice-cooled, stirring solution of the TBS derivative 4a (0.30 g, 0.77 mmol) in THF (5 mL). After stirring for 2 h the mixture was partitioned with CH$_2$Cl$_2$ (20 mL) and 2 M HCl (20 mL). The layers were separated and the aqueous phase was extracted with CH$_2$Cl$_2$ (20 mL). The combined organic extracts were washed with brine (20 mL), dried over MgSO$_4$ and concentrated. The residue was purified by flash chromatography (neat EtOAc) to afford the desired product (88 mg, 40% yield). $\delta_H$ (400 MHz, CDCl$_3$+10% CD$_3$OD) 1.93 (3H, s), 3.69-6.90 (4H, m), 7.32 (1H, s), 7.44-7.56 (2H, m), 7.60-7.72 (1H, m), 7.85-7.95; $\delta_C$ (100 MHz, CDCl$_3$+ 10% CD$_3$OD) 12.1, 51.1, 59.7, 109.8, 129.2, 130.4, 131.4, 135.2, 142.3, 150.1, 163.7, 169.3; m/z (ES+) 297.2 (M+Na); HRMS (ES+) calc. for C$_{14}$H$_{15}$N$_2$O$_4$(M+H) 275.1032, found 275.1025; HRMS (ES+) calc. for C$_{14}$H$_{14}$N$_2$O$_4$Na (M+Na) 297.0851, found 297.0859.

3-Benzoyl-1-(2-hydroxypropyl)-5-methylpyrimidine-2,4(1H,3H)-dione 5b

This was prepared according to the procedure described for 5a, starting from compound 4b (0.309 g, 0.77 mmol) and TBAF (1M, 1.0 mL, 1 mmol). Yield 0.207 g (93%). $\delta_H$ (400 MHz, CDCl$_3$) 1.56 (3H, d, J=6.3), 1.91 (3H, d, J=1.0) 2.72 (1H, br. s), 3.44 (1H, dd, J=14.1, 8.3), 3.89 (1H, dd, J=14.1, 2.8), 4.03 (1H, dtd, J=8.3, 6.3, 2.8), 7.25 (1H, unresolved q, J~1), 7.44-7.51 (2H, m), 7.60-7.67 (2H, m), 7.88-7.94; $\delta_C$ (100 MHz, CDCl$_3$) 12.2, 20.7, 55.1, 66.1, 109.7, 129.1, 130.3, 131.5, 135.0, 142.0, 150.2, 163.3, 169.1; m/z (ES+) 289.3 (M+H); HRMS (ES+) calc. for C$_{15}$H$_{16}$N$_2$O$_4$ (M+H) 289.1188, found 289.1189.

3-Benzoyl-1-(1-hydroxy-2-propyl)-5-methylpyrimidine-2,4(1H,3H)-dione 5c

This was prepared according to the procedure described for 5a, starting from compound 4c (0.187 g, 0.465 mmol) and TBAF (1M, 0.7 mL, 0.7 mmol). Yield 0.130 g (97%). $\delta_H$ (400 MHz, CDCl$_3$) 1.32 (3H, d, J=7.1), 1.93 (3H, s), 2.81 (1H, t, J=5.2), 3.57-3.78 (2H, m), 4.59-4.72 (1H, m), 7.26 (1H, s), 7.45-7.51 (2H, m), 7.60-7.67 (1H, m), 7.89-7.95 (2H, m); $\delta_C$ (100 MHz, CDCl$_3$) 12.5, 15.2, 53.4, 64.3, 110.4, 129.1, 130.3, 131.5, 135.0, 137.7, 150.4, 162.8, 169.2; m/z (ES+) 289.2 (M+H).

3-Benzoyl-1-(3-hydroxypropyl)-5-methylpyrimidine-2,4(1H,3H)-dione 5d

This was prepared according to the procedure described for 5a, starting from compound 4d (0.34 g, 0.84 mmol) and TBAF (1M, 1.0 mL, 1 mmol). Yield 0.22 g (91%). $\delta_H$ (400 MHz, CDCl$_3$) 1.88-1.96 (2H, m), 1.97 (3H, d, J=1.2), 2.25 (1H, unresolved t, J~4.6), 3.63-3.71 (2H, m), 3.92 (2H, t, J=6.4), 7.14 (1H, unresolved q, J~1.2) 7.46-7.53 (2H, m), 7.62-7.68 (2H, m), 7.88-7.95 (2H, m); $\delta_C$ (100 MHz, CDCl$_3$) 12.6, 31.3, 45.5, 58.3, 110.9, 129.1, 130.3, 131.5, 135.0, 140.5, 150.4, 163.1, 168.9 m/z (ES+) 289.3 (M+H).

3-Benzoyl-1-(1,3-dihydroxy-2-propyl)-5-methylpyrimidine-2,4(1H,3H)-dione 5e

This was prepared according to the procedure described for 5a, starting from compound 4e (0.309 g, 0.77 mmol) and TBAF (1M, 1.0 mL, 1 mmol). Yield 0.207 g (93%). $\delta_H$ (400 MHz, CD$_3$OD) 1.85 (3H, d, J=1.1), 3.73 (2H, dd, J=11.9, 4.9), 3.80 (2H, dd, J=11.9, 7.4), 4.50 (1H, tt, J=7.4, 4.9), 7.42-7.49 (2H, m), 7.58-7.65 (2H, m), 7.85-7.90 (2H, m); $\delta_C$ (100 MHz, CH$_3$OD) 12.4, 60.7, 61.7, 110.7, 130.4, 131.5, 133.1, 136.3, 141.5, 152.2, 164.9, 170.5; m/z (ES+) 305.2 (M+H).

3-Benzoyl-1-(1-((tert-butyldimethylsilyl)oxy)-3-hydroxypropan-2-yl)-5-methylpyrimidine-2,4(1H, 3H)-dione 6

A solution of diol 5e (0.208 g, 0.68 mmol) and imidazole (0.113 g, 1.66 mmol) in dimethylformamide (4 mL) was cooled in ice and treated with tert-butyldimethylsilyl chloride (0.113 g, 0.75 mmol). The mixture was stirred and allowed to warm to room temperature overnight, then partitioned with Et$_2$O and saturated NH$_4$Cl. The organic phase was separated and the aqueous phase was extracted once with Et$_2$O. The combined organic phases were washed twice with saturated LiCl, dried with MgSO$_4$ and concentrated. The residue was purified by flash chromatography (50% EtOAc/hexanes) to afford the mono-TBS ether 6 as a white solid (0.09 g, 32%). δ$_H$ (400 MHz, CDCl$_3$) 0.09 (6H, s), 0.92 (9H, s), 1.96 (3H, s), 2.30 (1H, br s), 3.90-4.10 (4H, m), 4.50-4.58 (1H, m), 7.45-7.54 (3H, m), 7.61-7.68 (1H, m), 7.89-7.96 (2H, m); δ$_C$ (100 MHz, CDCl$_3$) −5.7, −5.65, 12.4, 18.0, 25.6, 59.1, 61.2, 61.7, 109.7, 129.1, 130.4, 131.6, 134.9, 139.7, 150.6, 162.8, 169.0; m/z (ES+) 419.2 (M+H).

Methyl 2-(2-(3-benzoyl-5-methyl-2,4-dioxo-3,4-dihydropyrimidin-1(2H)-yl)ethoxy)-2-(dimethoxyphosphoryl)acetate 7a A Mixture of the alcohol 5a (86 mg, 0.32 mmol) and trimethyl phosphonodiazoacetate (141 mg, 0.68 mmol) in benzene (10 mL) was degassed by purging with nitrogen gas for 10 minutes. The mixture was briefly warmed to effect complete solution, and active molecular sieve beads (ca 1 mL) were added. The mixture was stirred for 1 h at ambient temperature, after which Rh$_2$(OAc)$_4$ (3 mg, 6.2 μmol) was added, and the mixture was placed in a pre-equilibrated bath at 90° C. and stirred overnight. The cooled solution was decanted from the sieve beads, concentrated and the residue was purified by flash chromatography (2% MeOH/EtOAc) to afford the desired product as a colourless oil (79 mg, 54%). δ$_H$ (400 MHz, CDCl$_3$) 1.96 (3H, d, J=1.2), 3.79-4.07 (13H, m), 4.38 (1H, d, J=18.9), 7.35 (1H, unresolved q, J~1.2), 7.46-7.52 (2H, m), 7.61-7.66 (1H, m), 7.96-8.02 (2H, m); δ$_C$ (100 MHz, CDCl$_3$) 12.2, 48.4, 53.0, 54.0 (d, J=16.8), 54.1 (d, J=16.7), 70.3 (d, J=11.9), 76.1 (d, J=158.7), 109.7, 129.1, 130.6, 131.7, 134.9, 141.9, 149.9, 163.3, 167.1 (d, J=1.8), 169.1; δ$_P$ (162 MHz, CDCl$_3$) 16.1; m/z (ES−) 453.1 (M−H); HRMS (ES+) calc. for C$_{19}$H$_{24}$N$_2$O$_9$P (M+H) 455.1219, found 455.1214.

An unknown side-product (~20 mol %) was evident in the $^1$H NMR spectrum (δ$_H$ 5.23, dd, J=17.3, 10.5).

Methyl 2-((1-(3-benzoyl-5-methyl-2,4-dioxo-3,4-dihydropyrimidin-1(2H)-yl)propan-2-yl)oxy)-2-(dimethoxyphosphoryl)acetate 7b This was prepared according to the procedure described for 7a, starting from 5b (167 mg, 0.58 mmol), trimethyl phosphonodiazoacetate (133 mg, 0.64 mmol), and Rh$_2$(OAc)$_4$ (3 mg, 6.2 μmol). Yield 160 mg (59%). δ$_H$ (400 MHz, CDCl$_3$) 1.21 (3H, d, J=6.2), 1.22 (3H, d, J=6.3), 1.95 (3H, d, J=1.1), 1.96 (3H, d, J=1.1), 3.44 (1H, dd, J=14.3, 9.0), 3.59 (1H, dd, J=14.3, 7.9), 3.77-3.99 (20H, m), 4.03 (1H, dd, J=14.3, 2.6), 4.11 (1H, dd, J=14.3, 2.1), 4.33 (1H, d, J=18.4), 4.48 (1H, d, J=20.3), 7.28 (1H, unresolved q, J~1.1), 7.42 (1H, unresolved q, J~1.1), 7.44-7.57 (4H, m), 7.60-7.66 (2H, m), 7.95-7.99 (2H, m), 8.05-8.10 (2H, m); δ$_C$ (100 MHz, CDCl$_3$) 12.1, 12.15, 15.8, 16.9, 52.8, 52.9, 53.5, 53.6 (d, J=6.6), 53.89 (d, J=6.6), 53.92 (d, J=6.6), 54.0 (d, J=6.6), 73.2 (d, J=160.2), 74.6 (d, J=159.0), 75.2 (d, J=13.8), 77.5 (d, J=8.2), 109.2, 109.6, 128.9, 129.0, 130.4, 130.6, 131.6, 134.7, 134.8, 142.2, 142.3, 150.0, 150.1, 163.2, 163.4, 167.3 (d, J=1.0), 167.6 (d, J=3.3), 169.0, 169.2; δ$_P$ (162 MHz, CDCl$_3$) 16.1, 17.1; m/z (ES+) 469.3 (M+H); HRMS (ES+) calc. for C$_{20}$H$_{26}$N$_2$O$_3$P (M+H) 469.1372, found 469.1372.

Methyl 2-(2-(3-benzoyl-5-methyl-2,4-dioxo-3,4-dihydropyrimidin-1(2H)-yl)propoxy)-2-(dimethoxyphosphoryl)acetate 7c This was prepared according to the procedure described for 7a, starting from 5c (130 mg, 0.45 mmol), trimethyl phosphonodiazoacetate (103 mg, 0.50 mmol), and Rh$_2$(OAc)$_4$ (2.2 mg, 4.5 μmol). Yield 90 mg (33%). δ$_H$ (400 MHz, CDCl$_3$) 1.47 (3H, d, J=7), 1.49 (3H, d, J=7), 1.98 (3H, s), 1.99 (3H, s), 3.75-3.92 (22H, m), 4.36 (1H, d, J=18.4), 4.37 (1H, d, J=19.1), 4.79-4.90 (2H, m), 7.39 (1H, s), 7.43-7.52 (5H, m), 7.60-7.67 (2H, m), 7.94-8.02 (4H, m); δ$_C$ (100 MHz, CDCl$_3$) 12.5, 15.5, 15.6, 51.4, 51.5, 52.9, 54.0, 54.05, 54.1, 54.15, 54.2, 73.5 (d, J=10.7), 76.6 (d, J=11.9), 75.98 (d, J=158.5), 76.04 (d, J=158.3), 110.0, 110.2, 129.1, 130.5, 131.7, 134.9, 138.1, 138.4, 150.0, 150.05, 162.8, 162.9, 167.0 (d, J=2.5), 167.05 (d, J=2.0), 169.3; δ$_P$ (162 MHz, CDCl$_3$) 15.3, 16.1; m/z (ES+) 469.3 (M+H).

Methyl 2-(3-(3-benzoyl-5-methyl-2,4-dioxo-3,4-dihydropyrimidin-1(2H)-yl)propoxy)-2-(dimethoxyphosphoryl)acetate 7d This was prepared according to the procedure described for 7a, starting from 5d (122 mg, 0.42 mmol), trimethyl phosphonodiazoacetate (104 mg, 0.50 mmol), and Rh$_2$(OAc)$_4$ (2.4 mg, 5 μmol). Yield 95 mg (48%). δ$_H$ (400 MHz, CDCl$_3$) 1.98 (3H, d, J=1.1), 2.02-2.11 (2H, m), 3.54-3.62 (1H, m), 3.70-3.77 (1H, m), 3.83-3.96 (11H, m), 4.33 (1H, d, J=19.4), 7.46-7.52 (3H, m), 7.60-7.67 (1H, m), 7.89-7.94 (2H, m); δ$_C$ (100 MHz, CDCl$_3$) 12.0, 28.3, 46.0, 52.8, 54.0 (d, J=11.0), 54.1 (d, J=11.0), 29.2 (d, J=12.2), 76.2 (d, J=159.5), 110.1, 129.0, 130.3, 131.7, 134.8, 141.7, 149.8, 163.3, 167.4 (d, J=1.8), 169.1; δ$_P$ (162 MHz, CDCl$_3$) 16.3; m/z (ES+) 469.2 (M+H); HRMS (ES+) calc. for C$_{20}$H$_{26}$N$_2$O$_9$P (M+H) 469.1376, found 469.1375.

Methyl 2-(2-(3-benzoyl-5-methyl-2,4-dioxo-3,4-dihydropyrimidin-1(2H)-yl)-3-((tert-butyldimethylsilyl)oxy)propoxy)-2-(dimethoxyphosphoryl)acetate 7e This was prepared according to the procedure described for 7a, starting from 6 (90 mg, 0.215 mmol), trimethyl phosphonodiazoacetate (60 mg, 0.28 mmol), and Rh$_2$(OAc)$_4$ (4 mg, 8.3 μmol). Yield 73 mg (57%). δ$_H$ (400 MHz, CDCl$_3$) 0.08 (12H, s), 0.09 (18H, s), 1.96 (3H, s), 1.97 (3H, s), 3.78-3.88 (20H, m), 3.92-4.02 (4H, m) 4.06-4.16 (2H, m), 4.39 (2H, br d, J=18.8), 4.69-4.80 (2H, m), 7.45-7.54 (6H, m), 7.60-7.66 (2H, m), 7.92-7.97 (4H, m); δ$_C$ (100 MHz, CDCl$_3$) −5.7, 12.3, 17.8, 25.6, 52.9, 53.9-54.2, 56.9, 57.0, 60.8, 61.2, 69.9, 70.0, 76.26 (d, J=158.9), 76.30 (d, J=158.2), 109.47, 109.51, 129.0, 130.4, 131.6, 134.8, 139.49, 139.52, 150.1, 150.2, 162.7, 166.9 (d, J=1.9), 167.0 (d, J=1.4), 169.0; δ$_P$ (162 MHz, CDCl$_3$) 15.8, 16.0; m/z (ES+) 495.2 (M+H).

2-(2-(5-Methyl-2,4-dioxo-3,4-dihydropyrimidin-1(2H)-yl)ethoxy)-2-phosphonoacetic acid 8a A solution of 7a (77 mg, 0.17 mmol) in CH$_2$Cl$_2$ (3 mL) was treated with TMSBr (90 μL, 104 mg, 0.68 mmol) and irradiated for 15 min (50° C., 50 W). The resulting mixture was quenched with 50% v/v aq. MeOH (1 mL), stirred for 10 min and evaporated under reduced pressure. The residue was dissolved in 1M NaOH (3 mL) and stirred overnight at ambient temperature, then diluted with 2 M HCl (15 mL), washed with CH$_2$Cl$_2$ (2×15 mL) and concentrated. The residue was purified by charcoal chromatography to afford the desired product as an off-white solid (43 mg). δ$_H$ (300 MHz, D$_2$O) 1.80 (3H, s), 3.64-3.55 (1H, m), 3.73-3.82 (1H, m), 3.84-3.95 (3H, m), 7.55 (1H, s); δ$_C$ (100 MHz, D$_2$O) 11.3, 47.9, 69.0 (d, J=12.0), 81.0 (d, J=140.1), 110.3, 144.0, 152.4, 167.1, 176.4; δ$_P$ (162 MHz, D$_2$O) 11.7; m/z (ES+) 309.2 (M+H); HRMS (ES+) calc. for C$_9$H$_{14}$N$_2$O$_8$P (M+H) 309.0488, found 309.0485.

2-((1-(5-Methyl-2,4-dioxo-3,4-dihydropyrimidin-1(2H)-yl)propan-2-yl)oxy)-2-phosphonoacetic acid 8b This was prepared according to the procedure described for 8a, starting from 7b (96 mg, 0.205 mmol), and TMSBr (108 µL, 125 mg, 0.82 mmol). Yield 48 mg. $\delta_H$ (300 MHz, D$_2$O) 1.07 (3H, d, J=5.8), 1.09 (3H, d, J=5.9), 1.76-1.80 (6H, m), 3.65-3.87 (6H, m), 3.94 (1H, d, J=18.3), 3.98 (1H, d, J=17.6), 7.51 (1H, unresolved q, J~1.1), 7.57 (1H, unresolved q, J~1.1); $\delta_C$ (75 MHz, D$_2$O) 11.3, 16.1, 16.8, 51.6, 52.6, 74.4 (d, J=10.2), 76.0 (d, J=10.6), 78.4 (d, J=142.3), 79.4 (d, J=141.8), 110.1, 110.3, 144.2, 144.3, 152.5, 152.6, 167.04, 176.0, 177.0; $\delta_P$ (121 MHz, D$_2$O) 12.2, 12.5; m/z (ES+) 323.2 (M+H); HRMS (ES+) calc. for C$_{10}$H$_{16}$N$_2$O$_8$P (M+H) 323.0644, found 323.0649.

2-(2-(5-Methyl-2,4-dioxo-3,4-dihydropyrimidin-1(2H)-yl)propoxy)-2-phosphonoacetic acid 8c This was prepared according to the procedure described for 8a, starting from 7c (82 mg, 0.175 mmol), and TMSBr (95 µL, 109 mg, 0.71 mmol). Yield 31 mg. $\delta_C$ (400 MHz, D$_2$O) 1.26 (3H, d, J=7.1), 1.29 (3H, d, J=7.0), 3.6-3.9 (4H, m), 4.09 (1H, d, J=18.7), 4.14 (1H, d, J=17.6), ~4.7-4.85 (m, partly obscured by solvent), 7.58 (1H, s), 7.62 (1H, s); $\delta_C$ (100 MHz, D$_2$O) 11.44, 11.46, 14.75, 14.76, 52.45, 52.50, 72.6 (d, J=8.3), 73.7 (d, J=9.9), 78.8 (d, J=135.6), 79.9 (d, J=135.4), 110.8, 111.0, 139.6, 139.8, 152.4, 152.7, 166.50, 166.53, 172.8; $\delta_P$ (162 MHz, D$_2$O) 11.7, 11.8; m/z (ES+) 323.2 (M+H).

2-(3-(5-Methyl-2,4-dioxo-3,4-dihydropyrimidin-1(2H)-yl)propoxy)-2-phosphonoacetic acid 8d This was prepared according to the procedure described for 8a, starting from 7d (86 mg, 0.18 mmol) and TMSBr (96 µL, 112 mg, 0.73 mmol). Yield 42 mg. $\delta_H$ (400 MHz, CDCl$_3$) 1.79 (3H, d, J=1), 1.89 (2H, m), 3.39 (1H, dt, J=9.9, 6.3), 3.56 (1H, dt, J=9.9, 6.0), 3.80 (2H, t, J=7.2) 3.86 (1H, d, J=17.7), 7.51 (1H, unresolved q, J~1); $\delta_C$ (100 MHz, CDCl$_3$) 11.2, 28.0, 46.0, 68.3 (d, J=12.3), 80.6 (d, J=141.6), 110.6, 143.7, 152.3, 167.1, 176.6; $\delta_P$ (162 MHz, CDCl$_3$) 12.2; m/z (ES+) 323.2 (M+H); HRMS (ES+) calc. for C$_{10}$H$_{16}$N$_2$O$_8$P (M+H) 323.0644, found 323.0655.

2-(3-hydroxy-2-(5-methyl-2,4-dioxo-3,4-dihydropyrimidin-1(2H)-yl)propoxy)-2-phosphonoacetic acid 8e This was prepared according to the procedure described for 8a, starting from 7e (70 mg, 0.117 mmol), and TMSBr (95 µL, 109 mg, 0.71 mmol). Yield 29 mg. $\delta_H$ (400 MHz, CDCl$_3$) 1.85 (3H, s), 3.64-3.94 (5H, m), 7.72 (s, 1H); $\delta_C$ (100 MHz, CDCl$_3$) 11.47, 11.50, 56.8, 57.0, 59.7, 59.8, 69.2, (d, J=8.0), 69.3 (d, J=8.9), 80.7 (d, J=142.5), 80.8, d, J=142.3), 110.87, 110.88, 140.5, 140.7, 152.78, 152.81, 166.6, 175.59, 175.64; $\delta_P$ (162 MHz, CDCl$_3$) 11.53, 11.56; m/z (ES+) 339.2 (M+H).

The following reactions where carried according to general scheme 2 described above:

1. O—H Insertion Reactions

The O—H insertion reactions were carried out with cis-diols and trimethylphosphonodiazoacetate in the presence of rhodium(II)acetate. The reaction was carried out under nitrogen in refluxing benzene. The following table shows the different compounds prepared by O—H insertion reactions.

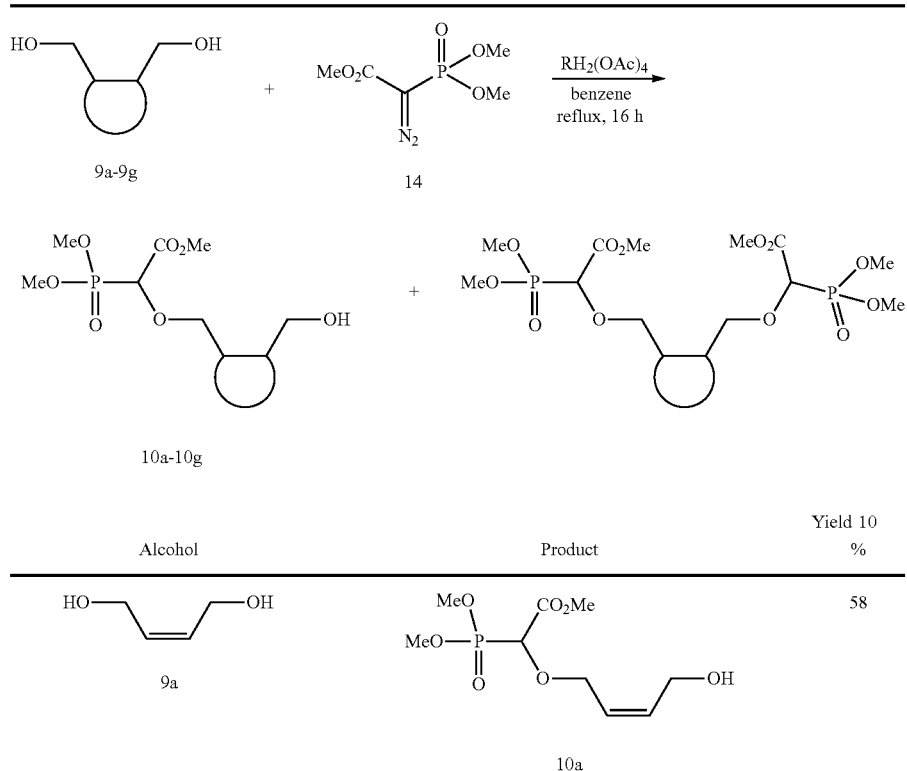

| Alcohol | Product | Yield 10 % |
|---|---|---|
| 9a | 10a | 58 |

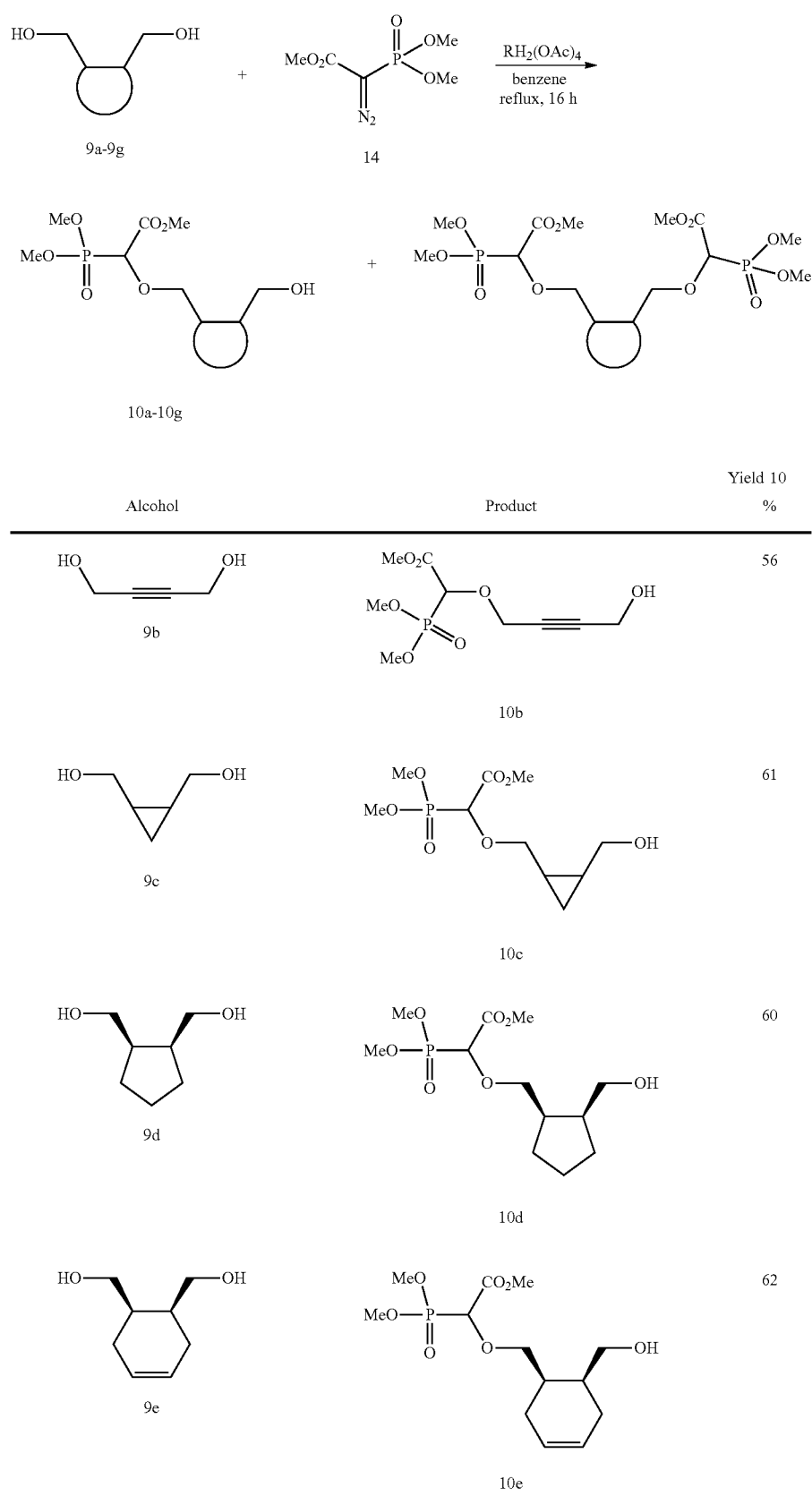

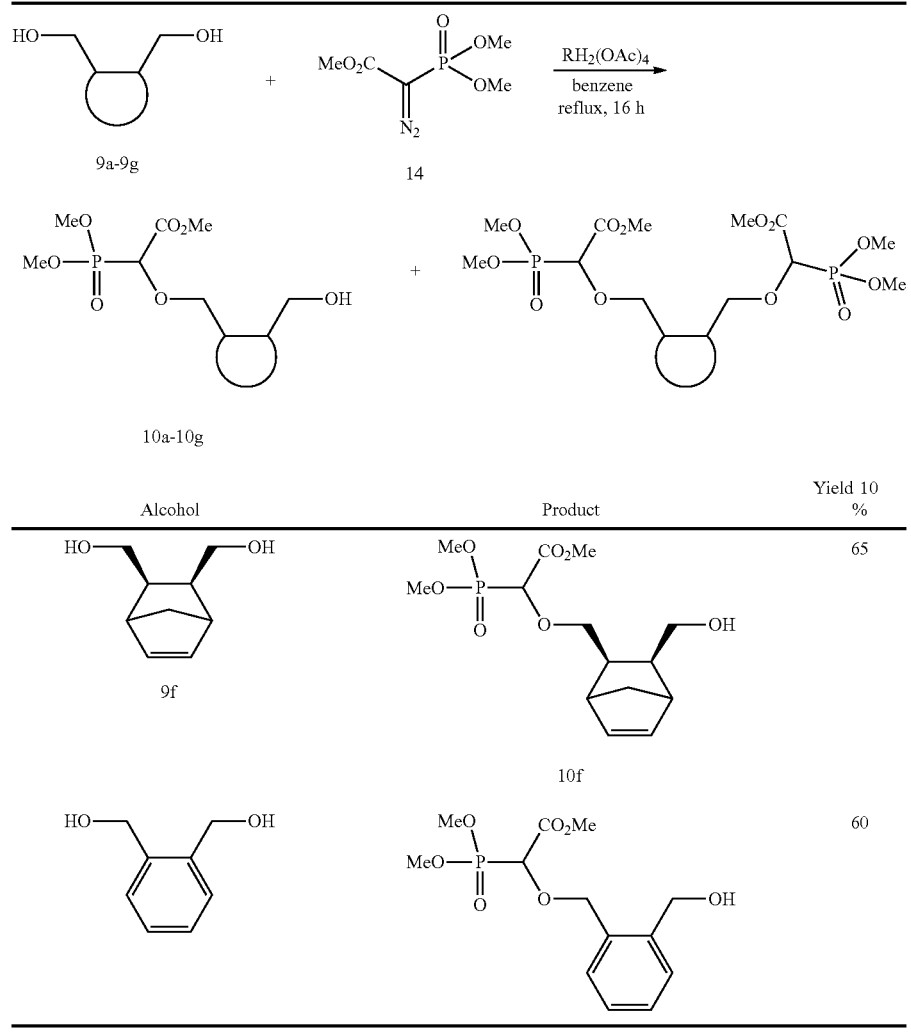

General Experimental Procedure for O—H Insertion Reactions

To a degassed solution of the diol (1 g) and trimethylphosphonodiazoacetate (1.2 equiv.) in benzene (100 mL) 1 mol % of rhodium(II)acetate was added and refluxed under nitrogen for 16 hours. The reaction was carried out at a concentration of 0.01 mM. After completion of the reaction as seen from thin layer chromatography, the solvent was evaporated off under reduced pressure. Purification was done by flash chromatography (Silica, 5% methanol in ethylacetate) yielding the O—H insertion product in 56-65% yield.

The following compounds where prepared following the protocol for O—H insertion reactions:

cis-Methyl 2-(dimethoxyphosphoryl)-2-(4-hydroxybut-2-enyloxy)acetate 10a

Light yellow oil (58%, 1.76 g); $\delta_H$ (300 MHz, CDCl$_3$): 3.83-3.89 (m, 9H), 4.10-4.28 (m, 3H), 4.35-4.39 (m, 1H), 4.42-4.48 (d, 1H, J$_{PH}$=18.9 Hz), 5.66-5.74 (m, 1H), 5.91-5.99 (m, 1H) ppm; $\delta_C$ (75 MHz, CDCl$_3$): 52.9, 54.1-54.4 (m), 58.4, 67.4, 67.6, 73.8, 75.9, 125.9, 135.1, 167.8 ppm. $\delta_P$ (160 MHz, CDCl$_3$): 16.9 ppm. HRMS (ESI) mass calculated for C$_9$H$_{17}$O$_7$P (M+1) 269.079; Found: 269.0788.

Methyl 2-(dimethoxyphosphoryl)-2-(4-hydroxybut-2-ynyloxy)acetate 10b

Light yellow oil (56%, 1.73 g); $\delta_H$ (300 MHz, CDCl$_3$): 3.29 (brs, 1H), 3.84-3.90 (m, 9H), 4.30-4.37 (m, 3H), 4.50-4.55 (m, 1H), 4.72-4.78 (d, 1H, J$_{PH}$=19.2 Hz) ppm; $\delta_C$ (75 MHz, CDCl$_3$): 50.6, 53.0, 53.5, 54.2-54.4 (m), 59.7, 67.5, 69.6, 72.3, 74.4, 78.8, 87.7, 167.3 ppm. $\delta_P$ (160 MHz, CDCl$_3$): 17.1 ppm. LRMS (EI) mass calculated for C$_9$H$_{15}$O$_7$P (M)$^+$ 266.1; Found: 266.1.

Methyl-2-(dimethoxyphosphoryl)-2-((2-(hydroxymethyl)cyclopropyl)methoxy)acetate 10c Light yellow oil (61%, 1.68 g, diastereomeric mixture); $\delta_H$ (400 MHz, CDCl$_3$): 0.18-0.20 (m, 1H), 0.81-0.85 (m, 1H), 1.36-1.38 (m, 2H), 3.26-3.37 (m, 2H), 3.84-3.90 (m, 9H), 3.94-4.01 (m, 1.5H), 4.07-4.11 (m, 0.5H), 4.34-4.39 (d, 0.5H, J$_{PH}$=18.8 Hz), 4.40-4.45 (d, 0.5H, J$_{PH}$=18.8 Hz) ppm; $\square_C$ (75 MHz, CDCl$_3$): 7.6, 7.7, 14.7, 14.9, 18.7, 18.8, 53.0, 53.1, 54.0-54.5 (m), 62.3, 73.2-73.6 (m), 74.5, 74.8, 167.6, 167.8 ppm. $\delta_P$ (160 MHz, CDCl$_3$): 15.9, 17.0 ppm. LRMS (EI) mass calculated for C$_{10}$H$_{19}$O$_7$P (M)$^+$ 282.1; Found: 282.0.

Methyl-2-(dimethoxyphosphoryl)-2-cis-2(hydroxymethyl)cyclopentyl)methoxy) acetate 10d Light yellow oil (60%, 1.42 g, diastereomeric mixture); $\delta_H$ (300 MHz, CDCl$_3$): 1.24-1.40 (m, 2H), 1.46-1.77 (m, 4H), 2.18-2.31 (m, 1H), 2.35-2.49 (m, 1H), 2.98-3.09 (m, 1H), 3.39-3.44 (m, 0.5H), 3.57-3.81 (m, 3.5H), 3.83-3.89 (m, 9H), 4.31-4.37 (m, 1H) ppm; $\delta_C$ (75 MHz, CDCl$_3$): 23.2, 23.3, 27.7, 27.8, 28.4, 28.8, 40.2, 40.7, 44.5, 44.9, 52.9, 53.9-54.4 (m), 63.1, 63.3, 74.3-74.6 (m), 75.4, 75.6, 167.7, 167.8 ppm. $\delta_P$ (160 MHz, CDCl$_3$): 17.0, 17.5 ppm; LRMS (EI) mass calculated for C$_{12}$H$_{23}$O$_7$P (M)$^+$ 310.1; Found: 310.5.

Methyl 2-(dimethoxyphosphoryl)-2-cis-6-(hydroxymethyl)cyclohex-3-enyl)methoxy)acetate 10e Light yellow oil (62%, 1.41 g, diastereomeric mixture); $\delta_H$ (400 MHz, CDCl$_3$): 1.90-2.22 (m, 5H), 2.34-2.40 (m, 1H), 3.39-3.43 (m, 0.5H), 3.56-3.62 (m, 1H), 3.64-3.79 (m, 3H), 3.85-3.90 (m, 9.5H), 4.32-4.40 (m, 1H), 5.59-5.66 (m, 2H) ppm; $\delta_C$ (75 MHz, CDCl$_3$): 25.8, 26.7, 26.9, 27.8, 33.7, 34.4, 36.8, 37.4, 52.9, 53.9-54.3 (m), 64.1, 64.2, 74.6, 74.7, 75.2, 75.4, 75.7, 125.1, 125.3, 125.6, 125.8, 167.7, 167.8 ppm; $\delta_P$ (160 MHz, CDCl$_3$): 16.5, 16.8 ppm. LRMS (EI) mass calculated for C$_{13}$H$_{23}$O$_7$P (M)$^+$ 322.1; Found: 322.5.

Methyl 2-(dimethoxyphosphoryl)-2-cis-3-(hydroxymethyl)bicyclo[2.2.1]hept-5-en-2-yl)methoxy)acetate 10f Light yellow oil (65%, 1.40 g, diastereomeric mixture); $\delta_H$ (400 MHz, CDCl$_3$): 1.27-1.30 (m, 1H), 1.40-1.46 (m, 1H), 1.77-1.81 (m, 1H), 1.90-1.92 (m, 1H), 2.17 (brs, 1H), 2.63-2.71 (m, 2H), 3.62-3.80 (m, 3H), 3.83-3.89 (m, 10H), 4.34-4.39 (d, 1H, J$_{PH}$=18.8 Hz), 6.17-6.22 (m, 2H) ppm; $\delta_C$ (75 MHz, CDCl$_3$): 40.6, 43.6, 43.7, 43.9, 45.4, 45.5, 45.7, 46.0, 52.9, 53.0, 54.1-54.4 (m), 64.1, 64.2, 75.2-75.7 (m), 136.9, 137.2, 137.9, 138.1, 167.6, 167.7 ppm; $\delta_P$ (160 MHz, CDCl$_3$): 16.7, 17.2 ppm; LRMS (EI) mass calculated for C$_{14}$H$_{23}$O$_7$P (M)$^+$ 334.1; Found: 334.6.

Methyl 2-(dimethoxyphosphoryl)-2-(2-(hydroxymethyl)benzyloxy)acetate 10g

Light yellow oil (60%, 1.38 g); $\delta_H$ (400 MHz, CDCl$_3$): 3.80-3.85 (m, 9H), 4.40-4.45 (d, 1H, J$_{PH}$=18.8 Hz), 4.67-4.72 (m, 2H), 4.80-4.83 (d, 1H, J=12.4 Hz), 4.95-4.98 (d, 1H, J=11.6 Hz), 7.28-7.32 (m, 2H), 7.37-7.41 (m, 1H), 7.47-7.49 (m, 1H) ppm; $\delta_C$ (75 MHz, CDCl$_3$): 53.0, 54.0-54.5 (m), 62.9, 73.0-73.3 (m), 75.4, 127.9, 129.6, 130.5, 130.6, 133.5, 141.1, 167.6 ppm; $\delta_P$ (160 MHz, CDCl$_3$): 17.3 ppm. LRMS (EI) mass calculated for C$_{13}$H$_{19}$O$_7$P (M)$^+$ 318.1; Found: 318.4.

2. Mitsunobu Reactions

The introduction of nucleobase, thymine was carried out by Mitsunobu reaction. The following table shows the different phosphonucleoside derivatives prepared.

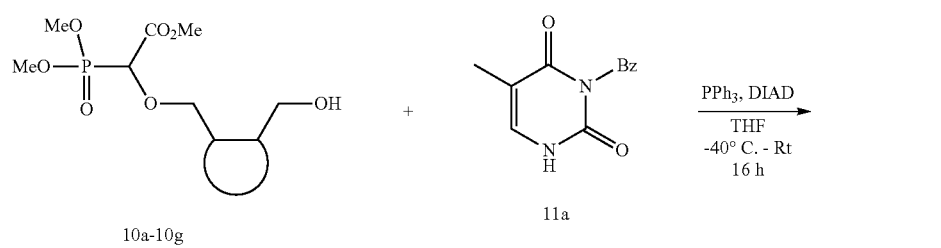

| Alcohol | Product | Yield 6 (%) |
|---|---|---|
| 10a | 12a | 51 |

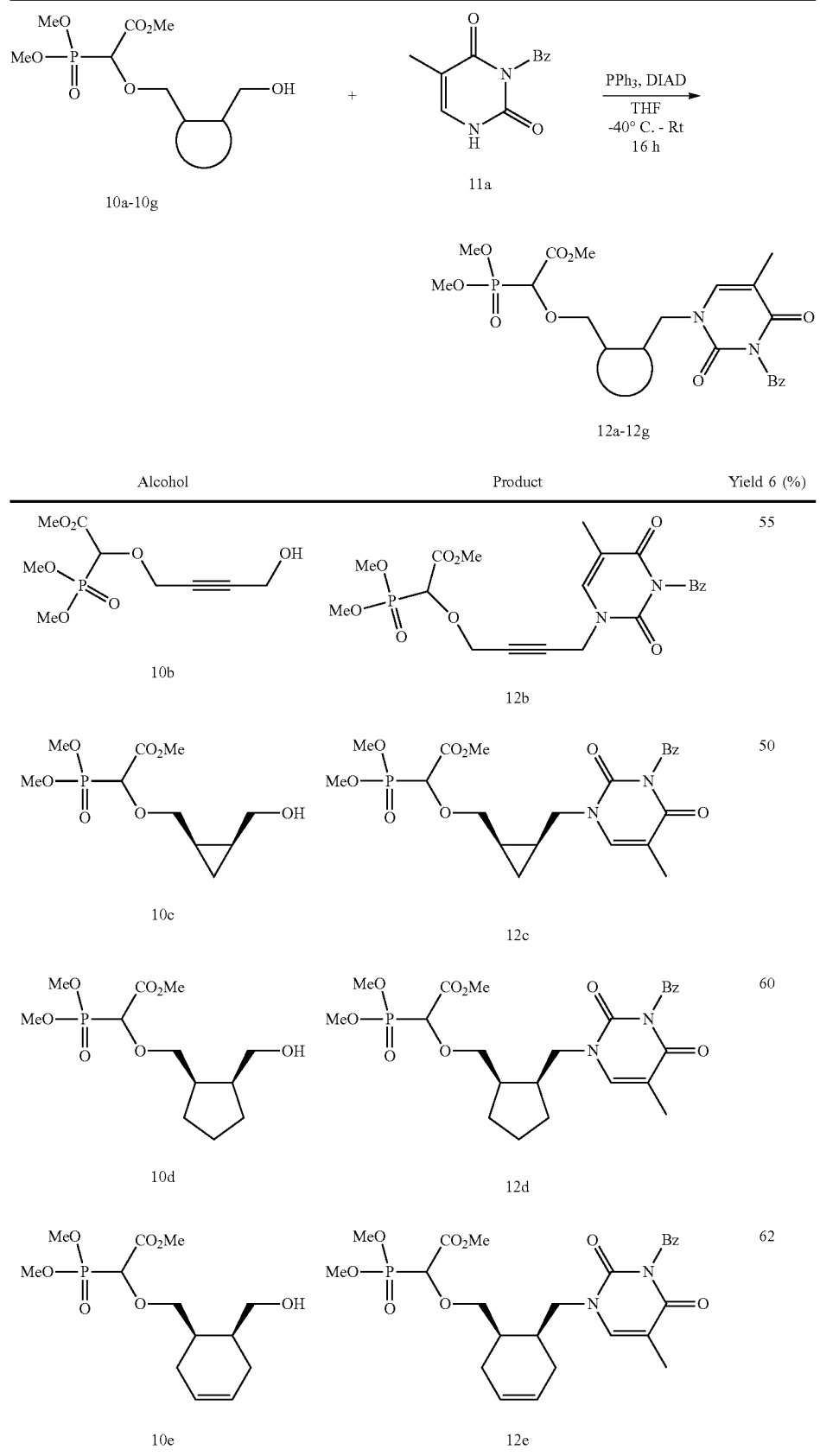

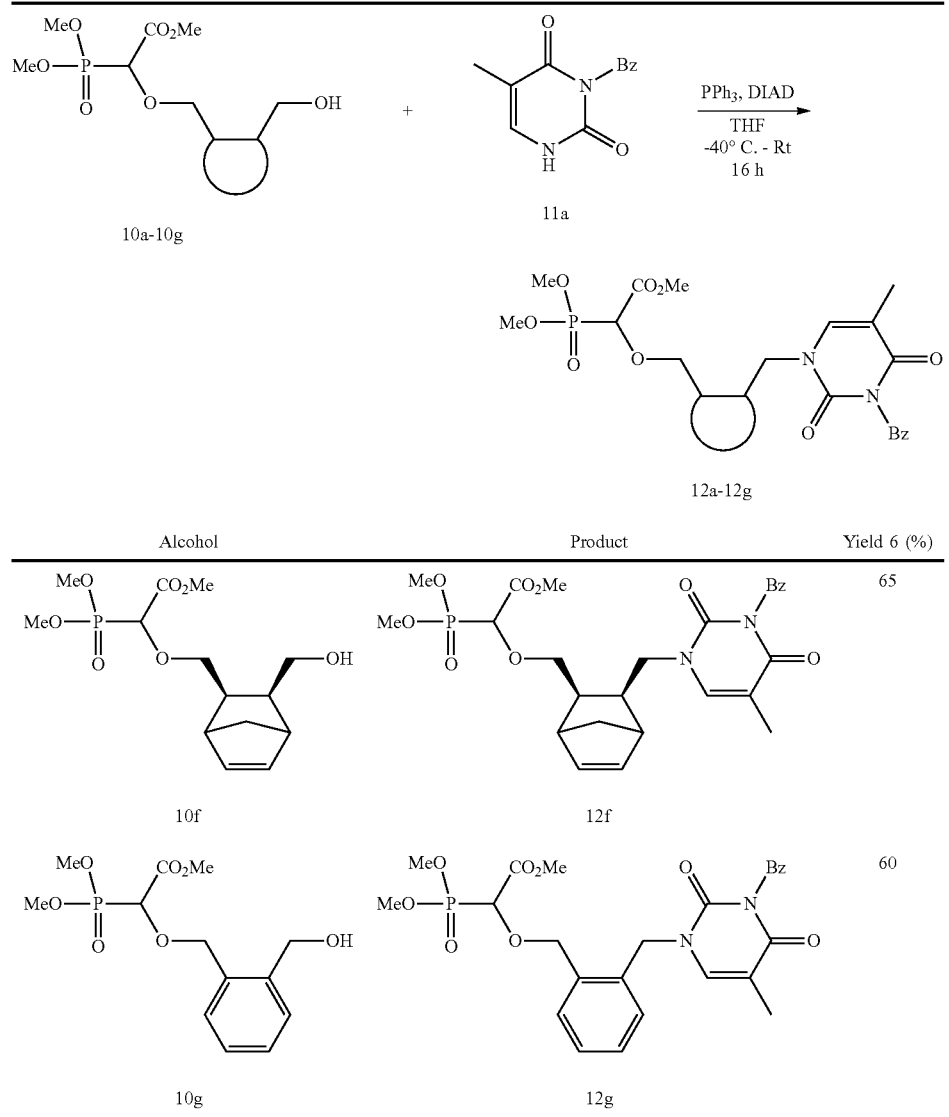

General Experimental Procedure for Mitsunobu Reactions

To a flame dried flask PPh$_3$ (2.1 equiv.) was added and degassed. After flushing nitrogen for 10 minutes, THF was added to it and cooled in an ice bath. Then diisopropylazodicarboxylate (DIAD) (2.0 equiv.) was added drop wise to the reaction mixture and a colour change was observed. This was allowed to stir for 30 minutes. In another flask the alcohol 10 (1.0 equiv.) and N-3-benzoyl thymine 11a (1.3 equiv.) were taken; degassed, flushed with nitrogen and then dissolved in THF and allowed to cool to −40° C. in an acetonitrile-dry ice bath. To this flask the PPh$_3$-DIAD solution was added and allowed to attain room temperature gradually and stirred for approximately 16 hours or until complete consumption of the alcohol 10. After completion of the reaction the solvent was evaporated off under reduced pressure and purification was done by flash chromatography (Silica, 3% methanol in ethylacetate) affording phosphonucleoside products in 50-66% yield.

The following compounds where prepared following the protocol for Mitsunobu reactions:

cis-Methyl 2-(dimethoxyphosphoryl)-2-(4-(3-benzoyl-2,4-dioxo-5-methyl-pyrimidin-1-yl)but-2-enyloxy)acetate 12a Light yellow oil (51%, 910 mg); $\delta_H$ (300 MHz, CDCl$_3$): 1.96 (s, 3H), 3.81-3.86 (m, 9H), 4.19-4.25 (m, 1H), 4.59-4.35 (m, 4H), 5.71-5.80 (m, 1H), 5.85-5.93 (m, 1H), 7.43-7.52 (m, 3H), 7.62-7.67 (m, 1H), 7.90-7.93 (d, 2H, J=7.5 Hz) ppm; $\delta_C$ (75 MHz, CDCl$_3$): 12.4, 42.9, 52.9, 54.1-54.4 (m), 58.4, 67.4, 67.6, 75.9, 110.9, 125.9, 129.1, 131.8, 141.0, 150.3, 163.3, 167.8, 169.6 ppm. $\delta_P$ (160 MHz, CDCl$_3$): 17.1 ppm. LRMS (EI) mass calculated for C$_{21}$H$_{25}$N$_2$O$_9$P (M)$^+$ 480.1; Found: 480.4.

Methyl 2-(dimethoxyphosphoryl)-2-(4-(3-benzoyl-2,4-dioxo-5-methyl-pyrimidin-1-yl) but-2-ynyloxy) acetate 12b Light yellow oil (55%, 980 mg); $\delta_H$ (300 MHz, CDCl$_3$): 1.97 (s, 3H), 3.84-3.90 (m, 9H), 4.73-4.91 (m, 5H), 7.42-7.51 (m, 3H), 7.61-7.65 (m, 1H), 7.90-7.93 (m, 2H) ppm; $\delta_C$ (150 MHz, CDCl$_3$): 12.4, 45.1, 53.4, 54.6-54.7 (d), 54.9-55.0 (d), 91.0, 92.1, 110.9, 129.2, 130.4, 130.5, 140.6, 149.8, 163.1, 168.0, 169.0 ppm. $\delta_P$ (160 MHz, CDCl$_3$): 16.6 ppm. LRMS (EI) mass calculated for C$_{21}$H$_{23}$N$_2$O$_3$P (M)$^+$ 478.1; Found: 478.2.

Methyl-2-(dimethoxyphosphoryl)-2-((2-(3-benzoyl-2,4-dioxo-5-methyl-pyrimidin-1-yl)cyclopropyl)methoxy)acetate 12c Light yellow oil (50%, 875 mg, diastereomeric mixture); $\delta_H$ (400 MHz, CDCl$_3$): 0.29-0.33 (m, 0.6H), 0.46-0.49 (m, 0.4H), 0.89-0.95 (m, 1H), 1.27-1.49 (m, 2H), 2.01 (s, 3H), 3.44-3.68 (m, 2H), 3.83-3.89 (m, 9.5H), 3.94-4.00 (m, 1H), 4.16-4.21 (m, 0.5H), 4.34-4.43 (m, 1H), 7.48-7.53 (m, 3H), 7.64-7.68 (m, 1H), 7.94-7.97 (m, 2H) ppm; $\delta_C$ (150 MHz, CDCl$_3$): 7.2, 7.7, 11.9, 12.0, 15.1, 15.4, 15.5, 15.6, 46.5, 47.1, 52.7, 53.6-53.9 (m), 72.2, 72.3, 72.5, 72.6, 75.5, 110.1, 110.3, 128.8, 130.2, 131.5, 134.6, 140.2, 140.7, 149.8, 149.8, 163.0, 163.2, 167.3, 167.4, 169.0, 169.1 ppm. $\delta_P$ (160 MHz, CDCl$_3$): 16.9, 17.6 ppm. LRMS (EI) mass calculated for C$_{22}$H$_{27}$N$_2$O$_9$P (M)$^+$ 494.1; Found: 494.3.

Methyl-2-(dimethoxyphosphoryl)-2-cis-2(3-benzoyl-2,4-dioxo-5-methyl-pyrimidin-1-yl)cyclopentyl)methoxy) acetate 12d Light yellow oil (60%, 1.01 g, diastereomeric mixture); $\delta_H$ (400 MHz, CDCl$_3$): 1.37-1.59 (m, 4H), 1.71-1.81 (m, 2H), 2.00 (s, 3H), 2.42-2.43 (m, 2H), 3.47-3.55 (m, 1H), 3.64-3.72 (m, 1H), 3.85-3.89 (m, 9H), 3.94-4.05 (m, 2H), 4.29-4.37 (m, 1H), 7.46-7.52 (m, 3H), 7.63-7.67 (m, 1H), 7.92-7.94 (m, 2H) ppm; $\delta_C$ (75 MHz, CDCl$_3$): 12.3, 22.3, 22.6, 27.7, 27.9, 28.4, 28.8, 40.9, 41.0, 41.8, 41.9, 48.5, 53.0, 53.9-54.3 (m), 73.9, 75.3, 110.4, 110.5, 129.1, 130.4, 131.8, 134.9, 141.0, 141.3, 150.3, 163.3, 163.4, 167.8, 169.4 ppm; $\delta_P$ (160 MHz, CDCl$_3$): 17.1, 17.5 ppm. LRMS (EI) mass calculated for C$_{24}$H$_{31}$N$_2$O$_9$P (M)$^+$ 522.1; Found: 522.1.

Methyl 2-(dimethoxyphosphoryl)-2-cis-6-(3-benzoyl-2,4-dioxo-5-methyl-pyrimidin-1-yl)cyclohex-3-enyl)methoxy)acetate 12e Light yellow oil (63%, 1.04 g, diastereomeric mixture); $\delta_H$ (300 MHz, CDCl$_3$): 1.79-1.92 (m, 2H), 1.98-1.99 (m, 3H), 2.08-2.42 (m, 4H), 3.46-3.51 (m, 0.5H), 3.60-3.65 (m, 0.5H), 3.71-3.79 (m, 1.5H), 3.82-3.87 (m, 9H), 3.90-4.13 (m, 1.5H), 4.30-4.36 (d, 1H, J$_{PH}$=18.9 Hz), 5.61-5.64 (m, 2H), 7.45-7.51 (m, 2H), 7.61-7.66 (m, 2H), 7.89-7.93 (m, 2H) ppm; $\delta_C$ (75 MHz, CDCl$_3$): 12.1, 12.2, 26.0, 26.2, 27.4, 27.8, 33.9, 34.4, 34.8, 49.9, 53.0, 53.8-54.4 (m), 74.0, 74.2, 75.2, 110.1, 125.1, 125.3, 129.1, 130.4, 131.8, 134.8, 141.9, 142.1, 150.2, 150.3, 163.4, 167.5, 167.8, 169.3 ppm; $\delta_P$ (160 MHz, CDCl$_3$): 17.1, 17.5 ppm; LRMS (EI) mass calculated for C$_{25}$H$_{31}$N$_2$O$_9$P (M)$^+$ 534.2; Found: 534.1.

Methyl 2-(dimethoxyphosphoryl)-2-cis-3-(3-benzoyl-2,4-dioxo-5-methyl-pyrimidin-1-yl)bicyclo[2.2.1]hept-5-en-2-yl)methoxy)acetate 12f Light yellow oil (65%, 1.06 g, diastereomeric mixture); $\delta_H$ (300 MHz, CDCl$_3$): 1.37-1.40 (m, 1H), 1.52-1.56 (m, 1H), 1.86-1.95 (m, 2H), 1.98 (s, 3H), 2.64-2.73 (m, 2H), 3.53-3.61 (m, 1H), 3.69-3.79 (m, 1H), 3.83-3.87 (m, 9H), 3.88-3.94 (m, 1H), 4.10-4.22 (m, 1H), 4.27-4.36 (m, 1H), 6.11-6.14 (m, 1H), 6.18-6.22 (m, 1H), 7.20-7.23 (m, 1H), 7.47-7.52 (m, 2H), 7.61-7.67 (m, 1H), 7.92-7.95 (d, 2H, J=7.5 Hz) ppm; $\delta_C$ (100 MHz, CDCl$_3$): 12.4, 40.8, 40.9, 41.1, 41.2, 43.2, 43.3, 44.5, 44.8, 45.1, 49.3, 49.5, 52.9, 53.9-54.2 (m), 74.4, 74.5, 77.5, 77.6, 110.8, 110.9, 129.1, 130.4, 131.8, 134.8, 136.8, 137.9, 138.0, 140.4, 140.6, 150.4, 163.1, 167.6, 169.1, 169.2 ppm; $\delta_P$ (160 MHz, CDCl$_3$): 17.1, 17.2 ppm; LRMS (EI) mass calculated for C$_{26}$H$_{31}$N$_2$O$_9$P (M)$^+$ 546.1; Found: 546.4.

Methyl 2-(dimethoxyphosphoryl)-2-(2-(3-benzoyl-2,4-dioxo-5-methyl-pyrimidin-1-yl)benzyloxy)acetate 12g Light yellow oil (60%, 1.00 g); $\delta_H$ (400 MHz, CDCl$_3$): 1.96 (s, 3H), 3.81-3.85 (m, 9H), 4.42-4.47 (d, 1H, J$_{PH}$=19.2 Hz), 4.63-4.66 (d, 1H, J=10.8 Hz), 4.88-4.91 (d, 1H, J=11.2 Hz), 5.17-5.27 (m, 2H), 7.32-7.34 (m, 3H), 7.40-7.43 (m, 2H), 7.50-7.54 (m, 2H), 7.64-7.68 (m, 1H), 7.96-7.98 (d, 2H, J=8.0 Hz) ppm; $\delta_C$ (75 MHz, CDCl$_3$): 12.3, 47.5, 53.0, 54.1-54.3 (m), 72.9, 73.1, 74.1, 111.1, 128.3, 128.6, 129.1, 130.0, 130.5, 131.2, 131.7, 133.6, 134.9, 135.8, 140.6, 150.5, 163.2, 167.4, 167.5, 169.1 ppm; $\delta_P$ (160 MHz, CDCl$_3$): 17.1 ppm; LRMS (EI) mass calculated for C$_{25}$H$_{27}$N$_2$O$_9$P (M)$^+$ 530.1; Found: 530.5.

Methyl-2-(4-(3-benzoyl-5-fluoro-2,4-dioxo-3,4-dihydropyrimidin-1(2H)-yl)but-2-enyloxy)-2-(dimethoxyphosphoryl)acetate 12h

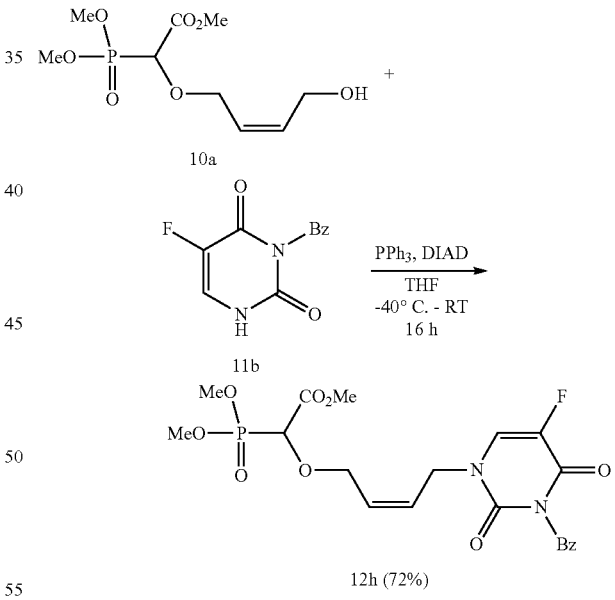

Colourless oil (72%, 1.4 g); $\delta_H$ (300 MHz, CDCl$_3$): 3.85-3.87 (m, 9H), 4.19-4.22 (m, 1H), 4.34-4.37 (m, 1H), 4.41-4.44 (d, 1H, J$_{PH}$=9.4 Hz) 4.65-4.56 (m, 2H), 5.81-5.83 (m, 1H), 5.95-5.96 (m, 1H), 7.51-7.54 (m, 2H), 7.67-7.69 (m, 1H), 7.90-7.95 (m, 3H); $\delta_C$ (75 MHz, CDCl$_3$): 45.3, 53.1, 53.0, 54.1-54.3 (m), 67.4, 67.6, 74.5, 128.4, 128.8, 129.2, 129.3, 129.6, 130.6, 131.1, 135.4, 138.5, 148.5, 167.4, 167.5 ppm; $\delta_P$ (240 MHz, CDCl$_3$): 16.2 ppm; HRMS (ESI) mass calculated for C$_{20}$H$_{22}$FN$_2$O$_9$P (M+1) 485.1125; Found: 485.1119.

Methyl-2-(4-(6-(bis(tert-butoxycarbonyl)amino)-9H-purin-9-yl)but-2-enyloxy)-2-(dimethoxyphosphoryl) acetate 12i

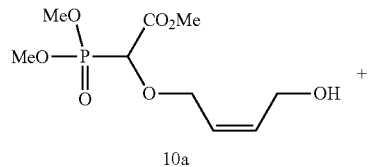

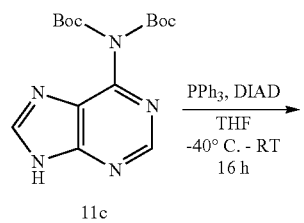

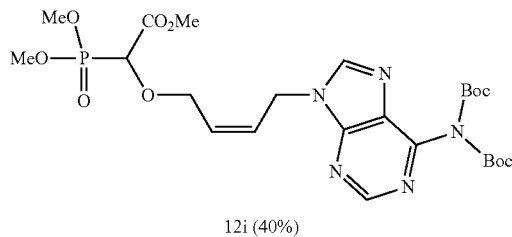

Light yellow oil (40%, 920 mg); δ$_H$ (300 MHz, CDCl$_3$): 1.46 (s, 18H), 3.84-3.89 (m, 9H), 4.34-4.40 (m, 1H), 4.50-4.56 (m, 1H), 4.54-4.60 (d, 1H, J$_{PH}$=18.9 Hz) 5.06-5.08 (d, 2H, J=6 Hz) 5.86-5.98 (m, 2H), 8.26 (s, 1H), 8.87 (s, 1H); δ$_C$ (75 MHz, CDCl$_3$): ppm; δ$_P$ (240 MHz, CDCl$_3$): 16.3 ppm; HRMS (ESI) mass calculated for C$_{24}$H$_{36}$N$_5$O$_{10}$P (M+1) 586.2277; Found: 586.2272.

Methyl-2-(4-(2-(tert-butoxycarbonylamino)-6-chloro-9H-purin-9-yl)but-2-enyloxy)-2-(dimethoxyphosphoryl)acetate 12j

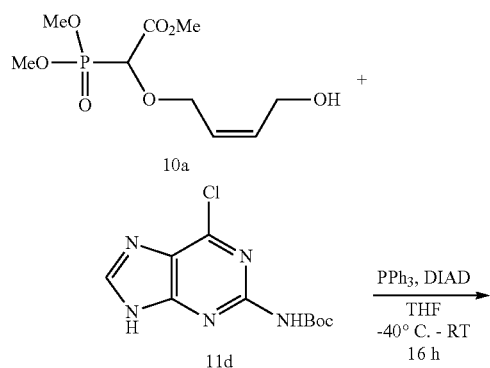

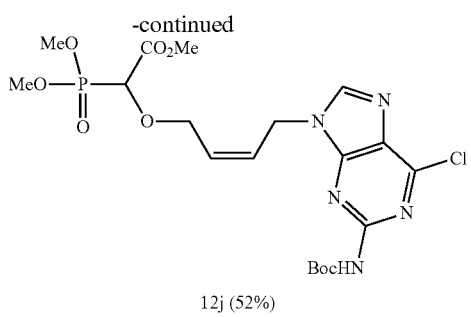

Colourless oil (52%, 804 mg); δ$_H$ (300 MHz, CDCl$_3$): 1.55 (s, 9H), 3.83-3.89 (m, 9H), 4.39-4.45 (m, 1H), 4.53-4.59 (m, 1H), 4.55-4.61 (d, 1H, J$_{PH}$=18.6 Hz) 4.96-4.98 (m, 2H) 5.83-5.96 (m, 2H), 7.79 (s, 1H), 8.09 (s, 1H) ppm; δ$_C$ (75 MHz, CDCl$_3$): 28.2, 40.9, 53.0, 54.1-54.4 (m), 67.7, 74.4, 81.6, 127.7, 130.0, 144.2, 150.3, 151.2, 152.5, 152.7, 167.5, 167.6 ppm; δ$_P$ (240 MHz, CDCl$_3$): 16.4 ppm; HRMS (ESI) mass calculated for C$_{19}$H$_{27}$ClN$_5$O$_8$P (M+1) 520.1364; Found: 520.1365.

Methyl 2-(4-(4-(bis(tert-butoxycarbonyl)amino)-2-oxopyrimidin-1(2H)-yl)but-2-enyloxy)-2-(dimethoxyphosphoryl)acetate 12k

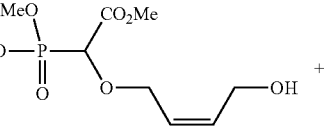

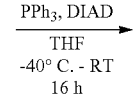

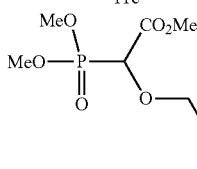

Colourless oil (43%, 805 mg); δ$_H$ (300 MHz, CDCl$_3$): 1.55 (s, 18H), 3.83-3.88 (m, 9H), 4.21-4.26 (m, 1H), 4.39-4.44 (m, 1H), 4.41-4.47 (d, 1H, J$_{PH}$=18.6 Hz) 4.54-4.70 (m, 2H) 5.77-5.92 (m, 2H), 7.00-7.03 (d, 1H, J=7.5 Hz), 7.79-7.81 (d, 1H, J=7.5 Hz) ppm; δ$_C$ (75 MHz, CDCl$_3$): 27.7, 47.0, 53.0, 54.2-54.3 (m), 67.5, 67.7, 74.5, 84.8, 96.5, 128.9, 129.0, 147.9, 149.6, 155.0, 162.4, 167.6 ppm; δ$_P$ (240 MHz, CDCl$_3$): 16.3 ppm; HRMS (ESI) mass calculated for C$_{23}$H$_{36}$N$_3$O$_{11}$P (M+1) 562.2165; Found: 562.2161.

3. Hydrogenation of Compounds 12a, 12e and 12h

The hydrogenation of phosphonucleosides 12a, 12e and 12h were done in the presence of palladium (5% on carbon) catalyst. The catalyst was added to a hydrogenation vessel followed by a solution of phosphonucleosides in methanol. The reaction mixture was shaken under hydrogen under 30 psi at room temperature for 12 hours. The completion of the reaction was monitored by checking $^1$H NMR of the crude reaction mixture. After completion the reaction mixture was filtered through a short column of celite and filtrate was concentrated in vacuo. Purification of the residue was done by flash chromatography (Silica, 3% methanol in ethylacetate) which yielded the reduced phosphonucleoside products 12l, 12m and 12n in excellent yields.

Methyl 2-(dimethoxyphosphoryl)-2-(4-(3-benzoyl-2,4-dioxo-5-methyl-pyrimidin-1-yl) butyloxy)acetate 12l

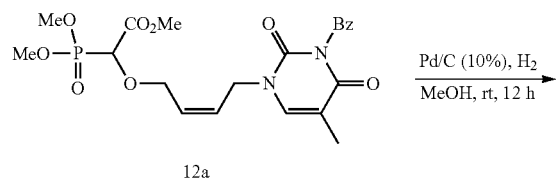

12a

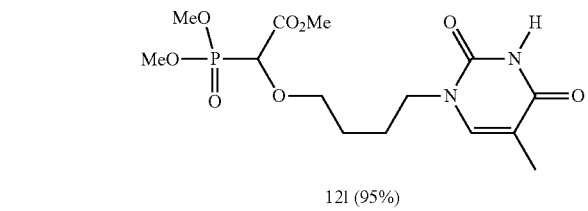

12l (95%)

It was observed that the N3-benzoyl group of the thymine part was also removed after hydrogenation.

Colourless oil (95%, 105 mg); $\delta_H$ (300 MHz, CDCl$_3$): 1.67-1.71 (m, 2H), 1.82-1.87 (m, 2H), 1.93 (s, 3H), 3.61-3.71 (m, 2H), 3.78-3.80 (m, 2H), 3.85-3.88 (m, 9H), 4.33-4.40 (d, 1H, J$_{PH}$=19.2 Hz), 7.18 (s, 1H), 9.67 (brs, 1H) ppm; $\delta_C$ (75 MHz, CDCl$_3$): 12.3, 25.9, 26.0, 48.0, 52.9, 54.0-54.2 (m), 72.6, 72.7, 110.5, 140.9, 150.7, 163.9, 167.7 ppm; $\delta_P$ (160 MHz, CDCl$_3$): 17.3 ppm; LRMS (EI) mass calculated for C$_{14}$H$_{23}$N$_2$O$_8$P (M)$^+$ 378.1; Found: 378.6.

Methyl 2-(dimethoxyphosphoryl)-2-cis-6-(3-benzoyl-2,4-dioxo-5-methyl-pyrimidin-1-yl)cyclohexyl)methoxy)acetate 12m

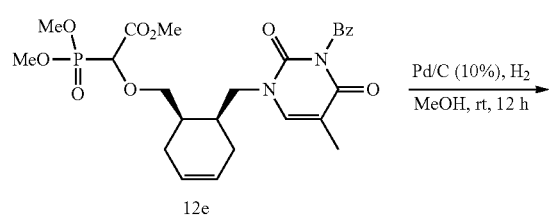

12e

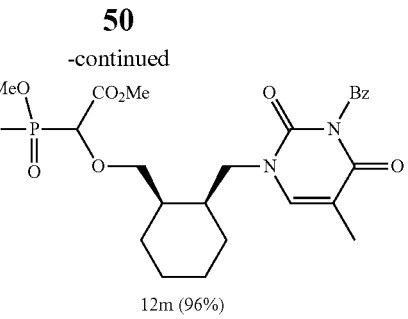

12m (96%)

Colourless oil (96%, 142 mg, diastereomeric mixture); $\delta_H$ (300 MHz, CDCl$_3$): 1.39-1.48 (m, 6H), 1.67-1.71 (m, 2H), 1.98 (s, 3H), 2.12-2.20 (m, 2H), 3.43-3.47 (m, 0.5H), 3.63-3.80 (m, 2.5H), 3.84-3.88 (m, 9H), 4.04-4.17 (m, 1H), 4.29-4.39 (m, 1H), 7.46-7.51 (m, 2H), 7.56-7.66 (m, 2H), 7.90-7.94 (m, 2H) ppm; $\delta_C$ (75 MHz, CDCl$_3$): 12.2, 22.9, 23.7, 25.9, 27.0, 36.8, 37.7, 53.0, 54.1-54.3 (m), 73.9, 74.1, 110.3, 110.5, 129.1, 130.4, 131.8, 134.8, 141.3, 141.6, 150.5, 163.4, 167.9, 169.4 ppm; $\delta_P$ (160 MHz, CDCl$_3$): 17.1, 17.6 ppm; LRMS (EI) mass calculated for C$_{25}$H$_{33}$N$_2$O$_9$P (M)$^+$ 536.2; Found: 536.5.

Methyl-2-(4-(3-benzoyl-5-fluoro-2,4-dioxo-3,4-dihydropyrimidin-1(2H)-yl)butoxy)-2-(dimethoxyphosphoryl)acetate 12n

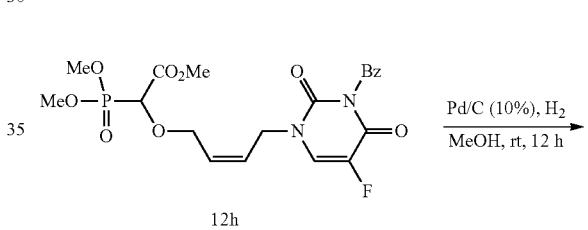

12h 12n (92%)

Colourless oil (92%, 170 mg); $\delta_H$ (300 MHz, CDCl$_3$): 1.69-1.73 (m, 2H), 1.87-1.94 (m, 2H), 3.65-3.70 (m, 2H), 3.76-3.93 (m, 11H), 4.32-4.38 (d, 1H, J$_{PH}$=19.2 Hz), 7.49-7.54 (m, 2H), 7.65-7.70 (m, 1H), 7.78-7.80 (d, 1H, J=6 Hz), 7.90-7.94 (m, 2H) ppm; $\delta_C$ (75 MHz, CDCl$_3$): 25.6, 26.0, 48.9, 53.0, 54.1-54.2 (m), 72.7, 72.9, 75.2, 129.3, 129.5, 129.9, 130.6, 131.1, 135.4, 138.2, 141.4, 148.5, 156.3, 156.7, 167.5, 167.7 ppm; $\delta_P$ (240 MHz, CDCl$_3$): 16.6 ppm.

4. Deprotection Reactions

The deprotection of the phosphonate part was done using TMSBr and the carboxylic ester hydrolysis was done with aqueous NaOH solution. The fully deprotected phosphonucleosides were purified on an activated charcoal column and eluted as ammonium salts. The following table shows the different phosphonucleoside derivatives prepared.

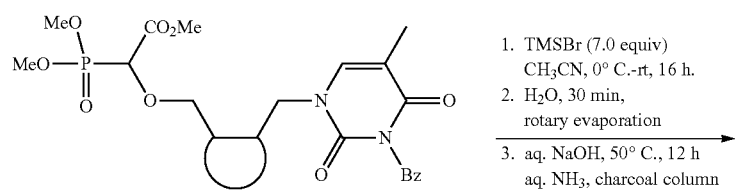
12a-12i
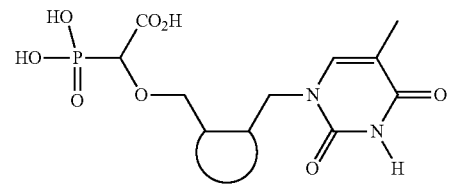
13a-13j (isolated as ammonium salts)
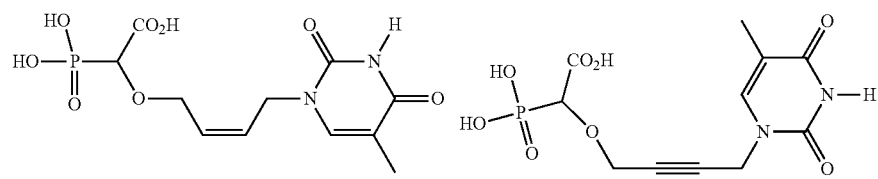
13a (61%)          13b (68%)
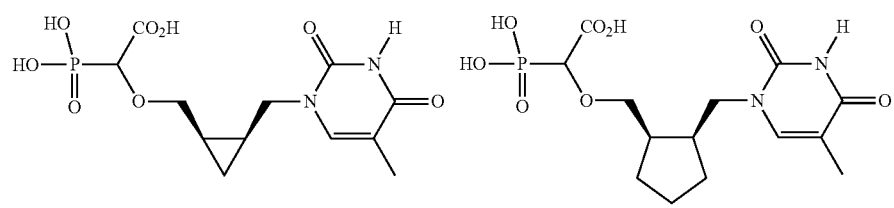
13c (49%)          13d (55%)
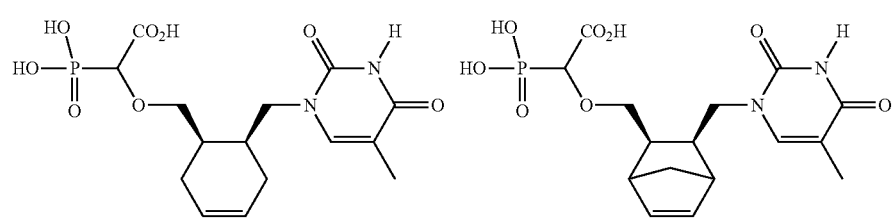
13e (60%)          13f (65%)
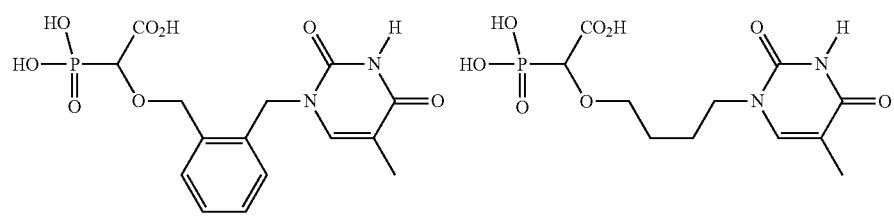
13g (52%)          13h (63%)

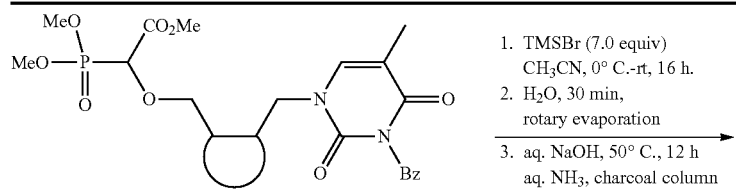

12a-12i

1. TMSBr (7.0 equiv) CH₃CN, 0° C.-rt, 16 h.
2. H₂O, 30 min, rotary evaporation
3. aq. NaOH, 50° C., 12 h aq. NH₃, charcoal column

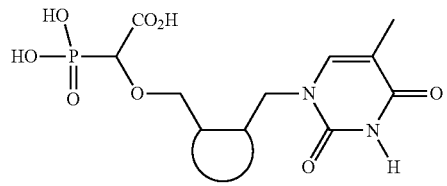

13a-13j (isolated as ammonium salts)

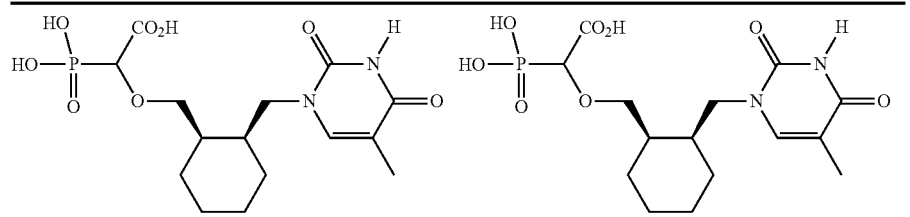

13i (59%)  13j (60%)

General Experimental Procedure for Deprotection Reactions

The deprotection of trimethyl thymine derivatives 13a-13i was done using TMSBr. The phosphonucleosides were treated with 7 equivalents of TMSBr at 0° C., slowly allowed to return to room temperature and stirred overnight. Water was added to hydrolyze the resulting silyl ethers and the reaction mixture was concentrated. The residue was then dissolved in 1M NaOH (10 equivalents) and stirred at 50° C. overnight. The reaction mixture was concentrated and acidified to pH 1-2.5 and washed 3 times with DCM to remove the benzoic acid. A small pad of activated charcoal (G-60) was made in a sintered funnel and then washed with 20% ammonia and water. Next the acidified aqueous layer was packed on the charcoal column. Then washed twice with water to remove the inorganic impurities and then the phosphonucleosides (13a-13c&13h) were eluted as ammonium salt by eluting with 20% ammonia solution. The fractions were spotted on a TLC plate and the UV active fractions were combined and concentrated by lyophilisation. Phosphonucleosides (13d-13g &13i-13j) were eluted by using a 1:1 mixture of ethanol and 20% ammonia solution.

The following compounds where prepared following the protocol for Deprotection reactions:

cis-2-(4-(2,4-Dioxo-5-methyl-pyrimidin-1-yl)but-2-enyloxy)-2-phosphonoacetic acid 13a (white solid, 61%, 84 mg); $\delta_H$ (300 MHz, D$_2$O): 1.78 (s, 3H), 3.84-3.90 (d, 1H, $J_{PH}$=18.6 Hz), 4.02-4.19 (m, 2H), 4.35-4.37 (m, 2H), 5.49-5.58 (m, 1H), 5.79-5.82 (m, 1H), 7.41 (s, 1H) ppm; $\delta_C$ (75 MHz, D$_2$O): 11.2, 45.4, 66.3, 66.5, 79.8, 81.6, 110.9, 126.5, 130.7, 142.8, 152.3, 167.1, 177.4 ppm; $\delta_P$ (160 MHz, CDCl$_3$): 12.3-12.4 (d, J=17 Hz) ppm; LRMS (ESI) mass calculated for C$_{11}$N$_{15}$N$_2$O$_8$P (M+H)$^+$ 335.1; Found: 335.4.

2-(4-(2,4-Dioxo-5-methyl-pyrimidin-1-yl)but-2-ynyloxy)-2-phosphonoacetic acid 13b (white solid, 68%, 95 mg); $\delta_H$ (600 MHz, D$_2$O): 2.09 (s, 3H), 4.85-4.95 (m, 5H), 7.7 (s, 1H) ppm; $\delta_C$ (75 MHz, D$_2$O): 11.3, 45.9, 75.2, 82.3, 92.6, 94.6, 111.1, 124.4, 134.9, 143.1, 152.2, 167.1, 175.4 ppm; $\delta_P$ (160 MHz, CDCl$_3$): 13.9 ppm; LRMS (ESI) mass calculated for C$_{11}$H$_{13}$N$_2$O$_8$P (M+H)$^+$ 333.0; Found: 333.6.

2-cis-2-((2,4-Dioxo-5-methyl-pyrimidin-1-yl)methyl)cyclopropyl)methoxy)-2-phosphonoacetic acid 13c (white solid, 49%, 69 mg, diastereomeric mixture); $\delta_H$ (400 MHz, D$_2$O): 0.35-0.37 (m, 1H), 0.79-0.83 (m, 1H), 1.26-1.29 (m, 2H), 1.83 (s, 3H), 3.46-3.60 (m, 3H), 3.89-4.04 (m, 2H), 7.56-7.59 (m, 1H) ppm; $\delta_C$ (75 MHz, D$_2$O): 8.4, 11.1, 13.8, 16.8, 17.6, 50.8, 73.8, 113.1, 145.8, 155.0, 169.7 ppm; $\delta_P$ (160 MHz, CDCl$_3$): 12.4, 12.5 ppm; LRMS (ESI) mass calculated for C$_{12}$H$_{17}$N$_2$O$_8$P (M+H)$^+$ 349.1; Found: 349.3.

2-cis-2-((2,4-Dioxo-5-methyl-pyrimidin-1-yl)methyl)cyclopentyl)methoxy)-2-phosphonoacetic acid 13d (white solid, 55%, 79 mg, diastereomeric mixture); $\delta_H$ (300 MHz, D$_2$O): 1.23-1.47 (m, 4H), 1.62-1.66 (m, 2H), 1.78 (s, 3H), 2.25-2.37 (m, 2H), 3.23-3.27 (m, 1H), 3.34-3.57 (m, 2.5H), 3.76-3.87 (m, 1.5H), 7.29-7.32 (m, 1H) ppm; $\delta_C$ (150 MHz, $D_2O$): 21.9, 27.3, 27.5, 27.6, 40.2, 40.4, 40.5, 40.8, 48.6, 48.8, 71.7-71.8 (m), 82.1-82.4 (d), 82.9-83.3 (d), 110.1, 142.4, 160.1, 168.1, 176.7, 179.0 ppm; $\delta_P$ (160 MHz, $CDCl_3$): 11.7, 11.8 ppm; LRMS (ESI) mass calculated for $C_{14}H_{21}N_2O_8P$ $(M+H)^+$ 377.1; Found: 377.7.

2-cis-6-((2,4-Dioxo-5-methyl-pyrimidin-1-yl)methyl)cyclohex-3-enyl)methoxy)-2-phosphonoacetic acid 13e (white solid, 60%, 86 mg, diastereomeric mixture); $\delta_H$ (400 MHz, $D_2O$): 1.88-2.11 (m, 4H), 2.14-2.16 (m, 1H), 2.18 (s, 3H), 2.25-2.28 (m, 1H), 3.33-3.37 (m, 1H), 3.50-3.68 (m, 2H), 3.64-3.95 (m, 2H), 5.60-5.70 (m, 2H), 7.57-7.59 (d, 1H) ppm; $\delta_C$ (75 MHz, $D_2O$): 11.2, 25.7, 26.3, 30.2, 33.6, 33.9, 34.2, 110.5, 125.1, 126.1, 143.9, 152.6, 167.1, 176.7 ppm; $\delta_P$ (160 MHz, $CDCl_3$): 12.9 ppm; LRMS (ESI) mass calculated for $C_{15}H_{21}N_2O_8P$ $(M+H)^+$ 389.1; Found: 389.5.

2-exo-3-((2,4-Dioxo-5-methyl-pyrimidin-1-yl)methyl)bicyclo[2.2.1]hept-5-en-2-yl)methoxy)-2-phosphonoacetic acid 13f (white solid, 65%, 95 mg, diastereomeric mixture); $\delta_H$ (300 MHz, $D_2O$): 1.14-1.17 (m, 1H), 1.42-1.47 (m, 1H), 1.73 (s, 3H), 1.76-1.77 (m, 1H), 1.86-1.94 (m, 1H), 2.40-2.41 (m, 1H), 2.60-2.69 (m, 1H), 3.22-3.57 (m, 3H), 3.90-4.06 (m, 2H), 5.89-5.91 (m, 1H), 6.08-6.12 (m, 1H), 7.38-7.39 (m, 1H) ppm; LRMS (ESI) mass calculated for $C_{16}H_{21}N_2O_8P$ $(M+H)^+$ 401.1; Found: 401.6.

2-(2-((2,4-Dioxo-5-methyl-pyrimidin-1-yl)methyl)benzyloxy)-2-phosphonoacetic acid 13g (white solid, 52%, 75 mg); $\delta_H$ (300 MHz, $D_2O$): 1.76 (s, 3H), 3.83-3.88 (d, 1H, $J_{PH}$=17.4 Hz), 4.34-4.47 (d, 1H, J=12 Hz), 4.65-4.66 (m, 1H), 5.05 (s, 3H), 6.97-7.00 (m, 1H), 7.24-7.27 (m, 2H), 7.35-7.38 (m, 1H), 7.45 (s, 1H) ppm; $\delta_C$ (75 MHz, $D_2O$): 11.2, 48.8, 70.7, 78.9, 80.8, 111.1, 126.3, 127.9, 128.9, 130.5, 134.9, 143.5, 152.5, 167.1, 176.5 ppm; $\delta_P$ (240 MHz, $CDCl_3$): 11.7 ppm; LRMS (ESI) mass calculated for $C_{15}H_{17}N_2O_8P$ $(M+H)^+$ 385.1; Found: 385.5.

2-(4-(2,4-Dioxo-5-methyl-pyrimidin-1-yl)butyloxy)-2-phosphonoacetic acid 13h (white solid, 63%, 112 mg); $\delta_H$ (400 MHz, $D_2O$): 1.59-1.73 (m, 4H), 1.84 (s, 3H), 3.43-4.47 (m, 1H), 3.58-3.60 (m, 1H), 3.73-3.83 (m, 2H), 3.87-3.93 (m, 1H), 7.49 (s, 1H) ppm; $\delta_C$ (100 MHz, $D_2O$): 11.3, 18.3, 24.9, 25.6, 30.3, 48.5, 71.4, 78.6, 80.9, 110.6, 143.5, 152.4, 167.1, 175.3 ppm; $\delta_P$ (160 MHz, $CDCl_3$): 13.3 ppm; LRMS (ESI) mass calculated for $C_{11}H_{17}N_2O_8P$ $(M+H)^+$ 337.1; Found: 337.7.

2-cis-6-((2,4-Dioxo-5-methyl-pyrimidin-1-yl)methyl)cyclohexyl)methoxy)-2-phosphonoacetic acid 13i (white solid, 59%, 86 mg); $\delta_H$ (300 MHz, $D_2O$): 1.17-1.20 (m, 4H), 1.35-1.38 (m, 4H), 1.73 (s, 3H), 1.90-1.97 (m, 2H), 3.24-3.37 (m, 1H), 3.41-3.59 (m, 2H), 3.73-3.82 (m, 2H), 7.45-7.47 (m, 1H) ppm; $\delta_C$ (150 MHz, $D_2O$): 10.9, 22.7, 24.9, 25.0, 25.8, 36.4, 37.1, 38.2, 72.1, 80.2, 80.5, 81.4, 110.2, 143.5, 143.6, 152.4, 166.8, 176.6 ppm; $\delta_P$ (160 MHz, $CDCl_3$): 12.9, 13.0 ppm; LRMS (ESI) mass calculated for $C_{15}H_{23}N_2O_8P$ $(M+H)^+$ 391.1; Found: 391.1.

2-methoxy-1-cis-2-((2,4-Dioxo-5-methyl-pyrimidin-1-yl)methyl)cyclohexyl)methoxy)-2-oxoethylphosphonic acid 13j This compound was obtained when the deprotection of compound 12i was done. This compound was also purified following the general experimental procedure for deprotection of phosphonucleosides. This compound contained 10% of compound 13i as seen in $^1H$ NMR. (white solid, 60%, 90 mg, diastereomeric mixture); $\delta_H$ (600 MHz, $D_2O$): 1.24-1.30 (m, 4H), 1.39-1.49 (m, 4H), 1.78-1.79 (m, 3H), 1.89-2.03 (m, 2H), 3.40-3.52 (m, 2H), 3.60-3.64 (m, 1H), 3.66-3.67 (m, 3H), 3.74-3.85 (m, 1H), 4.03-4.10 (m, 1H), 7.48-7.50 (m, 1H) ppm; $\delta_C$ (75 MHz, $D_2O$): 11.3, 22.9, 25.4, 26.1, 36.6, 48.4, 52.3, 73.0, 78.8, 80.6, 110.5, 143.6, 152.6, 167.0, 173.6 ppm; $\delta_P$ (240 MHz, $CDCl_3$): 8.5, 8.6 ppm;

2-Cis-(4-(5-fluoro-2,4-dioxo-3,4-dihydropyrimidin-1(2H)-yl)but-2-enyloxy)-2-phosphonoacetic acid 13k

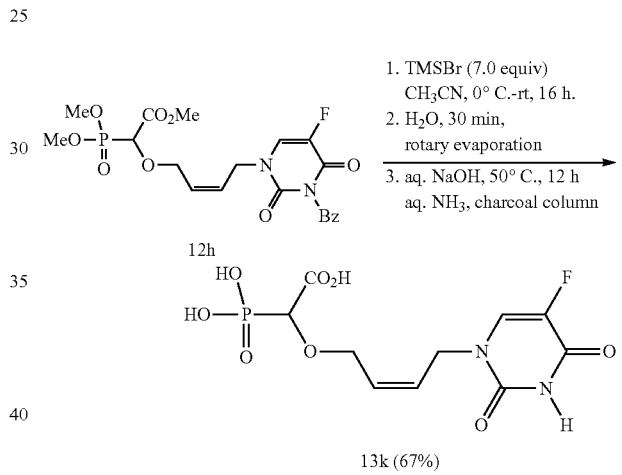

13k (67%)

White solid (67%, 70 mg); $\delta_H$ (300 MHz, $D_2O$): 3.83-3.89 (d, 1H, $J_{PH}$=17.7 Hz), 4.00-4.17 (m, 2H), 4.32-4.34 (d, 2H, J=6.9 Hz), 5.49-5.57 (m, 1H), 5.74-5.80 (m, 1H), 7.73-7.75 (m, 1H) ppm; $\delta_C$ (75 MHz, $D_2O$): 45.9, 66.3, 66.4, 79.6, 81.5, 126.3, 130.3, 130.7, 130.9, 139.2, 142.3, 152.3, 161.5, 177.2 ppm; $\delta_P$ (240 MHz, $CDCl_3$): 11.7 ppm; HRMS (ESI) mass calculated for $C_{10}H_{12}FN_2O_8P$ (M+H) 339.0393; Found: 339.0392.

2-(4-(5-fluoro-2,4-dioxo-3,4-dihydropyrimidin-1(2H)-yl)butoxy)-2-phosphonoacetic acid 13l

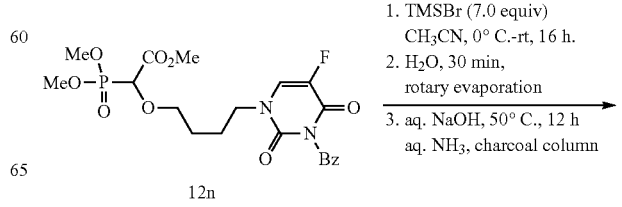

12n

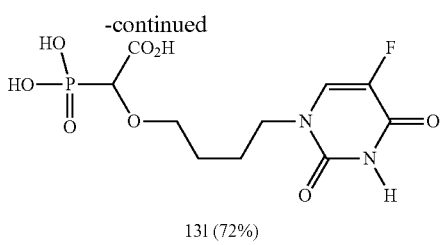

131 (72%)

White solid (72%, 80 mg); $\delta_H$ (300 MHz, D$_2$O): 1.48-1.53 (m, 2H), 1.60-1.67 (m, 2H), 3.28-3.36 (m, 1H), 3.46-3.53 (m, 1H), 3.67 (t, 2H, J=7.2 Hz), 3.78-3.84 (d, 1H, $J_{PH}$=18.0 Hz), 7.78-7.79 (d, 1H, J=6.0 Hz) ppm; $\delta_C$ (75 MHz, D$_2$O): 24.8, 25.5, 48.9, 71.3, 71.4, 79.5, 81.4, 131.2, 131.6, 151.1, 159.9, 164.0, 176.7 ppm; $\delta_P$ (240 MHz, CDCl$_3$): 12.3 ppm; LRMS (ESI) mass calculated for C$_{10}$H$_{12}$FN$_2$O$_8$P (M+H) 340.0; Found: 340.1.

2-Cis-(4-(6-amino-9H-purin-9-yl)but-2-enyloxy)-2-phosphonoacetic acid 13m

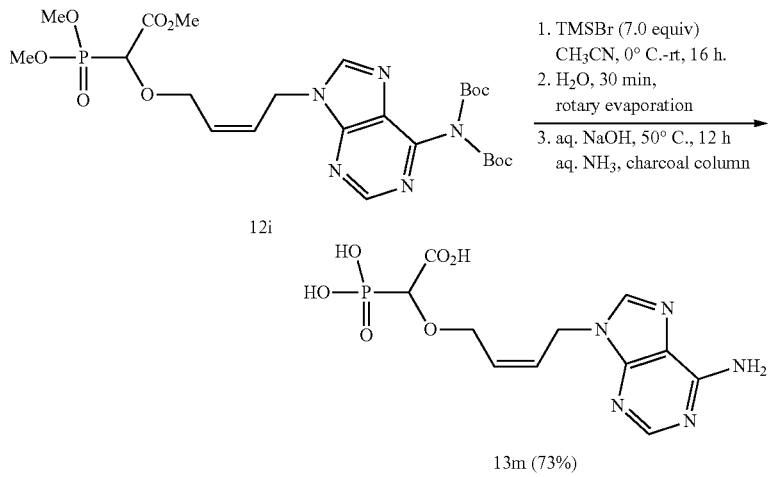

White solid (73%, 45 mg); $\delta_H$ (600 MHz, D$_2$O): 3.94-3.97 (d, 1H, $J_{PH}$=17.4 Hz), 4.14-4.26 (m, 2H), 4.83-4.84 (d, 2H, J=5.4 Hz), 5.74-5.85 (m, 2H), 8.07 (s, 1H), 8.11 (s, 1H) ppm; $\delta_C$ (150 MHz, D$_2$O): 40.9, 66.5, 66.6, 79.5, 80.4, 118.4, 126.6, 130.4, 130.7, 142.3, 148.7, 152.3, 155.4, 176.5 ppm; $\delta_P$ (240 MHz, CDCl$_3$): 11.9 ppm; LRMS (ESI) mass calculated for C$_{11}$H$_{14}$N$_5$O$_6$P (M+H) 344.1; Found: 344.0.

2-Cis-(4-(2-amino-6-chloro-9H-purin-9-yl)but-2-enyloxy)-2-phosphonoacetic acid 13n

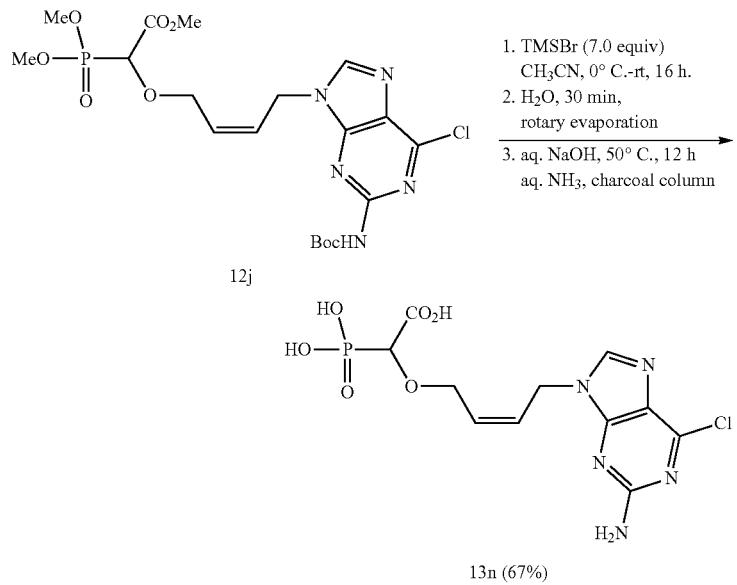

White solid (67%, 120 mg); $\delta_H$ (600 MHz, $D_2O$): 3.94-4.00 (d, 1H, $J_{PH}$=18.0 Hz), 4.10-4.26 (m, 2H), 4.62-4.69 (m, 2H), 5.60-5.82 (m, 2H), 7.7 (s, 1H) ppm; $\delta_C$ (75 MHz, $D_2O$): 40.7, 66.6, 78.7, 115.8, 127.0, 130.2, 139.8, 151.4, 158.9, 176.4 ppm; $\delta_P$ (240 MHz, $CDCl_3$): 12.2 ppm.

2-Cis-(4-(4-amino-2-oxopyrimidin-1(2H)-yl)but-2-enyloxy)-2-phosphonoacetic acid 13o

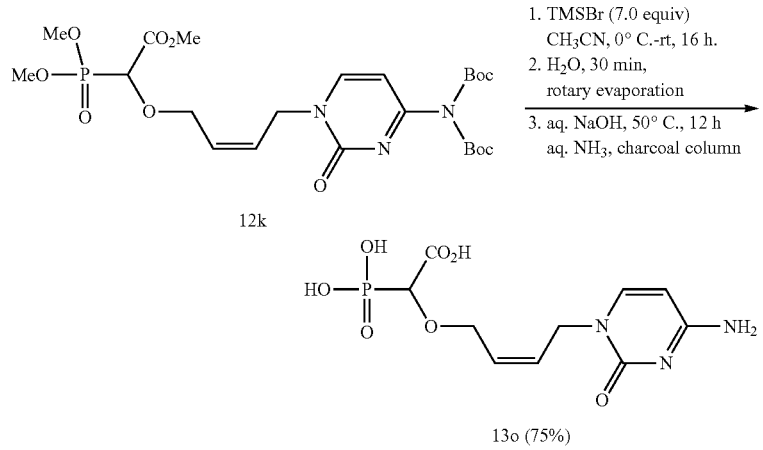

White solid (75%, 30 mg); $\delta_H$ (300 MHz, $D_2O$): 3.87-3.95 (d, 1H, $J_{PH}$=18.0 Hz), 4.02-4.19 (m, 2H), 4.35-4.37 (d, 2H, J=6.3 Hz), 5.53-5.61 (m, 1H), 5.70-5.79 (m, 1H), 5.87-5.89 (d, 1H, J=7.2 Hz), 7.52-7.55 (d, 1H, J=7.5 Hz) ppm; $\delta_C$ (75 MHz, $D_2O$): 46.8, 66.3, 66.5, 78.9, 80.3, 95.8, 127.5, 129.8, 146.7, 158.3, 166.4, 176.5 ppm; $\delta_P$ (240 MHz, $CDCl_3$): 12.1 ppm; HRMS (ESI) mass calculated for $C_{10}H_{14}N_3O_7P$ (M−H) 318.0491; Found: 318.0494.

Methyl 2-(2-azidoethoxy)-2-(dimethoxyphosphoryl)acetate 3g

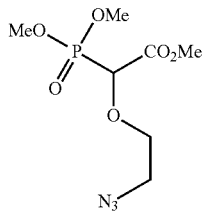

The O—H inserted product from the reaction of 2-bromoethanol and trimethylphosphonodiazoacetate was then treated with 3 equivalents of sodium azide in a 4:1 mixture of acetone/$H_2O$ and stirred at 60° C. for 6 h. After the completion of the reaction, acetone was evaporated and 25 mL of water were added. The aqueous layer was extracted with diethyl ether (3×20 mL). The organic layer was dried over anhydrous $MgSO_4$ and the solvent was evaporated to obtain the azido compound 3g as a light yellow oil (65% over two steps, 1.38 g); $\delta_H$ (400 MHz, $CDCl_3$): 3.47-3.49 (m, 2H), 3.70-3.75 (m, 1H), 3.85-3.89 (m, 10H), 4.41-4.46 (d, 1H, J=17.6 Hz) ppm; $\delta_C$ (100 MHz, $CDCl_3$): 50.7, 52.9, 54.1-54.3 (m), 71.3-71.4 (m), 75.9, 167.3 ppm; $\delta_P$ (160 MHz, $CDCl_3$): 16.6 ppm. HRMS (ESI) mass calculated for $C_7H_{14}O_6P$ (M+H) 268.0693; Found: 268.0689.

Synthesis of 1,2,3-Triazole Linked Phosphonucleoside 5g by Copper Catalyzed Click Reaction[3]

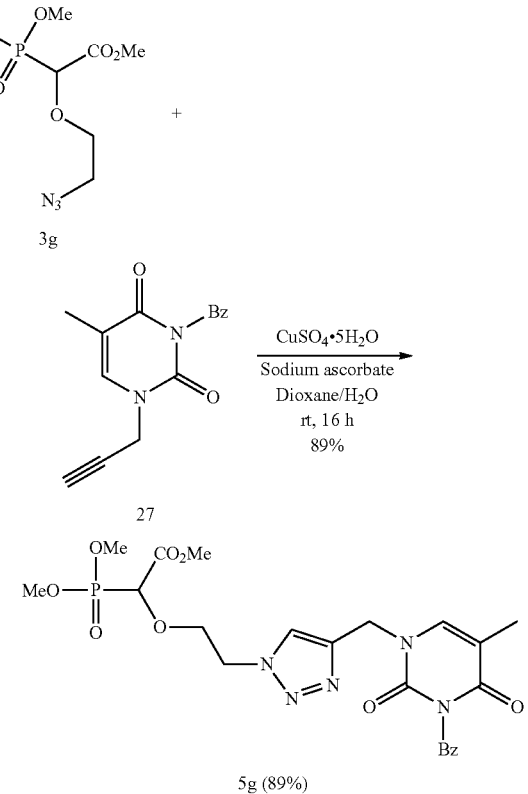

The dipolar cycloaddition of 3g (1.0 equiv.) and 27 (1.0 equiv.) was done in the presence of 5 mol % of CuSO$_4$.5H$_2$O and 10 mol % of sodium ascorbate in 2:1 mixture of dioxane and H$_2$O at room temperature for 16 h. After the completion of the reaction, the solvent was evaporated off under reduced pressure and purification was done by flash chromatography (Silica, 3% methanol in ethyl acetate) affording 1,2,3-triazole linked phosphonucleoside product 5g in 89% yield. Light yellow oil (89%, 420 mg); $\delta_H$ (600 MHz, CDCl$_3$): 1.95 (s, 3H), 3.76-3.80 (m, 9H), 3.98-4.08 (m, 2H), 4.32-4.35 (d, 1H, $J_{PH}$=18.0 Hz), 4.62-4.63 (m, 2H), 4.99-5.05 (m, 2H), 7.48-7.50 (m, 2H), 7.63-7.66 (m, 1H), 7.90-7.92 (d, 1H, J=6 Hz), 7.97 (s, 1H) ppm; $\delta_C$ (75 MHz, CDCl$_3$): 12.4, 42.9, 50.2, 53.1, 54.1-54.3 (m), 70.5, 70.6, 75.2, 111.2, 124.9, 129.2, 130.5, 131.6, 135.0, 140.0, 141.8, 149.8, 163.1, 166.9, 169.0 ppm; $\delta_P$ (240 MHz, CDCl$_3$): 15.6 ppm. HRMS (EI) mass calculated for C$_{22}$H$_{26}$N$_5$O$_9$P (M)$^+$ 535.1468; Found: 535.1475.

2-(2-(4-((5-methyl-2,4-dioxo-3,4-dihydropyrimidin-1(2H)-yl)methyl)-1H-1,2,3-triazol-1-yl)ethoxy)-2-phosphonoacetic acid JJ-210

JJ-210

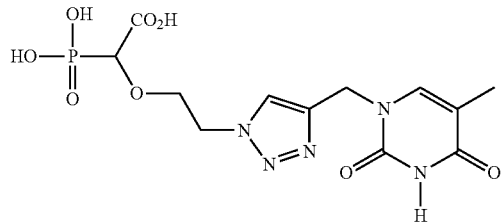

White solid (50%, 73 mg); mp 189-191° C.; $\delta_H$ (600 MHz, 323K, D$_2$O): 1.97 (s, 3H), 3.96-3.98 (m, 1H), 4.05-4.07 (d, 1H, $J_{PH}$=12.0 Hz), 4.11-4.12 (m, 1H), 4.74 (s, 2H), 5.15 (s, 2H), 7.64 (s, 1H), 8.33 (s, 1H) ppm; $\delta_C$ (75 MHz, D$_2$O): 11.1, 42.7, 50.5, 70.3, 76.7, 78.3, 110.9, 125.8, 142.6, 144.9, 152.0, 166.8, 172.2 ppm; $\delta_P$ (160 MHz, CDCl$_3$): 10.7 ppm; HRMS (ESI) mass calculated for C$_{12}$H$_{16}$N$_5$O$_5$P (M−H): 388.0663; Found: 388.0666.

Synthesis of Dihydroxy Phosphonucleoside 5k by OsO$_4$ Oxidation of 5h

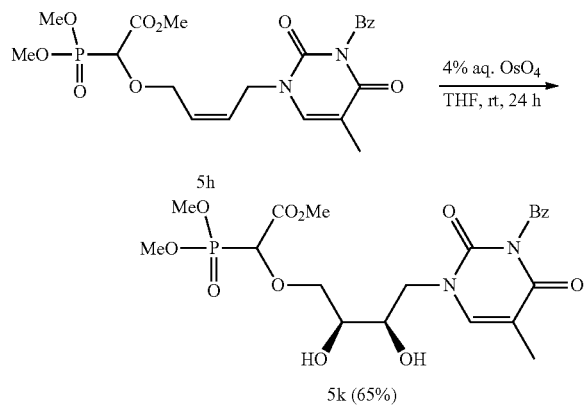

The oxidation of 5h (1.0 equiv.) was done by treating with 1.1 equivalents of 4% aq. OsO$_4$ solution in THF at room temperature for 24 h. After the completion, the reaction was quenched by the addition of aq. Na$_2$S$_2$O$_5$. The organic solvent was then evaporated under reduced pressure and the aqueous residue was extracted with ethyl acetate (4×20 mL). The organic layer was dried over anhydrous MgSO$_4$ and the solvent was evaporated off. The residue was then purified by flash chromatography (Silica, 5% methanol in ethylacetate) affording dihydroxy phosphonucleoside product 5k in 65% yield. Light yellow oil (65%, 140 mg); $\delta_H$ (300 MHz, CDCl$_3$): 1.97 (s, 3H), 3.53-3.56 (m, 1H), 3.83-3.86 (m, 10H), 3.91-3.95 (m, 1H), 4.05-4.09 (m, 3H), 4.35-4.46 (m, 1H), 7.33-7.34 (m, 1H), 7.47-7.53 (m, 2H), 7.63-7.68 (m, 1H), 7.91-7.94 (m, 2H) ppm; $\delta_C$ (75 MHz, CDCl$_3$): 12.4, 51.2, 53.2, 53.4, 54.1-54.5 (m), 70.2, 70.4, 70.8, 70.9, 75.2, 110.6, 129.2, 130.5, 131.5, 135.1, 142.2, 142.4, 151.6, 167.6, 168.8 ppm; $\delta_P$ (240 MHz, CDCl$_3$): 16.3, 17.4 ppm. HRMS (EI) mass calculated for O$_{21}$H$_{27}$N$_2$O$_{11}$P (M+H) 515.1425; Found: 515.1425.

2,3-Dihydroxy-4-(5-methyl-2,4-dioxo-3,4-dihydropyrimidin-1(2H)-yl)butoxy)-2-phosphonoacetic acid JJ-379

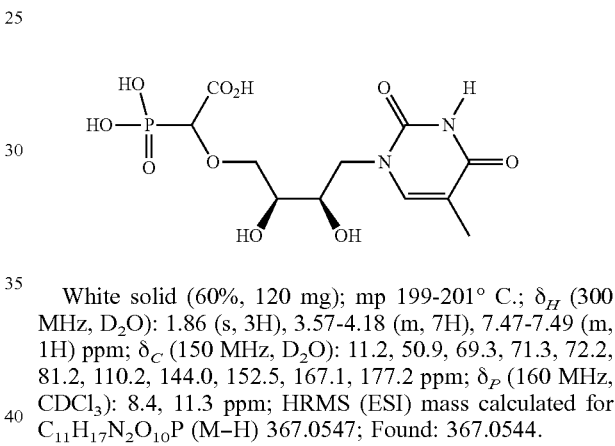

White solid (60%, 120 mg); mp 199-201° C.; $\delta_H$ (300 MHz, D$_2$O): 1.86 (s, 3H), 3.57-4.18 (m, 7H), 7.47-7.49 (m, 1H) ppm; $\delta_C$ (150 MHz, D$_2$O): 11.2, 50.9, 69.3, 71.3, 72.2, 81.2, 110.2, 144.0, 152.5, 167.1, 177.2 ppm; $\delta_P$ (160 MHz, CDCl$_3$): 8.4, 11.3 ppm; HRMS (ESI) mass calculated for C$_{11}$H$_{17}$N$_2$O$_{10}$P (M−H) 367.0547; Found: 367.0544.

Methyl-2-(dimethoxyphosphoryl)-2-trans-2(3-benzoyl-2,4-dioxo-5-methyl-pyrimidin-1-yl)cyclopentyl)methoxy) acetate 5q

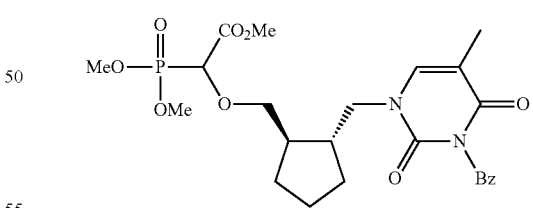

Light yellow oil (45%, 758 mg, diastereomeric mixture); $\delta_H$ (400 MHz, CDCl$_3$): 1.54-1.68 (m, 4H), 1.75-1.88 (m, 2H), 1.94-2.22 (s, 3H & m, 2H), 3.37-3.46 (m, 1H), 3.65-3.93 (m, 12H), 4.31-4.38 (m, 1H), 7.46-7.51 (m, 3H), 7.61-7.66 (m, 1H), 7.91-7.93 (m, 2H) ppm; $\delta_C$ (75 MHz, CDCl$_3$): 12.3, 24.3, 24.4, 28.7, 0.9, 31.0, 42.4, 44.1, 45.0, 51.9, 52.9, 54.0-54.1 (m), 75.2, 75.4, 110.5, 110.6, 129.1, 130.4, 131.8, 134.8, 141.0, 141.1, 150.4, 163.2, 167.7, 167.8, 169.3 ppm; $\delta_P$ (160 MHz, CDCl$_3$): 17.3, 17.4 ppm. HRMS (EI) mass calculated for C$_{24}$H$_{31}$N$_2$O$_9$P (M)$^+$ 522.1767; Found: 522.1755.

2-Trans-2-((5-methyl-2,4-dioxo-3,4-dihydropyrimidin-1(2H)-yl)methyl)cyclopentyl)methoxy)-2-phosphonoacetic acid JJ-609-F

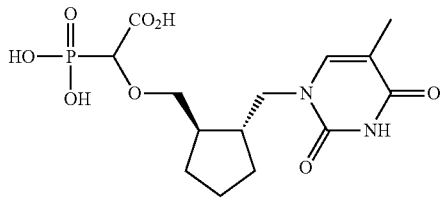

White solid (65%, 93 mg, diastereomeric mixture); mp above 300° C.; $\delta_H$ (300 MHz, D$_2$O): 1.21-1.80 (m, 6H), 1.85 (s, 3H), 1.92-2.07 (m, 2H), 3.28-3.48 (m, 2H), 3.68-3.90 (m, 3H), 7.56 (s, 1H) ppm; $\delta_C$ (150 MHz, D$_2$O): 11.2, 22.1, 23.3, 28.6, 34.4, 42.3, 42.6, 52.3, 75.6, 80.8, 81.1, 110.3, 143.7, 152.7, 166.9, 176.4 ppm; $\delta_P$ (160 MHz, CDCl$_3$): 12.9, 13.0 ppm; HRMS (ESI) mass calculated for C$_{14}$H$_{21}$N$_2$O$_8$F (M–H) 375.0962; Found: 375.0966.

2-Cis-((4-hydroxybut-2-en-1-yl)oxy)-2-phosphonoacetic acid JJ-621

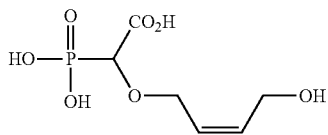

Isolated as a sodium salt. White solid (79%, 133 mg); mp above 300° C.; $\delta_H$ (300 MHz, D$_2$O): 3.80-3.85 (d, 1H, J$_{PH}$=18.0 Hz), 3.97-4.13 (m, 4H), 5.68-5.81 (m, 2H) ppm; $\delta_C$ (150 MHz, D$_2$O): δ7.1, 66.1, 66.2, 81.0, 81.9, 128.7, 131.6, 178.9 ppm; $\delta_P$ (160 MHz, CDCl$_3$): 11.7, 13.5 ppm; HRMS (ESI) mass calculated for C$_6$H$_{11}$O$_7$P (M–H) 225.0169; Found: 225.0168.

The following reactions were carried according to general scheme 3 described above:

N-(((2,2-Dimethyl-1,3-dioxolan-4-yl)methyl)carbamoyl)-3-methoxy-2-methylacrylamide 16

This was prepared according to the procedure described for 2a, starting from 3-methoxy-2-methylacrylic acid (1.0 g, 8.59 mmol), oxalyl chloride (0.8 mL, 1.12 g, 9.45 mmol), AgOCN (2.57 g, 17.2 mmol), and amine 15 (0.56 g 4.3 mmol). Yield 0.88 g (75%) colourless solid. $\delta_H$ (400 MHz, CDCl$_3$) 1.35 (3H, s), 1.46 (3H, s), 1.78 (3H, s), 3.41-3.56 (2H, m), 3.71 (1H, dd, J=8.3, 6.3), 3.86 (3H, s), 4.05 (1H, dd, J=8.3, 6.6), 4.24-4.31 (1H, m), 7.35 (1H, s), 7.96 (1H, s), 8.9 (1H, unresolved t, J~5.4); $\delta_C$ (100 MHz, CDCl$_3$) 8.7, 25.2, 26.6, 41.9, 61.3, 66.8, 74.3, 107.4, 109.4, 155.0, 158.4, 169.4; MS (ES+): m/z 273.3 (M+H); HRMS (ES+): calc. for C$_{12}$H$_{20}$N$_2$O$_5$ (M+H) 273.1450, found 273.1448.

1-((2,2-Dimethyl-1,3-dioxolan-4-yl)methyl)-5-methylpyrimidine-2,4(1H,3H)-dione 17

This was prepared according to the procedure described for 3b, starting from 16 (0.75 g, 2.75 mmol). Yield 0.66 g (~quantitative). $\delta_H$ (400 MHz, CDCl$_3$+CD$_3$OD) 1.35 (3H, s), 1.43 (3H, s), 1.91 (3H, s), 3.72 (1H, dd, J=8.8, 6.2), 3.78 (1H, dd, J=14.3, 6.6), 3.99 (1H, dd, J=14.3, 3.3), 4.11 (1H, dd, J=8.8, 6.6), 4.40 (qd, J=6.4, 3.3), 7.31 (1H, s); $\delta_C$ (100 MHz, CDCl$_3$+CD$_3$OD) 10.9, 24.0, 25.5, 49.2, 65.6, 73.4, 109.22, 109.23, 141.8, 151.2, 164.8; MS (ES+): m/z 241.3 (M+H); HRMS (ES+): calc. for C$_{11}$H$_{17}$N$_2$O$_4$ (M+H) 241.1188, found 241.1182.

3-Benzoyl-1-((2,2-dimethyl-1,3-dioxolan-4-yl)methyl)-5-methylpyrimidine-2,4(1H,3H)-dione 18

This was prepared according to the procedure described for 4a, starting from compound 17 (0.56 g, 2.33 mmol), DMAP (56 mg, 0.45 mmol), diisopropylethylamine (0.84 mL, 0.62 g, 4.8 mmol), and benzoyl chloride (0.42 mL, 0.51 g, 3.6 mmol). Yield 0.70 g (87%). $\delta_H$ (400 MHz, CDCl$_3$) 1.36 (3H, s), 1.46 (3H, s), 1.96 (3H, d, J=1.1), 3.68-3.76 (2H, m), 4.00 (1H, dd, J=14.3, 2.8), 4.08 (1H, dd, J=8.9, 6.7), 4.84 (1H, qd, J=6.6, 2.8), 7.24 (1H, unresolved q, J~1.1), 7.56-7.52 (2H, m), 7.61-7.67 (1H, m), 7.90-7.94 (2H, m); $\delta_C$ (100 MHz, CDCl$_3$) 12.3, 24.9, 26.6, 50.2, 66.2, 73.9, 109.9, 110.0, 129.1, 130.3, 131.5, 134.9, 141.4, 150.1, 163.0, 168.9; m/z (ES+) 367.2 (M+Na).

3-Benzoyl-1-(2,3-dihydroxypropyl)-5-methylpyrimidine-2,4(1H,3H)-dione 19

The acetonide 18 (0.695 g, 2.0 mmol) was treated with an ice-cold mixture of trifluoroacetic acid and water (1:1 v/v, 10 mL). After stirring for 1 h at 0° C., the mixture was concentrated under reduced pressure, then further concentrated from three portions of toluene, and finally re-concentrated from a mixture of CHCl$_3$ and methanol. The residue was triturated with a small amount of CHCl$_3$ to afford the desired product as a bone-white solid (0.447 g, 72%). $\delta_H$ (400 MHz, CD$_3$OD) 1.93 (3H, s), 3.53-3.58 (2H, m), 3.64 (1H, dd, J=13.9, 8.6), 3.87-3.93 (1H, m), 4.05 (1H, dd, J=13.9, 3.5), 7.53-7.61 (3H, m), 7.69-7.75 (1H, m), 7.93-7.99 (2H, m); $\delta_C$ (100 MHz, CD$_3$OD) 12.2, 52.8, 65.9, 70.9, 110.4, 130.4, 131.5, 133.1, 136.3, 144.9, 151.7, 165.4, 170.5; MS (ES+): m/z 305.2 (M+H); HRMS (ES+): calc. for C$_{15}$H$_{17}$N$_2$O$_5$ (M+H) 305.1137, found 305.1131.

3-Benzoyl-1-(3-((tert-butyldimethylsilyl)oxy)-2-hydroxypropyl)-5-methylpyrimidine-2,4(1H,3H)-dione 20

This was prepared according to the procedure described for 6, starting from 19 (0.531 g, 1.74 mmol), imidazole (0.285 g, 4.74 mmol), and tert-butyldimethylsilyl chloride (0.285 g, 1.89 mmol), in dimethylformamide (10 mL). Yield 0.60 g (82%). $\delta_H$ (400 MHz, CDCl$_3$) 0.09 (6H, s), 0.91 (9H, s), 1.96 (3H, s), 3.55 (1H, dd, J=10.3, 5.8), 3.62-3.70 (2H, m), 3.93-4.00 (1H, m), 4.02 (1H, dd, J=14.0, 3.0), 7.24 (1H, s), 7.46-7.52 (2H, m), 7.61-7.67 (1H, m), 7.90-7.94 (2H, m); $\delta_C$ (100 MHz, CDCl$_3$) –5.5, –5.45, 12.3, 18.2, 25.8, 51.1, 64.2, 70.4, 110.2, 129.1, 130.4, 131.7, 134.9, 141.5, 150.5, 163.1, 168.9; m/z (ES+) 419.2 (M+H).

1-(3-Benzoyl-5-methyl-2,4-dioxo-3,4-dihydropyrimidin-1(2H)-yl)-3-((tert-butyldimethylsilyl)oxy)propan-2-yl acetate 21

A solution of the alcohol 20 (0.49 g, 1.17 mmol) and 4-(dimethylamino)pyridine (28 mg, 0.24 mmol) in CH$_2$Cl$_2$ (5 mL) was treated with acetic anhydride (1.0 mL, 1.08 g, 10.57 mmol). The mixture was stirred for 1 h, diluted with saturated NaHCO$_3$ (10 mL) and stirred vigorously for a further 1 h. The organic phase was separated and the aqueous phase was extracted once with CH$_2$Cl$_2$. The combined organic phases were washed with NaHCO$_3$, 1M HCl, then brine, and dried over MgSO$_4$. The solvent was removed under reduced pressure and the residue was purified by flash chromatography (40% EtOAc/hexanes) to afford the desired product (0.32 g, 59%). $\delta_H$ (400 MHz, CDCl$_3$) 0.08 (3H, s), 0.09 (3H, s), 0.92 (9H, s), 1.95 (3H, br s), 2.02 (3H, s), 3.71-3.80 (3H, m), 4.21 (1H, dd, J=14.4, 3.7), 5.11-5.19 (1H, m), 7.12 (1H, s), 7.46-7.52 (2H, m), 7.61-7.66 (1H, m), 7.93-7.98 (2H, m); $\delta_C$ (100 MHz, CDCl$_3$) −5.5, 12.3, 18.2, 20.8, 25.7, 48.6, 61.8, 71.6, 110.4, 129.0, 130.5, 131.6, 134.9, 104.5, 149.9, 163.0, 168.8, 170.1; m/z (ES+) 461.3 (M+H).

1-(3-Benzoyl-5-methyl-2,4-dioxo-3,4-dihydropyrimidin-1(2H)-yl)-3-hydroxypropan-2-yl acetate 22

This was prepared following the procedure described for 5a, starting from 21 (0.32 g, 0.695 mmol) and TBAF (1 M, 0.76 mL, 0.76 mmol) in THF (20 mL). Flash chromatography (80% EtOAc/hexanes) afforded the desired product as a white amorphous solid (0.19 g, 80%). $\delta_H$ (400 MHz, CDCl$_3$) 1.96 (3H, s), 2.11 (3H, s), 2.75 (1H, d, J=3.8), 3.67 (1H, dd, J=14.2, 7.8), 4.04 (1H, dd, J=14.2, 2.5), 4.06-4.24 (3H, m) 7.22 (1H, s), 7.47-7.52 (2H, m), 7.62-7.67 (1H, m), 7.90-7.94 (2H, m); $\delta_C$ (100 MHz, CDCl$_3$) 12.2, 20.7, 51.3, 65.7, 68.2, 110.2, 129.2, 130.4, 131.4, 134.1, 141.7, 150.3, 163.2, 168.9, 171.1; m/z (ES+) 347.2 (M+H).

Methyl 2-((1-(3-benzoyl-5-methyl-2,4-dioxo-3,4-dihydropyrimidin-1(2H)-yl)-3-((tert-butyldimethylsilyl)oxy)propan-2-yl)oxy)-2-(dimethoxyphosphoryl)acetate 23

This was prepared according to the procedure described for 7a, starting from 20 (89 mg, 0.212 mmol), trimethyl phosphonodiazoacetate (47 mg, 0.225 mmol), and Rh$_2$(OAc)$_4$ (5.5 mg, 11 μmol). Yield 35 mg (28%). $\delta_H$ (400 MHz, CDCl$_3$) 0.04 (3H, s), 0.055 (3H, s), 0.063 (3H, s), 0.07 (3H, s), 0.88 (9H, s), 0.89 (9H, s), 1.96 (6H, br s), 3.50-4.00 (23H, m), 4.12-4.21 (2H, m), 4.67 (1H, d, J=17.1), 4.93 (1H, d, J=19.9), 7.34 (1H, s), 7.45-7.51 (3H, m), 7.60-7.66 (2H, m), 7.98-8.02 (2H, m), 8.07-8.12 (2H, m); $\delta_C$ (100 MHz, CDCl$_3$) −5.7, −5.6, 12.3, 18.1, 18.2, 25.6, 25.7, 25.8, 49.5, 49.7, 52.8, 52.9, 53.6, 53.7, 53.8, 53.9, 54.0, 54.1, 63.6, 64.1, 74.8 (d, J=158.5), 75.7 (d, J=158.1), 78.7, 78.8, 80.49, 80.54, 109.5, 109.8, 128.9, 129.0, 129.1, 130.44, 130.6, 130.7, 131.7, 131.9, 134.8, 134.9, 142.2, 142.3, 150.1, 150.2, 163.4, 163.56, 167.5, 167.6, 169.1, 169.3; $\delta_P$ (162 MHz, CDCl$_3$) 16.3, 17.3; m/z (ES+) 599.3 (M+H).

2-((1-Hydroxy-3-(5-methyl-2,4-dioxo-3,4-dihydropyrimidin-1(2H)-yl)propan-2-yl)oxy)-2-phosphonoacetic acid 24

This was prepared according to the procedure described for 8a, starting from 23 (26 mg, 0.052 mmol), and TMSBr (40 μL, 46 mg, 0.303 mmol). Yield 13 mg. $\delta_H$ (400 MHz, CDCl$_3$) 1.84 (3H, s), 3.50-4.25 (6H, m), 7.53 (1H, s); $\delta_C$ (100 MHz, CDCl$_3$) 11.2, 11.3, 48.0, 48.1, 49.2, 60.7, 60.8, 110.3, 144.0, 144.3, 152.5, 167.1, 175.4; $\delta_P$ (162 MHz, CDCl$_3$) 11.8, 12.6; m/z (ES+) 339.2 (M+H).

Methyl 2-(2-acetoxy-3-(3-benzoyl-5-methyl-2,4-dioxo-3,4-dihydropyrimidin-1(2H)-yl)propoxy)-2-(dimethoxyphosphoryl)acetate 25

This was prepared according to the procedure described for 7a, starting from 22 (85 mg, 0.245 mmol), trimethyl phosphonodiazoacetate (61 mg, 0.29 mmol), and Rh$_2$(OAc)$_4$ (4 mg, 8.3 μmol), and using 1,2-dichloroethane as solvent. Yield 60 mg (46%). $\delta_H$ (400 MHz, CDCl$_3$) 1.96 (3H, s), 1.97 (3H, s), 2.05 (3H, s), 2.09 (3H, s), 3.55-3.70 (2H, m) 3.78-3.94 (18H, m) 3.96-4.30 (8H, m) 4.47 (1H, d, J=17.5), 4.68 (1H, d, J=20.3), 7.36 (1H, s), 7.44-7.54 (5H, m), 7.60-7.67 (2H, m) 7.98-8.04 (2H, m), 8.06-8.11 (2H, m); $\delta_C$ (100 MHz, CDCl$_3$) 12.21, 12.24, 20.56, 20.63, 47.6, 47.7, 49.9, 50.3, 52.8, 53.0, 53.1, 53.6, 53.7, 54.06, 54.16, 60.5, 60.6, 75.45 (d, J=161.7), 75.50 (d, J=159.6), 109.7, 110.0, 129.0, 129.1, 130.6, 130.7, 131.7, 131.8 134.5, 134.9, 142.1, 142.2, 150.2, 163.3, 163.5, 167.2, 169.0, 169.2, 170.2, 170.3; $\delta_P$ (162 MHz, CDCl$_3$) 15.8, 16.7; m/z (ES+) 527.2 (M+H).

2-(2-Hydroxy-3-(5-methyl-2,4-dioxo-3,4-dihydropyrimidin-1(2H)-yl)propoxy)-2-phosphonoacetic acid 26

This was prepared according to the procedure described for 8a, starting from 25 (70 mg, 0.117 mmol), and TMSBr (95 μL, 109 mg, 0.71 mmol). Yield 29 mg. $\delta_H$ (400 MHz, CDCl$_3$) 1.83 (3H, s), 1.85 (3H, s), 3.3-4.5 (12H, m), 7.52 (1H, s), 7.59 (1H, s) $\delta_C$ (100 MHz, CDCl$_3$) 11.28, 11.31, 52.4, 52.5, 60.8, 60.9, 79.2 (d, J=8.2), 79.6 (d, J=11.3), 80.1 (d, J=140), 80.8 (d, J=141), 110.3, 110.6, 144.1, 144.2, 152.5, 167.1, 173.3; $\delta_P$ (162 MHz, CDCl$_3$) 11.5, 12.6; m/z (ES+) 339.2 (M+H).

Antiviral Activity Assays

The compounds were evaluated against the following viruses: herpes simplex virus type 1 (HSV-1) strain KOS, thymidine kinase-deficient (TK$^-$) HSV-1 KOS strain resistant to ACV (ACV$^r$), herpes simplex virus type 2 (HSV-2) strains Lyons and G, vaccinia virus Lederle strain, respiratory syncytial virus (RSV) strain Long, vesicular stomatitis virus (VSV), Coxsackie B4, Parainfluenza 3, Influenza virus A (subtypes H1N1, H3N2), influenza virus B, Reovirus-1, Sindbis, Reovirus-1, Punta Toro, human immunodeficiency virus type 1 strain III$_B$ and human immunodeficiency virus type 2 strain ROD. The antiviral, other than anti-HIV, assays were based on inhibition of virus-induced cytopathicity or plaque formation in human embryonic lung (HEL) fibroblasts, African green monkey cells (Vero), human epithelial cells (HeLa) or Madin-Darby canine kidney cells (MDCK). Confluent cell cultures in microtiter 96-well plates were inoculated with 100 CCID$_{50}$ of virus (1 CCID$_{50}$ being the virus dose to infect 50% of the cell cultures) in the presence of varying concentrations of the test compounds. Viral cytopathicity was recorded as soon as it reached completion in the control virus-infected cell cultures that were not treated with the test compounds. Antiviral activity was expressed as the EC$_{50}$ or compound concentration required to reduce virus-induced cytopathogenicity or viral plaque formation by 50%.

Anti-HIV Activity Assays

Inhibition of HIV-1(III$_B$)- and HIV-2(ROD)-induced cytopathicity in CEM cell cultures was measured in microtiter 96-well plates containing ~3×10$^5$ CEM cells/mL infected with 100 CCID50 of HIV per milliliter and containing appropriate dilutions of the test compounds. After 4-5 days of incubation at 37° C. in a $CO_2$-controlled humidified atmosphere, CEM giant (syncytium) cell formation was examined microscopically. The $EC_{50}$ (50% effective concentration) was defined as the compound concentration required to inhibit HIV-induced giant cell formation by 50%.

HIV-1 RT Assays in the Presence of Artificial Template/Primer

To prepare the template/primers for the RT experiments, 0.15 mM poly(U), poly(A), and poly(I) were mixed with an equal volume of 0.0375 mM oligo(dA), oligo(dT), and oligo(dC), respectively. The final concentrations of the templates in the RT reaction mixture were 0.015 mM. The reaction mixture (50 µl) contained 50 mM Tris.HCl (pH 7.8), 5 mM dithiothreitol, 300 mM glutathione, 500 µM EDTA, 150 mM KCl, 5 mM $MgCl_2$, 1.25 µg of bovine serum albumin, an appropriate concentration of labeled (tritiated) substrate dTTP, dCTP, or dATP (2 µCi/assay), a fixed concentration of the template/primer poly(A).oligo(dT) (0.015 mM), poly(I).oligo(dC) (0.015 mM), and poly(U).oligo(dA) (0.015 mM), 0.06% Triton X-100, 10 µl of inhibitor solution (containing various concentrations of the compounds), and 1 µl of the RT preparation. The reaction mixtures were incubated at 37° C. for 30 min, at which time 100 µl of yeast RNA (1 mg/ml) and 1 ml of $Na_4P_2O_7$ (0.02 M) in trichloroacetic acid (5% v/v) were added. The solutions were kept on ice for 30 min, after which the acid-insoluble material was washed and analyzed for radioactivity.

For the experiments in which the 50% inhibitory concentration ($IC_{50}$) of the test compounds was determined, fixed concentrations of 1.25 µM [$^3$H]dTTP, 1.75 µM [$^3$H]dATP, or 2.5 µM [$^3$H]dCTP were used.

The HCMV and HSV-1 DNA polymerase activity was measured in the presence of calf thymus DNA as template primer, and all four dNTPs as the nucleotide substrates of which dTTP was tritiated.

Biological Data

| | $IC_{50}{}^a$ (µM) | | |
|---|---|---|---|
| Compound | HIV-1 RT | HSV-1 DNA pol | HCMV DNA pol |
| 8a | 17 ± 0 | 19 | 161 ± 8 |
| 8b | 18 ± 0 | 12 | 111 ± 24 |
| 8c | 133 ± 16 | 16 | >200 |
| 13a | 235 ± 16 | 20 | 2.1 ± 0.6 |
| 13h | 145 ± 106 | 56 | 29 ± 3 |
| 13b | >500 | — | >500 |
| 13c | 440 ± 85 | 35 | 4.6 ± 0.2 |
| 13d | ≥500 | 34 | 40 ± 25 |
| 13e | 425 ± 106 | 16 | 3.0 ± 0.5 |
| 13j | ≥500 | 43 | 16 ± 3 |
| 13i | ≥500 | 13 | 4.0 ± 0.0 |
| 13g | 131 ± 86 | 11 | 13 ± 4 |
| 13f | 340 ± 139 | 32 | 14 ± 2 |
| 13k | >500* | | |
| 13l | 214* | | |
| 13m | 426* | | |
| 13o | 246* | | |
| 13n | ≥500* | | |

$^a$50% Inhibitory concentration, or compound concentration required to inhibit [$^3$H]dTTP incorporation into the template.
*In poly rA.dT/dTTP RT assay.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCES

[1] Gallo, R. C.; Montagnier, L. *New England Journal of Medicine* 2003, 349, 2283.
[2] WHO UNAIDS Global Facts & Figures; CDC Worldwide Hepatitis Statistics
[3] Broder, S. *Antiviral Research* 2010, 85, 1.
[4] Vandamme, A.-M.; Van, L. K.; De Clercq, E. *Drugs* 1999, 57, 337.
[5] De Clercq, E. *Nat. Rev. Drug Discovery* 2007, 6, 1001
[6] De Clercq, E. *Current Opinion in Pharmacology* 2010, 10, 507.
[7] Combination Therapy of AIDS; Birkhauser Basel, 2004.
[8] De Clercq, E. *Int. J. Antimicrob. Agents* 2009, 33, 307.
[9] Cihlar, T.; Ray, A. S. *Antiviral Research* 2010, 85, 39.
[10] Warnke, D.; Barreto, J.; Temesgen, Z. *J. Clin. Pharmacol.* 2007, 47, 1570.
[11] Balzarini, *J. Pharm. World Sci.* 1994, 16, 113.
[12] Kulik, K.; Radzikowska, E.; Kaczmarek, R.; Baraniak, J.; Stec, W. J.; De, C. E.; Balzarini, J.; Pannecouque, C. *Antiviral Chem. Chemother.* 2011, 21, 143.
[13] Goldring, A. O.; Gilbert, I. H.; Mahmood, N.; Balzarini, J. *Bioorganic &; Medicinal Chemistry Letters* 1996, 6, 2411.
[14] D. Cahard, C. McGuigan, J. Balzarini. *Mini Rev. Med. Chem.* 2004, 4, 371-381.
[15] C. Meier, J. Balzarini. *Antiviral Res.* 2006, 71, 282-292.
[16] N. Valiaeva, J. R. Beadle, K. A. Aldern, J. Trahan, K. Y. Hostetler. *Antiviral Res.* 2006, 72, 10-19
[17] A. S. Ray, K. Y. Hostetler. *Antiviral Res.* 2011, 92, 277-291.
[18] Coe, D. *J. Chem. Soc. Perkin Trans.* 1 1992, 2695.
[19] De Clercq, E.; Holy, A.; Rosenberg, I.; Sakuma, T.; Balzarini, J.; Maudgal, P. C. *Nature (London)* 1986, 323, 464.
[20] Hwang, J.-T.; Choi, J.-R. *Drugs Future* 2004, 29, 163.
[21] Casu, F.; Chiacchio, M. A.; Romeo, R.; Gumina, G. *Curr. Org. Chem.* 2007, 11, 999.
[22] Mao, J. C.; Otis, E. R.; von, E. A. M.; Herrin, T. R.; Fairgrieve, J. S.; Shipkowitz, N. L.; Duff, R. G. *Antimicrob Agents Chemother* 1985, 27, 197.
[23] McKenna, C. E.; Ye, T. G.; Levy, J. N.; Pham, P.; Wen, T.; Bongartz, J. P.; Starnes, M. C.; Cheng, Y. C. *Phosphorus, Sulfur, and Silicon and the Related Elements* 1990, 49-50, 183.
[24] Wnuk, S. F.; Robins, M. J. *Journal of the American Chemical Society* 1996, 118, 2519.
[25] Králiková, Š., Buděšinský, M.; Masojídková, M.; Rosenberg, I. *Tetrahedron Letters* 2000, 41, 955.
[26] Romanenko, V. D.; Kukhar, V. P. *Chemical Reviews* 2006, 106, 3868.
[27] Chen, W.; Flavin, M. T.; Filler, R.; Xu, Z.-Q. *Tetrahedron Lett.* 1996, 37, 8975.
[28] Chen, W.; Flavin, M. T.; Filler, R.; Xu, Z.-Q. *J. Chem. Soc., Perkin Trans.* 1 1998, 3979.
[29] Chen, X.; Wiemer, A. J.; Hohl, R. J.; Wiemer, D. F. *J Org Chem* 2002, 67, 9331.
[30] Weaver, R.; Gilbert, I. H. *Tetrahedron* 1997, 53, 5537.

31 Weaver, R.; Gilbert, I. H.; Mahmood, N.; Balzarini, *J. Bioorganic & Medicinal Chemistry Letters* 1996, 6, 2405.
32 Boudreau, M. A.; Vederas, J. C. *Org. Biomol. Chem.* 2007, 5, 627.
33 Kaiser, M. M.; Jansa, P.; Dracinsky, M.; Janeba, Z. *Tetrahedron* 2012, 68, 4003.
34 Charvet A-S.; Camplo, M. F., P.; Graciet, J-P.; Mourier, N.; Chermann, J-C.; Kraus, J-L. *J. Med. Chem.* 1994, 37, 2216.
35 J Med Chem, 2007, 50, 1840-9 and Mini-Rev. Med. Chem. 2004, 4, 371-8.
36 Mini Rev Med Chem 2004, 4, 409-419.
37 Antimicrob Agents Chemother. 1993, 37, 2247-2250.
38 Mini Rev Med Chem 2004, 4, 395-408.
39 Antiviral Chem and Chemother. 1997, 8, 557.
40 Angew. Chem. Int. Ed. Engl. 1996, 35, 70-72; Mini Rev Med Chem 2002, 2, 219-234; Eur J Org Chem 2006, 1001-1102; J Med Chem 2005, 48, 8079-86.
41 J Med Chem 1999, 42, 1604-1614; J Med Chem, 1998, 4, 1417-1427; Eur J Org Chem, 2006, 197-206.
42 Hostetler K Y, Antiviral research 2009, 82, A84-98; Ray and Hostetler, Antiviral research 011, 92, 277-291.

The invention claimed is:

1. A compound of formula (I), or a pharmaceutically acceptable salt, or prodrug thereof selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative,

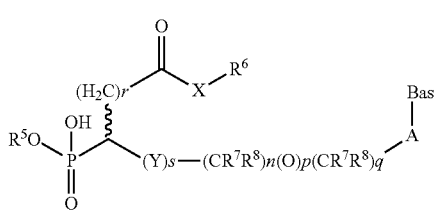

(I)

wherein:
X is selected from O and $NR^{11}$;
Y is selected from O, S and $NR^{12}$;
A is selected from —$(CR^1R^2)n$-, —$(CR^9R^{10})$—, —$(CR^9R^{10})$—$(CR^1R^2)n$-, —$(CR^1R^3)$—$(CR^2R^4)$—$(CR^1R^2)n$-, —$CR^3$=$CR^4$—$(CR^1R^2)n$- and —C≡C—$(CR^1R^2)n$-;
$R^1$ and $R^2$ are independently selected from H, alkyl, hydroxyl, hydroxymethyl and halogen;
$R^3$ and $R^4$ are independently selected from H and alkyl, or $R^3$ and $R^4$ together with the carbon atoms to which they are attached form a mono or bicyclic ring system selected from cycloalkyl, cycloalkenyl, heterocycloalkenyl, aryl and heteroaryl;
$R^5$ is selected from H, P(=O)(OH)$_2$ and P(=O)(OH)—O—P(=O)(OH)$_2$;
$R^6$ is selected from H and alkyl;
$R^7$ and $R^8$ are independently selected from H, alkyl, halogen and hydroxymethyl
$R^9$ and $R^{10}$ together with the carbon atom to which they are attached form a mono or bicyclic ring system selected from cycloalkyl, cycloalkenyl, heterocycloalkyl and heterocycloalkenyl;
$R^{11}$ is selected from H and alkyl;$R^{12}$ is selected from H and alkyl;

m is 0, 1, 2 or 3;
n is 1, 2 or 3;
p is 0 or 1;
q is 0, 1, 2 or 3;
r is 0, 1, 2, 3, 4 or 5;
s is 0 or 1;
Base is a natural or non-natural nucleobase; and
wherein each alkyl, cycloalkyl, cycloalkenyl, heterocycloalkyl, heterocycloalkenyl, aryl and heteroaryl may be optionally substituted.

2. The compound, salt or prodrug of claim 1, wherein:
X is selected from O and $NR^{11}$;
Y is O;
A is selected from —$(CR^1R^2)n$-, —$(CR^1R^3)$—$(CR^2R^4)$—$(CR^1R^2)n$-, —$CR^3$=$CR^4$—$(CR^1R^2)n$- and —C≡C—$(CR^1R^2)n$-;
$R_1$ and $R_2$ are independently selected from H and $C_{1-6}$-alkyl;
$R_3$ and $R_4$ are independently selected from H and $C_{1-6}$-alkyl, or $R_3$ and $R_4$ together with the carbon atoms to which they are attached form a mono or bicyclic ring system selected from $C_3$-$C_{10}$ cycloalkyl, $C_3$-$C_{10}$ cycloalkenyl, aryl and heteroaryl;
$R_5$ is selected from H, P(=O)(OH)$_2$ and P(=O)(OH)—O—P(=O)(OH)$_2$;
$R_6$ is selected from H and $C_{1-6}$-alkyl;
$R_7$ and $R_8$ are independently selected from H and $C_{1-6}$-alkyl;
$R^{11}$ is selected from H and $C_{1-6}$-alkyl;
m is 1 or 2;
n is 1 or 2;
p, q and r are 0;
s is 1; and
Base is a natural or non-natural nucleobase.

3. The compound, salt or prodrug of claim 1, wherein:
X is O;
Y is O;
A is selected from —$(CR^1R^2)n$-, —$(CR^9R^{10})$—$(CR^1R^2)n$-, —$(CR^1R^3)$—$(CR^2R^4)$—$(CR^1R^2)n$-, —$CR^3$=$CR^4$—$(CR^1R^2)n$- and —C≡C—$(CR^1R^2)n$-;
$R_1$ and $R_2$ are independently selected from H and $C_{1-6}$-alkyl;
$R_3$ and $R_4$ are independently selected from H and $C_{1-6}$-alkyl, or $R_3$ and $R_4$ together with the carbon atoms to which they are attached form a $C_3$-$C_{10}$ cycloalkenyl or aryl;
$R^9$ and $R^9$ together with the carbon atom to which they are attached form a cyclohexyl, cyclopropyl, cyclopentyl, cyclohexenyl or norbornenyl ring;
$R_5$ is H;
$R_6$ is selected from H and $C_{1-6}$-alkyl;
$R_7$ and $R_8$ are independently selected from H and $C_{1-6}$-alkyl;
$R^{11}$ is selected from H and $C_{1-6}$-alkyl;
m is 1 or 2;
n is 1 or 2;
p, q and r are 0;
s is 1; and
Base is a natural or non-natural nucleobase.

4. The compound, salt or prodrug of claim 1, wherein:
s is 1;
Y is O;
X is O;
$R^5$ and $R^6$ are both H;
m is 0 or 1;
p, q and r are all 0;

A is —(CR¹CR²)$_n$—;

n is 1, 2 or 3;

R¹ and R¹ are each independently selected from H and alkyl and hydroxyalkyl;

R⁷ and R⁸ are each independently selected from H and alkyl;

p, q and r are all 0.

5. The compound, salt or prodrug of claim 1, wherein:

s is 1;

Y is O;

X is O;

R⁵ is H;

R⁶ is H or alkyl;

p, q and r are all 0;

m is 1;

R⁷ and R⁸ are each independently selected from H and alkyl;

A is selected from —(CR¹CR²)$_n$, —(CR³=CR⁴)—(CR¹CR²)$_n$—, —C≡C—(CR¹CR²)$_n$—, —(CR⁹R¹⁰)—(CR¹R²)$_n$—;

n is 1 or 2;

R¹ and R² are each independently selected from H and alkyl,

R³ and R⁴ are each independently selected from H and alkyl, or together with the carbon atoms to which they are attached form a phenyl ring; and R⁹ and R⁹ together with the carbon atom to which they are attached form a cyclohexyl, cyclopropyl, cyclopentyl, cyclohexenyl or norbornenyl ring.

6. The compound, salt or prodrug of claim 1, wherein:

Y is O;

s is 1;

X is O;

R⁵ and R⁶ are both H;

A is —(CR¹R³)—(CR²R⁴)—(CR¹R²)$_n$— or —(CR¹R²)$_n$—;

n is 1;

p, q and r are all 0;

m is 0 or 1

R¹ and R² are each independently selected from H, hydroxyl, hydroxymethyl and alkyl;

R³ and R⁴ are each independently selected from H and alkyl; and

R⁷ and R⁸ are each independently selected from H, alkyl and hydroxymethyl.

7. The compound, salt or prodrug of claim 1, wherein the base is a purine or pyrimidine nucleobase.

8. The compound of claim 1 which is selected from the following, or a pharmaceutically acceptable salt, or prodrug thereof selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative:

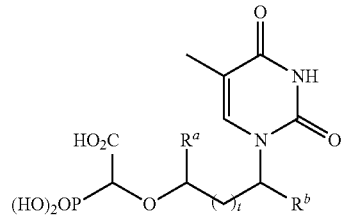

8a R$^a$ = R$^b$ = H, t = 0
8b R$^a$ = Me, R$^b$ = H, t = 0
8c R$^a$ = H, R$^b$ = Me, t = 0
8d R$^a$ = R$^b$ = H, t = 1
8e R$^a$ = H, R$^b$ = CH₂OH, t = 0

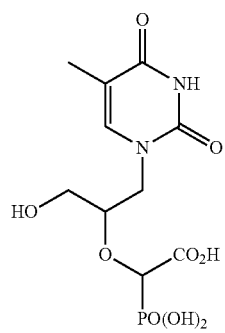

24

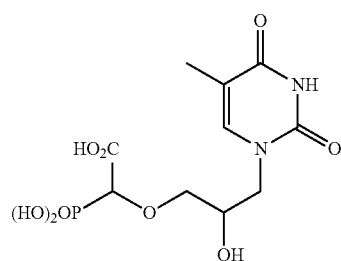

26

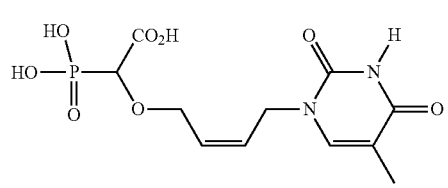

13a

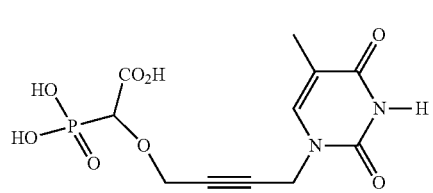

13b

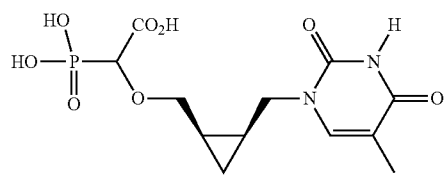

13c

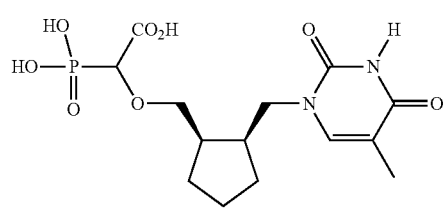

13d

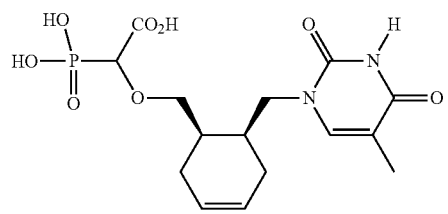

13e

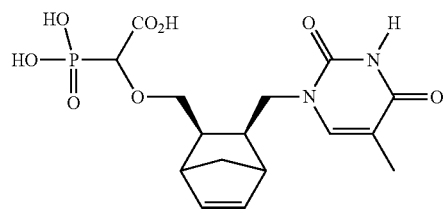

13f

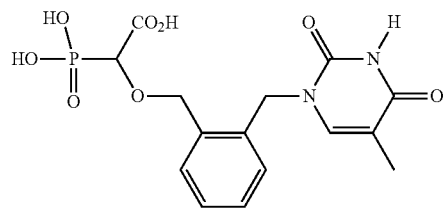

13g

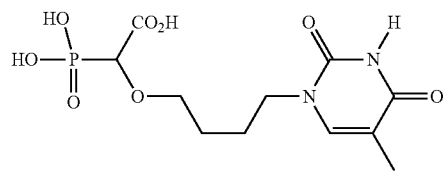

13h

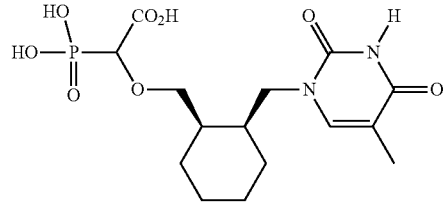

13i

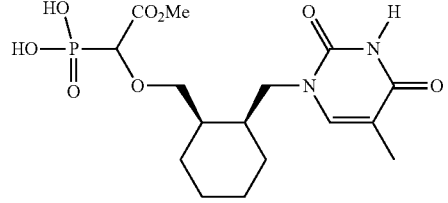

13j

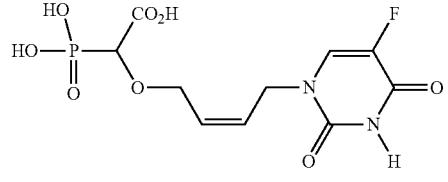

13k

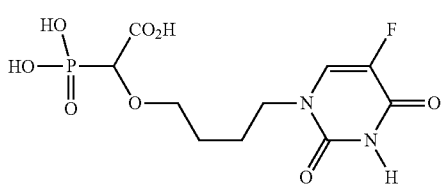

13l

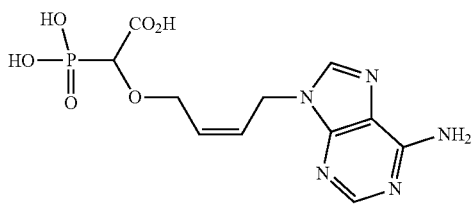

13m

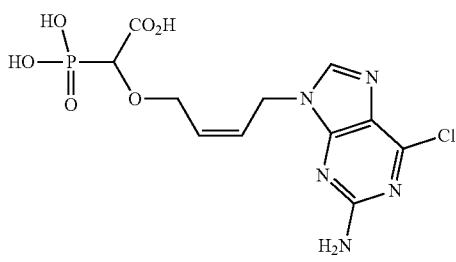

13n

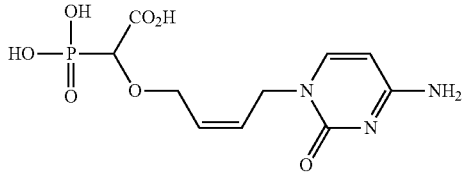

13o

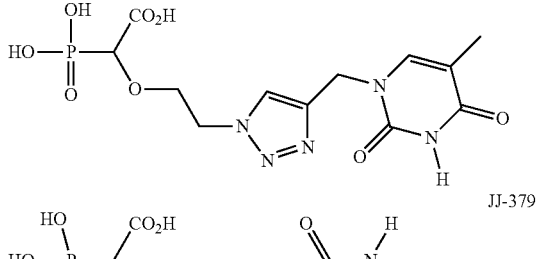

JJ-210

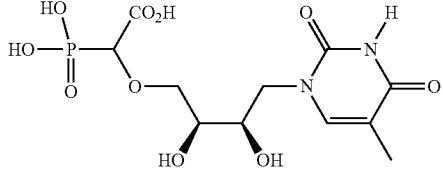 [SMILES: Cc1cn(C[C@@H](O)[C@@H](O)COC(C(=O)O)P(=O)(O)O)c(=O)[nH]c1=O]

JJ-379

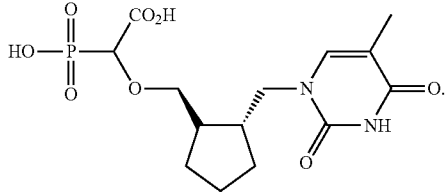

JJ-609-F

9. A pharmaceutical composition comprising a compound of formula (I), or a pharmaceutically acceptable salt or prodrug thereof selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative, wherein:

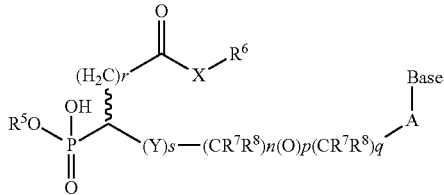

(I)

X is selected from O and NR$^{11}$;

Y is selected from O, S and NR$^{12}$;

A is selected from —(CR$^1$R$^2$)n-, —(CR$^9$R$^{10}$)—, —(CR$^9$R$^{10}$)—(CR$^1$R$^2$)n-, —(CR$^1$R$^3$)—(CR$^2$R$^4$)—(CR$^1$R$^2$)n-, —CR$^3$=CR$^4$—(CR$^1$R$^2$)n- and —C≡C—(CR$^1$R$^2$)n-;

R$^1$ and R$^2$ are independently selected from H, alkyl, hydroxyl, hydroxymethyl and halogen;

R$^3$ and R$^4$ are independently selected from H and alkyl, or R$_3$ and R$_4$ together with the carbon atoms to which they are attached form a mono or bicyclic ring system selected from cycloalkyl, cycloalkenyl, heterocycloalkenyl, aryl and heteroaryl;

R$^5$ is selected from H, P(=O)(OH)$_2$ and P(=O)(OH)—O—P(=O)(OH)$_2$;

R$^6$ is selected from H and alkyl;

R$^7$ and R$^8$ are independently selected from H, alkyl, halogen and hydroxymethyl R$^9$ and R$^{10}$ together with the carbon atom to which they are attached form a mono or bicyclic ring system selected from cycloalkyl, cycloalkenyl, heterocycloalkyl and heterocycloalkenyl;

R$^{11}$ is selected from H and alkyl; R$^{12}$ is selected from H and alkyl;

m is 0, 1, 2 or 3;

n is 1, 2 or 3;

p is 0 or 1;

q is 0, 1, 2 or 3;

r is 0, 1, 2, 3, 4 or 5;

s is 0 or 1;

Base is a natural or non-natural nucleobase; and wherein each alkyl, cycloalkyl, cycloalkenyl, heterocycloalkyl, heterocycloalkenyl, aryl and heteroaryl may be optionally substituted;

admixed with a pharmaceutically acceptable diluent, excipient or carrier.

10. A method of treating a viral disorder, said method comprising administering to a mammal a therapeutically effective amount of compound of formula (I), or a pharmaceutically acceptable salt or prodrug thereof selected from a phosphoramidate derivative, a SATE (S-acyl-2-thioethyl) ester derivative, a pivaloyloxymethyl (POM) derivative, an isopropyloxymethylcarbonyl (POC) derivative, a cyclosaligenyl (cycloSal) derivative and an alkyloxyalkyl derivative:

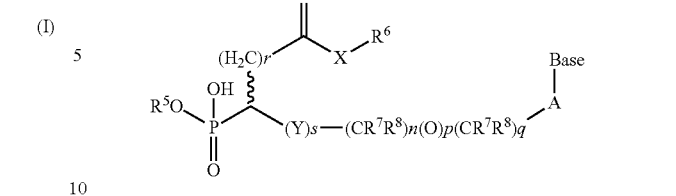

(I)

wherein:

X is selected from O and NR$^{11}$;

Y is selected from O, S and NR$^{12}$;

A is selected from —(CR$^1$R$^2$)n-, —(CR$^9$R$^{10}$)—, —(CR$^9$R$^{10}$)—(CR$^1$R$^2$)n-, —(CR$^1$R$^3$)—(CR$^2$R$^4$)—(CR$^1$R$^2$)n-, —CR$^3$=CR$^4$—(CR$^1$R$^2$)n- and —C≡C—(CR$^1$R$^2$)n-;

R$^1$ and R$^2$ are independently selected from H, alkyl, hydroxyl, hydroxymethyl and halogen;

R$^3$ and R$^4$ are independently selected from H and alkyl, or R$_3$ and R$_4$ together with the carbon atoms to which they are attached form a mono or bicyclic ring system selected from cycloalkyl, cycloalkenyl, heterocycloalkenyl, aryl and heteroaryl;

R$^5$ is selected from H, P(=O)(OH)$_2$ and P(=O)(OH)—O—P(=O)(OH)$_2$;

R$^6$ is selected from H and alkyl;

R$^7$ and R$^8$ are independently selected from H, alkyl, halogen and hydroxymethyl R$^9$ and R$^{10}$ together with the carbon atom to which they are attached form a mono or bicyclic ring system selected from cycloalkyl, cycloalkenyl, heterocycloalkyl and heterocycloalkenyl;

R$^{11}$ is selected from H and alkyl; R$^{12}$ is selected from H and alkyl;

m is 0, 1, 2 or 3;

n is 1, 2 or 3;

p is 0 or 1;

q is 0, 1, 2 or 3;

r is 0, 1, 2, 3, 4 or 5;

s is 0 or 1;

Base is a natural or non-natural nucleobase; and wherein each alkyl, cycloalkyl, cycloalkenyl, heterocycloalkyl, heterocycloalkenyl, aryl and heteroaryl may be optionally substituted.

11. A process for preparing the compound, salt or prodrug of claim 1, the process comprising (A) reacting a compound of formula (X), wherein P is a protecting group, with a compound of formula (XI),

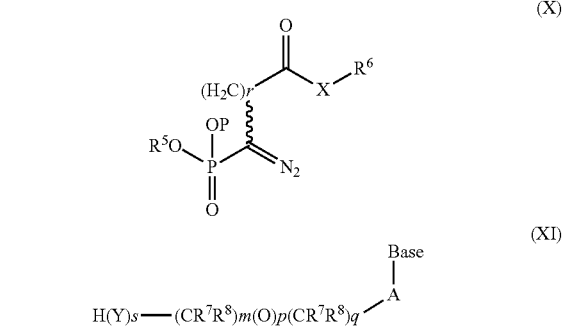

removing the protecting groups to afford the compound of formula (I); and optionally converting the compound of formula (I) to the pharmaceutically acceptable salt or prodrug; or (B) reacting a compound of formula (XX), wherein P is a protecting group,

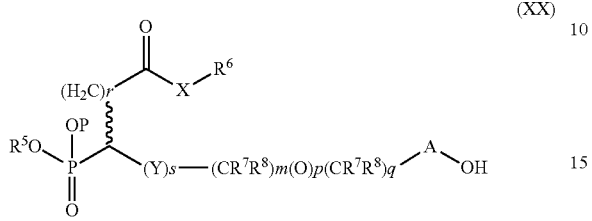
(XX)

with a base;

removing the protecting groups to afford the compound of formula (I); and optionally converting the compound to the pharmaceutically acceptable salt or prodrug;

wherein X is selected from O and $NR^{11}$;

Y is selected from O, S and $NR^{12}$;

A is selected from $-(CR^1R^2)n-$, $-(CR^9R^{10})-$, $-(CR^9R^{10})-(CR^1R^2)n-$, $-(CR^1R^3)-(CR^2R^4)-(CR^1R^2)n-$, $-CR^3=CR^4-(CR^1R^2)n-$ and $-C\equiv C-(CR^1R^2)n-$;

$R^1$ and $R^2$ are independently selected from H, alkyl, hydroxyl, hydroxymethyl and halogen;

$R^3$ and $R^4$ are independently selected from H and alkyl, or $R_3$ and $R_4$ together with the carbon atoms to which they are attached form a mono or bicyclic ring system selected from cycloalkyl, cycloalkenyl, heterocycloalkenyl, aryl and heteroaryl;

$R^5$ is selected from H, $P(=O)(OH)_2$ and $P(=O)(OH)-O-P(=O)(OH)_2$;

$R^6$ is selected from H and alkyl;

$R^7$ and $R^8$ are independently selected from H, alkyl, halogen and hydroxymethyl $R^9$ and $R^{10}$ together with the carbon atom to which they are attached form a mono or bicyclic ring system selected from cycloalkyl, cycloalkenyl, heterocycloalkyl and heterocycloalkenyl;

$R^{11}$ is selected from H and alkyl; $R^{12}$ is selected from H and alkyl;

m is 0, 1, 2 or 3;

n is 1, 2 or 3;

p is 0 or 1;

q is 0, 1, 2 or 3;

r is 0, 1, 2, 3, 4 or 5;

s is 0 or 1;

Base is a natural or non-natural nucleobase; and wherein each alkyl, cycloalkyl, cycloalkenyl, heterocycloalkyl, heterocycloalkenyl, aryl and heteroaryl may be optionally substituted.

12. A process for identifying candidate compounds capable of inhibiting HIV-RT comprising generating candidate compounds by conventional structure-activity relationship (SAR) modification of the compound of claim 1; and screening the candidate compounds for inhibition of HIV-RT.

* * * * *